US006172045B1

(12) United States Patent
Theodore et al.

(10) Patent No.: US 6,172,045 B1
(45) Date of Patent: *Jan. 9, 2001

(54) CLUSTER CLEARING AGENTS

(75) Inventors: Louis J. Theodore, Lynnwood; Donald B. Axworthy, Brier, both of WA (US)

(73) Assignee: NeoRx Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/659,761

(22) Filed: Jun. 6, 1996

Related U.S. Application Data

(63) Continuation-in-part of application No. 08/350,551, filed on Dec. 7, 1994, now Pat. No. 6,075,010.

(51) Int. Cl.$^7$ ............................. A01N 43/04; A61K 31/70
(52) U.S. Cl. ................................ 514/24; 514/23; 514/25
(58) Field of Search ........................... 424/178.1; 514/23, 514/24, 25, 53, 54, 61, 62

(56) References Cited

U.S. PATENT DOCUMENTS

| | | |
|---|---|---|
| 4,179,337 | 12/1979 | Davis et al. . |
| 4,358,439 | 11/1982 | Sieber et al. . |
| 4,410,688 | 10/1983 | Denkewalter et al. . |
| 4,507,466 | 3/1985 | Tomalia et al. . |
| 4,678,667 | 7/1987 | Meares et al. . |
| 4,732,863 | 3/1988 | Tomasi et al. . |
| 4,863,713 | 9/1989 | Goodwin et al. . |
| 4,902,502 | 2/1990 | Nitecki et al. . |
| 4,904,481 | 2/1990 | Fathman et al. . |
| 4,923,985 | 5/1990 | Gansow et al. . |
| 5,089,261 | 2/1992 | Nitecki et al. . |
| 5,141,966 | 8/1992 | Porath . |
| 5,183,660 | 2/1993 | Ikeda et al. . |
| 5,215,927 | 6/1993 | Berenson et al. . |
| 5,256,395 | 10/1993 | Barbet et al. . |
| 5,281,698 | 1/1994 | Nitecki . |
| 5,342,940 | 8/1994 | Ono et al. . |

FOREIGN PATENT DOCUMENTS

| | | |
|---|---|---|
| 031 303 | 7/1981 | (EP) . |
| 0251494 | 1/1988 | (EP) . |
| 0451824 | 10/1991 | (EP) . |
| 0496074 | 7/1992 | (EP) . |
| 519 554 | 12/1992 | (EP) . |
| 8900427 * | 3/1989 | (GB) . |
| 8910140 | 11/1989 | (WO) . |
| WO 89/10140 | 11/1989 | (WO) . |
| 9012050 | 10/1990 | (WO) . |
| WO 92/12730 | 8/1992 | (WO) . |
| 9514493 * | 6/1993 | (WO) . |
| WO 93/15210 | 8/1993 | (WO) . |
| 9325240 * | 12/1993 | (WO) . |
| WO 94/04702 | 3/1994 | (WO) . |
| WO 94/11398 | 5/1994 | (WO) . |
| 9515978 * | 6/1995 | (WO) . |
| WO 95/15770 | 6/1995 | (WO) . |
| WO 95/15979 | 6/1995 | (WO) . |

OTHER PUBLICATIONS

Axworthy et al., "Antibody Pretargeting For Radioimmunotherapy: A Three–Step Approach In Tumored Nude Mice," *The Journal Of Nuclear Medicine*; Proceedings Of The 39$^{th}$ Annual Meeting 33: p. 880, Abstract No. 234, 1992.

Sanderson et al., "Preparation And Characterization Of Biotin Conjugates Of Anti–Pan–Carcinoma NR–LU–10 Monoclonal Antibody For A Three Step Radioimmunotherapy," *The Journal Of Nuclear Medicine*; Proceedings Of The 39$^{th}$ Annual Meeting 33: p. 880, Abstract No. 233, 1992.

Schmidt et al., "Synthesis of peptide alkaloids. 5. New method for synthesis of ansa peptides. Amino acids and peptides. 34," *J. Org. Chem.* 47(17):3261–3264, 1982.

Abuchowski et al., "Alteration of Immunological Properties of Bovine Serum Albumin by Covalent Attachment of Polyethylene Glycol," *J. of Biological Chem.* 252(11):3578–3581, 1997.

Abuchowski et al., "Cancer Therapy with Chemically Modified Enzymes. I. Antitumor Properties of Polyethylene Glycol–Asparaginase Conjugates," *Can. Biochem. Biophys.* 7:175–186, 1984.

Basch et al., in *Journal of Immunological Methods* 56:269–280, 1983.

Beauchamp et al., "A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin," *Analytical Biochem* 131:25–33, 1983.

Bodenmuller et al., in *Embo J.* 5(8):1825–9, 1986.

Boehringer Mannheim Catalog—1991, pp. 49–59.

Chen et al., "Properties of Two Urate Oxidases Modified by the Covalent Attachment of Poly (ethylene Glycol)," *Biochemica et Biophysica Acta* 660:293–298, 1981.

Davis et al., "Alteration of the circulating life and antigenic properties of bovine adenosine deaminase in mice by attachment of polyethylene glycol," *Clin. Exp. Immunol.* 46:649–652, 1981.

Goodwin and Hnatowich, Letter to the Editor/Reply, in *J. Nucl. Med.* 32(4):750–751, 1991.

(List continued on next page.)

Primary Examiner—Patricia A. Duffy
(74) Attorney, Agent, or Firm—Seed Intellectual Property Law Group PLLC

(57) ABSTRACT

Cluster clearing agents (CCAs) and the use thereof are discussed. CCAs are composed of a hepatic clearance directing moiety which directs the biodistribution of a CCA-containing construct to hepatic clearance; and a binding moiety which mediates binding of the CCA to a compound for which rapid hepatic clearance is desired.

8 Claims, 16 Drawing Sheets

OTHER PUBLICATIONS

Goodwin et al., "Pharmacokinetics of Biotin–Chelate Conjugates for Pretargeted Avidin–Biotin Immunoscintigraphy," *J. Nucl. Med.*, p. 880, Abstract No. 232, 1992.

Green, "The Use of [$^{14}$C] Biotin for Kinetic Studies and for Assay," *Biochem. J.* 89:585, 1963.

Hnatowich et al., "Investigations of Avidin and Biotin for Imaging Applications," 28(8):1294–1302, 1987.

Hubbard et al., "Suppression of the Anti–DNP IgE Response with Tolerogenic Conjugates of DNP with Polyvinyl Alcohol," *J. of Immunology* 126(2), 1981.

Kalofonos et al., "Imaging of Tumor in Patients with Indium–111–Labeled Biotin and Streptavidin–Conjugated Antibodies: Preliminary Communication," *J. Nucl. Med.* 31(11):1791–1796, 1990.

Koch and Macke, "$^{99m}$Tc Labeled Biotin Conjugate in a Tumor 'Pretargeting' Approach with Monoclonal Antibodies," *Angew. Chem. Intl. Ed. Engl.* 31(11):1507–1509, 1992.

Krull et al., "Solid–phase derivatization reactions for biomedical liquid chromatography," *J. Chromatography B: Biomedical Applications* 659:19–50, 1994.

Lee et al., "Abrogation of the Antibenzylpencilloyl (BPO) IgE Response with BPO–Polyvinyl Alcohol Conjugates," *Int. Archs Allergy appl. Immun.* 63:1–13, 1980.

Lee et al., "New Synthetic Cluster Ligands for Galactose/N–Acetylgalactosamine–Specific Lectin of Mammalian Liver," *Biochemistry* 23:4255–4261, 1984.

Lee et al., "Suppresion of Reaginic Antibodies with Modified Allergens," *Int. Arch Allergy appl. Immun.* 63:1–13, 1980.

Leonard et al., "Synthesis of monomethoxypolyoxyethylene–Bound haemoglobins," *Tetrahedron* 40(9):1581–1584, 1984.

Ling et al., "A General Study of the Binding and Seperation in Partition Affinity Ligand Assay. Immunoassay of $\beta_2$–Microglobulin," *J. Immunological Methods* 59:327–337, 1983.

Mattes, J., "Biodistribution of Antibodies After Intraperitoneal or Intravenous Injection and Effect of Carbohydrate Modifications," 79(4):855–863, 1987.

Mauk et al., "Targeting of lipid vesicles: Specificity of carbohydrate receptor analogues for leukocytes in mice," *Proc. Natl. Acad. Sci. USA* 77:4430–4434, 1980.

Mauk et al., "Vesicle Targeting: Timed Release and Specificity for Leukocytes in Mice by Subcutaneous Injection," *Science* 207(18), 1980.

Paganelli et al., "Intraperitoneal Radio–Localization of Tumors Pre–Targeted by Biotinylated Monoclonal Antibodies," *Int J. Cancer* 45:1184–1189, 1990.

Paganelli et al. "Monoclonal Antibody Pretargeting techniques for Tumour Localization: The Avidin–Biotin System," *Nuclear Medicine Communications* 121:211–234, 1991.

Pierce Biochemicals, in *Immunotechnology 1*, 1990.

Ponpipom et al., "Cell Surface carbohydrates for targeting studies," 58:214, 1980.

Ponpipom et al., "Cell–Specific Ligands for Selecting Drug Delivery to Tissues and Organs," *J. Med. Chem.* 24(12):1388–1395, 1981.

Rosario et al., "Bolton–Hunter and Biotin Derivatized Polylysine: A New Multi–Valent Peptide Reagent for In Vivo Pre–Targeting with Streptavidin Conjugates," *J. Nucl. Med.* 32(5):p. 993, Abstract No. 356, 1991.

Rosebrough, "Plasma Stability and Pharmacokinetics of Radio–Labeled Deferoxamine–Biotin Derivatives" *J. Nucl. Med.*, p. 880, Abstract No. 235, 1992.

Savoca et al., "Preparation of a Non–Immunogenic Arginase by the Covalent Attachment of Polyethylene Glycol," *Biochemica et Biophysica Acta* 578:47–53, 1979.

Schnaar et al., "Adhesion of Chicken Hepatocytes to Polycrylamide Gels Derivatized with N–Acetylglucosamine," *Journal of Biological Chemistry* 253(21):7940–7951, 1978.

Schulling, H. et al., "Design of Compounds Having Enhanced Tumour Uptake, Using Serum Albumin as a Carrier, Part 2," *Nucl. Med. Biol.* 19:6, 685–695, 1992.

Sharon and Lis, "Carbohydrates in Cell Recognition," *Scientific American* 268(1):82–89, 1993.

Sheldon et al., "Targeting of [$^{111}$In] Biocytin to Cultured Ovarian Adenocarcinoma Cells Using Covalent Monoclonal Antibody–Streptavidin Conjugates," *Appl. Radiat. Isot.* 43(11):1399–1402, 1992.

Sigma Catalogue—1984, p. 250.

Sinn, H. et al., "Design of Compounds Having an Enhanced Tumour Uptake, Using Serum Albumin as a Carrier, Part 1," *Nucl. Med. Biol.* 17:8, 819–827, 1990.

Tolleshaug, "Binding and Internalization of Asialoglycoproteins by Isolated Rat Hepatocytes," *Int. J. Biochem.* 13:45–51, 1981.

Virzi et al., "The Preparation and Evaluation of 12 Biotin Derivatives Labeled with Tc–99M," *J. Nucl. Med.*, 920, Abstract No. 403, 1992.

Weigel, "Endocytic Components: Identification and Characterization," *Subcellular Biochemistry*, vol. 19, Chapter 5, Endocytosis and Function of the Hepatic Asialoglycoprotein Receptor, edited by Bergeron et al., New York, pp. 125–161, 1993.

Weigel, "GlycoConjugates Composition, Structure and Function," Chapter 14, Mechanisms and Control of Glycocnjugate Turnover, edited by Allen et al, Marcel Dekker, Inc., NY, pp 421–497, 1992.

Sprengard et al Bioorganic and Medicinal Chemistry Letters 6(5) 509–514 (1996).

Doris A. Wall et al., The Galactose–Specific Recognition System of Mammalian Liver: the Route of Ligand Internalization in Rat Hepatocytes, *Cell* 25, 79–93, Aug. 1980.

Yuan Chuan Lee et al., 2–Imino–2–methoxyethyl 1–Thioglycosides: New Reagents for Attaching Sugars to Proteins, *Biochemistry* 15:18, 3956–3962, 1976.

Mark J. Krantz et al., Attachment of Thioglycosides to Proteins: Enhancement of Liver Membrane Binding, *Biochemistry* 15:18, 3963–3968, 1976.

Peter van der Sluijs et al., Drug Targeting to the Liver with Lactosylated Albumins: Does Glycoprotein Target the Drug or Is the Drug Targeting the Glycoprotein?, *Hepatology* 6::4, 723–728, 1986.

Anatol G. Morell et al., the Role of Sialic Acid in Determining the Survival of Glycoproteins in the Circulation, *Journal of Biological Chemistry* 246:5, 1461–1467, 1971.

G. Galli et al., A Radiopharmaceutical for the Study of the Liver: $^{99m}$Tc–DTPA–Asialo–Orosomucoid, *The Journal of Nuclear Medicine and Allied Sciences*, 110–116, Apr.–Jun. 1988.

S.K. Sharma et al., Inactivation and clearance of an anti–CEA carboxypeptidase G2 conjugate in blood after localisation in a xenograft model, *Br. J. Cancer* 61, 659–662, 1990.

Robert W. Jansen et al., Hepatic Endocytosis of Various Types of Mannose–terminated Albumins, *The Journal of Biological Chemistry* 266:5, 3343–3348, 1991.

D. A. Goodwin et al., New Methods for Localizing Infection: A Role for Avidin–Biotin?, *The Jounral of Nuclear Medicine* 33:10, 1816–1818, Oct. 1992.

David A. Goodwin et al., Pretargeted Immunoscintigraphy: Effect of Hapten Valency on Murine Tumor Uptake, *The Journal of Nuclear Medicine* 33:11, 2006–2103, Nov. 1992.

Paul F. Sieving et al., Preparation and Characterization of Paramagnetic Polychelates and Their Protein Conjugates, *Bioconjugate Chem 1*, 65–71, 1990.

G. Paganelli et al., Monoclonal antibody pretargeting techniques for tumour localization: the avidin–biotin system, *Nuclear Medicine Communications 12*, 211–234, 1991.

David R. Vera et al., Tc–99m Galactosyl–Neoglycoalbumin: In Vitro Characterization of Receptor Mediated Binding, *J Nucl Med* 25:7, 779–787, 1984.

Jean Haensler et al., Synthesis and Characterization of a Trigalactosylated Bisacridine Compound to Target DNA to Hepatocytes, *Bioconjugate Chem. 4*, 85–93, 1993.

C. Wu et al., Investigations of N–linked Macrocycles for $^{111}$In and $^{90}$Y Labeling of Proteins, *Nucl. Med. Biol, 19*:2, 239–244, 1992.

Paul H. Weigel, Endocytosis and Function of the Hepatic Asialoglycoprotein Receptor, *Endocytosis and Functin of GalNAc Receptor*, Chapter 5,125–161.

Reiko T. Lee, New Synthetic Cluster Ligands for Galactose/N–Acetylgalactosamine–Specific Lectin of Mammalian Liver, *Biochemistry 23*, 4255–4261, 1984.

Erik A. L. Biessen et al., Synthesis of Cluster Galatosides with High Affinity for the Hepatic Asialoglycoprotein Receptor, *J. Med. Chem. 38*, 1538–1546, 1995.

June Rae Merwin et al., Targeted Delivery of DNA Using YEE(GaINAcAH)$_{xp}$, a Synthetic Glycopeptide Ligand for the Asialoglycoprotein Receptor, *Bioconjugate Chem. 5*, 612–620, 1994.

Mark A. Findeis, Stepwise systhesis of a GalNAc–containing cluster glycoside ligand of the asialoglycoprotein receptor, *Int. J. Peptide Protein Res. 43*, 477–485, 1994.

Reiko T. Lee et al., Preparation of Cluster Glycosides of N–Acetylgalactosamine That Have Subnanomolar Binding Constants Towards the Mammalian Hepatic Gal/GalNAc–specific Receptor, *Glycoconjugate J 4*, 317–328, 1987.

Timothy D. McKee et al., Preparation of Asialoorosomucoid–Polylysine Conjugates, *Bioconjugate Chem. 5*, 306–311, 1994.

Samar E. Makhlouf et al., Antisera Specificities to β–D–Galactopyranoside Cluster Ligands, *Carbohydrate Research 132*, 93–103, 1984.

A.S. Chaudhari et al., Coupling of Amino Acids and Amino Sugars with Cyanuric Chloride (2,4,6–Trichloro–s–triazine)$^{1}$, *Canadian Journal of Chemistry 50*:13, 1987–1990, Jul. 1, 1972.

Paul H. Weigel, Mechanisms and Control of Glycoconjugate Turnover, *Glycoconjugatges*, Chapter 14, 421–497, 1992.

Christian Plank et al., Gene Transfer into Hepatocytes Using Asialoglycoprotein Receptor Mediated Endocytosis of DNA Complexed with an Artificial Tetra–Antennary Galactose Ligand, *Bioconjugate Chem. 3*, 533–539, 1992.

\* cited by examiner

CLUSTER CLEARING AGENTS

CROSS-REFERENCE TO RELATED APPLICATIONS

This application is a continuation-in-part of U.S. application Ser. No. 08/350,551, filed Dec. 7, 1994 now U.S. Pat. No. 6,075,010 for PRETARGETING METHODS AND COMPOUNDS.

TECHNICAL FIELD

The present invention relates to cluster clearing agents (CCAs), reagents for the preparation thereof and associated methods and compositions. CCAs impact the elimination and biodistribution of constructs that incorporate or become associated with such agents in a manner resulting in increased elimination via a hepatic route. The CCA-associated constructs also generally exhibit a decreased serum half-life in comparison to counterpart compounds which do not incorporate or become associated with CCAs.

BACKGROUND OF THE INVENTION

Conventional cancer therapy is limited by the problem that the generally attainable targeting ratio (ratio of administered dose of active agent localizing to tumor versus administered dose circulating in blood) is low. This limitation is generally encountered in systemic administration of chemotherapeutic agents as well as in administration of monoclonal antibody-active agent conjugates. Systemic administration involves exposure of healthy tissue to the active agent. Also, as a result of the relatively long half life of a monoclonal antibody, non-target tissue is exposed to circulating antibody-active agent conjugate. Improvement in targeting ratio is therefore sought.

A method employed to improve targeting ratio is referred to generally as pretargeting. In pretargeting, a targeting moiety is formed of a targeting agent and a receptor. The active agent is associated with a ligand for the receptor. The targeting moiety is administered to a recipient, and permitted to localize to the target site with binding at that site mediated by the targeting agent. When target site localization and sufficient elimination of circulating targeting moiety is achieved by the recipient's metabolism, the active agent-ligand is administered. The ligand component of the construct binds to the pretargeted receptor, thereby delivering the active agent to the target.

Pretargeting is made more efficient by administration of a clearing agent to facilitate elimination of circulating targeting moiety. Various clearing agents have been disclosed. Galactose-human serum albumin (HSA)-biotin clearing agents have been employed in pretargeting protocols employing a monoclonal antibody-streptavidin targeting moiety and a biotin-active agent construct. Such clearing agents are discussed in PCT/US93/05406. Derivatization by galactose facilitates elimination of complexes of monoclonal antibody-streptavidin-biotin-HSA-galactose via Ashwell receptors in the liver. These clearing agents rapidly decrease circulating monoclonal antibody-streptavidin levels in patients. Since pretargeting methods are enhanced using clearing agents, improvements in such clearing agents are sought.

SUMMARY OF THE INVENTION

The present invention is directed to low molecular weight cluster clearing agents (CCAs) which meet certain performance criteria and are amenable to scale up for commercial production. Preferred CCAs of the present invention preferably exhibit one or more of the following characteristics:

rapid, efficient complexation with serum-associated targeting moiety-ligand (or anti-ligand) conjugate in vivo;

rapid clearance from the blood of serum-associated targeting moiety conjugate capable of binding a subsequently administered complementary anti-ligand or ligand containing molecule;

high capacity for clearing (or inactivating) large amounts of serum-associated targeting moiety conjugate; and low immunogenicity.

In addition, CCAs of the present invention are preferably capable of achieving circulating targeting moiety clearance without compromising the binding potential of the pretargeted targeting moiety, either directly by binding of the CCA thereto or indirectly by binding of CCA metabolites thereto. The present invention also contemplates CCAs of defined chemistry to facilitate characterization, manufacturing and quality control. The CCAs of this invention are also designed to be effective over a broad dose range to avoid the desirability of extensive dose optimization. The present invention further provides CCAs of increased efficiency in clearance of circulating targeting moiety.

Preferred CCAs of present invention incorporate (1) a cluster hepatic clearance directing moiety; and (2) a binding moiety incorporating a member of a ligand/anti-ligand pair or a lower affinity form thereof. The cluster hepatic clearance directing moiety is composed of a cluster of sugar residues arranged on a cluster backbone and mediates hepatic clearance of the CCA via recognition of the sugar clusters by a hepatocyte receptor. The ligand or anti-ligand binding moiety facilitates binding to targeting moiety-ligand/anti-ligand conjugate. Preferably, CCAs of the present invention range in molecular weight from between about 1,000 and about 20,000 daltons, more preferably from about 2,000 to 16,000daltons. Such preferred CCAs generally incorporate between about 4 and about 32 sugar residues, with about 16 sugar residues more preferred.

More preferred CCAs of the present invention are characterized by one or more of the following:

Unnatural orientation of ligand (e.g., 1-biotin) and anti-ligand (e.g., streptavidin formed from d-amino acids);

Secondary amide connecting a sugar residue to the cluster backbone of the CCA;

High affinity sugar for binding to the Ashwell receptor (e.g., N-acetylgalactosamine);

Orientation for sugar attachment (e.g., alpha-orientation sugar attachment is generally preferred for N-acetylgalactosamine hexoses, and beta-orientation sugar attachment is generally preferred for galactose hexoses);

Appropriate linking atom for sugar attachment (e.g., sulfur linker atoms are generally preferred with regard to metabolic stability of CCAs);

Optimized spacer between the linker atom and the nitrogen atom of the amide connecting the sugar residue to the cluster backbone of the CCA;

Tertiary amine adjacent to the ligand or anti-ligand component to enhance in vivo stability of the CCA; and Extended linker between the cluster backbone and the ligand or anti-ligand to improve the bioavailability of said ligand or anti-ligand.

CCAs of the present invention may also be employed to remove toxic or potentially toxic moieties from a recipient's circulation or extravascular space. In this embodiment, the CCA comprises a hepatic clearance directing moiety and a binding moiety capable of recognizing a component or an epitope associated with the toxic or potentially toxic moieties.

Another embodiment of the present invention is a CCA-protein clearing agent. For example, HSA may be derivatized with one or more CCAs, preferably 1 or 2 CCAs, and optionally derivatized by hexose residues. By virtue of the synthetic nature of the CCA and the methylated amide bond(s) incorporated in the linker/extender between the cluster and their binding moiety, the CCA is resistant to metabolic degradation. Consequently, any CCA-biotin metabolites of this proteinaceous clearing agent are likely to be retained n liver hepatocytes.

DETAILED DESCRIPTION OF THE INVENTION

Figure 1:
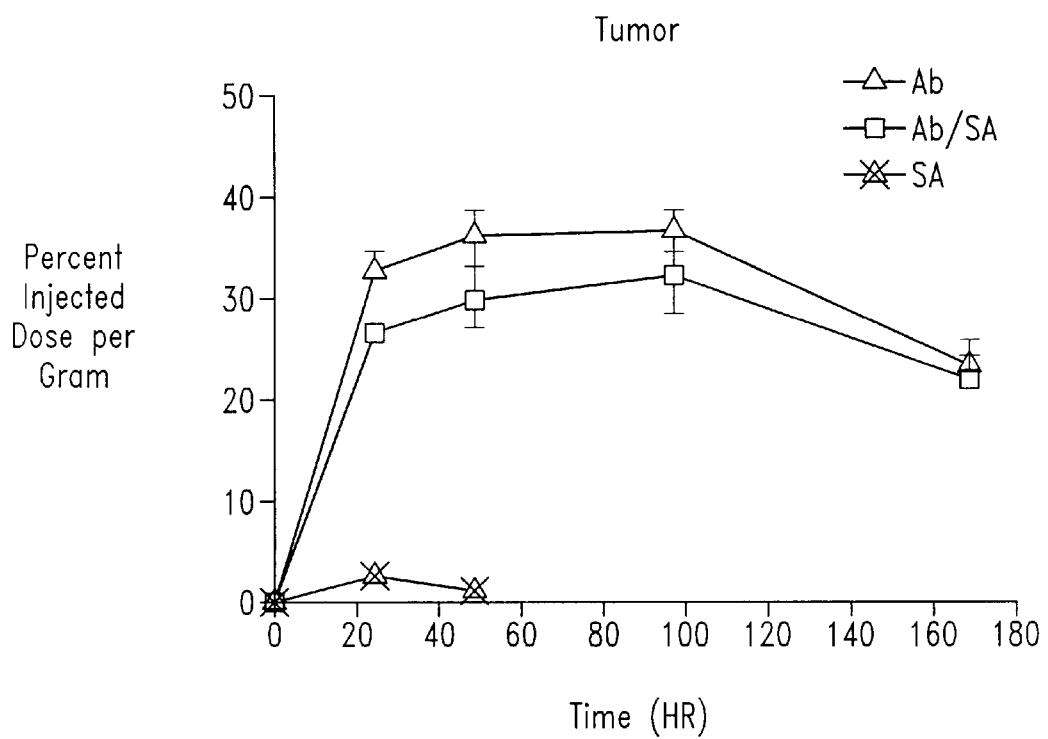
FIG. 1 illustrates the tumor uptake profile of antibody-streptavidin conjugate (Ab/SA) and control profiles of native whole antibody (Ab) and streptavidin (SA).
Figure 2A:
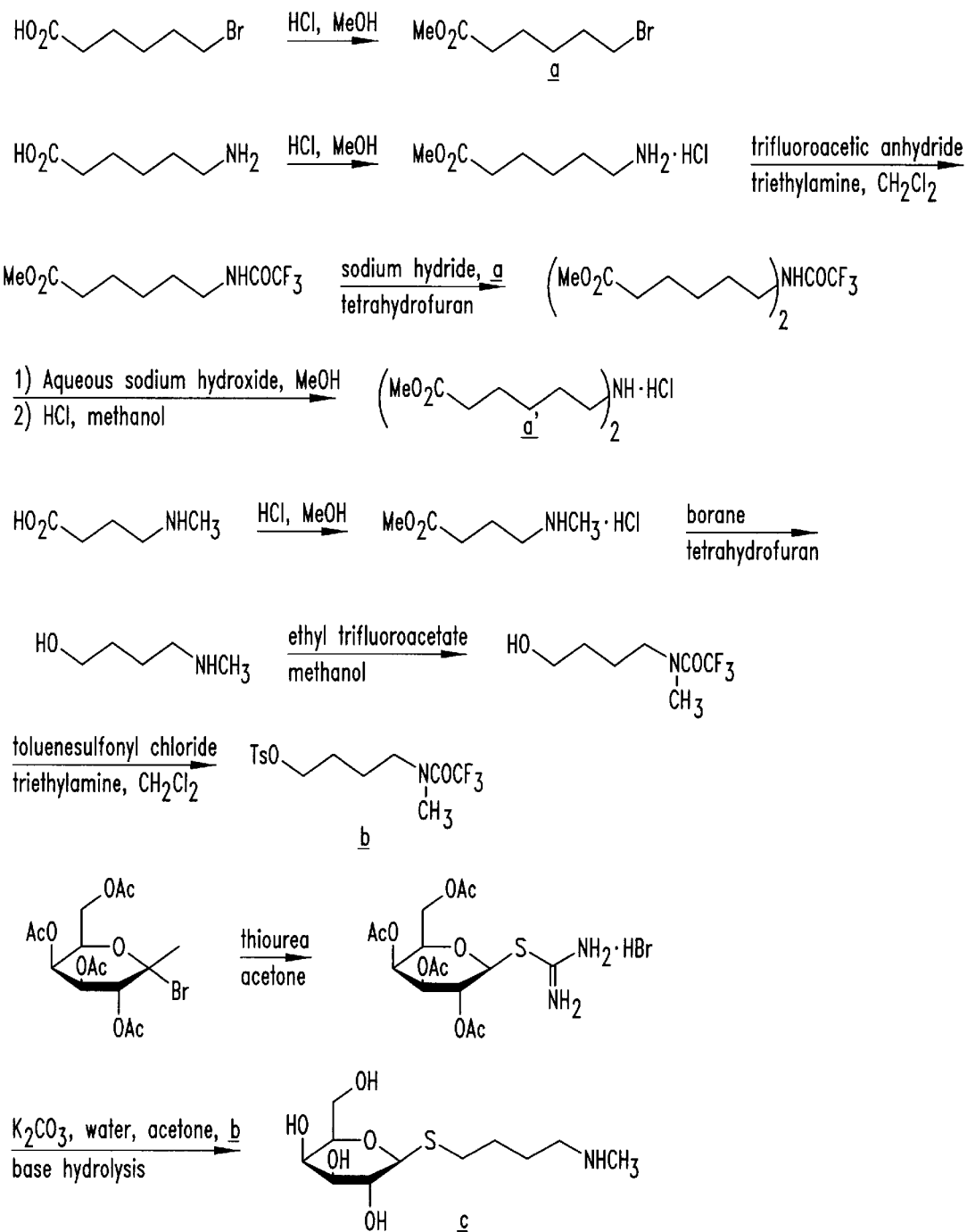
FIGS. 2a, 2b and 2c schematically depict the preparation of a sixteen galactose cluster-biotin CCA.
Figure 2B:
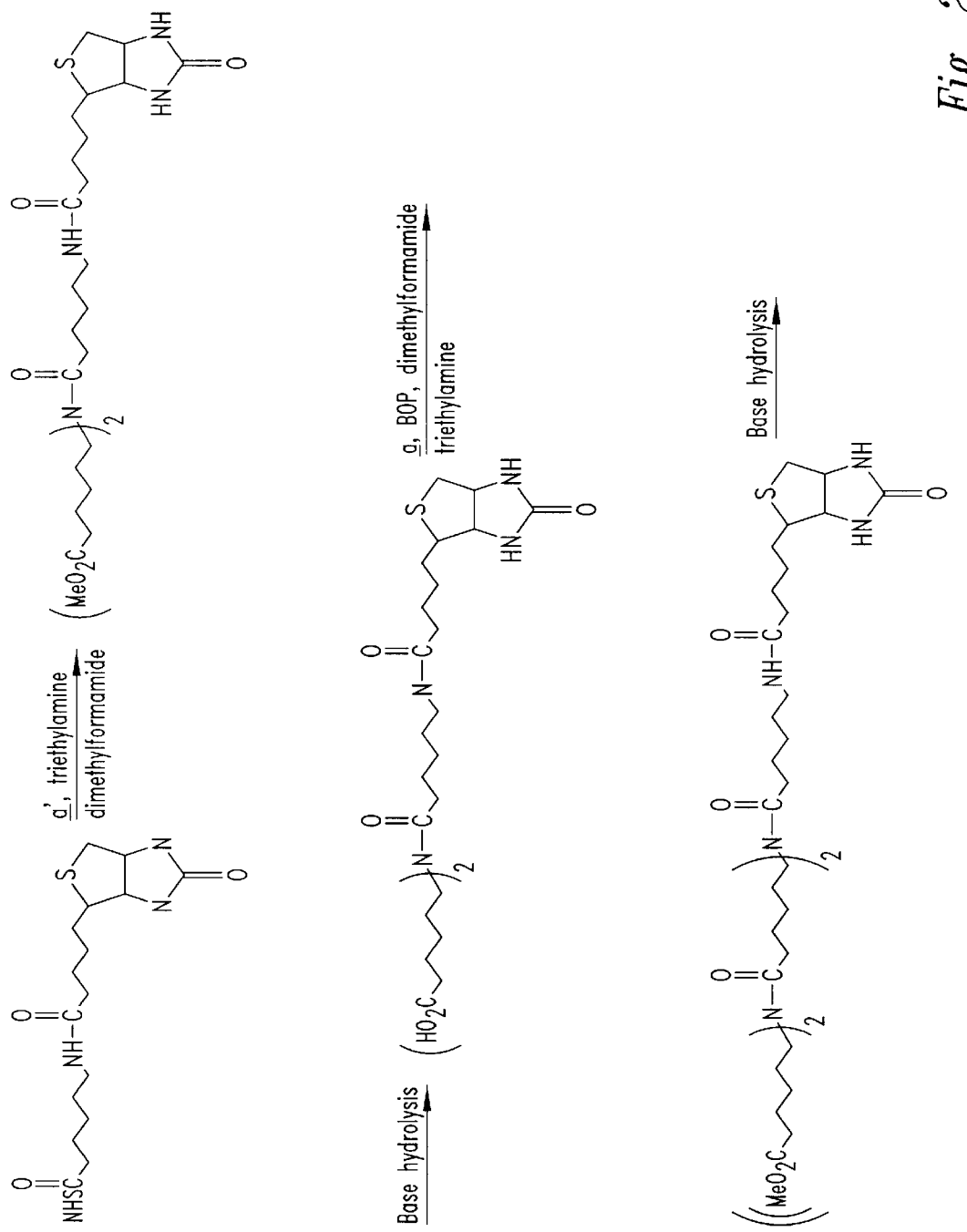
Figure 2B:
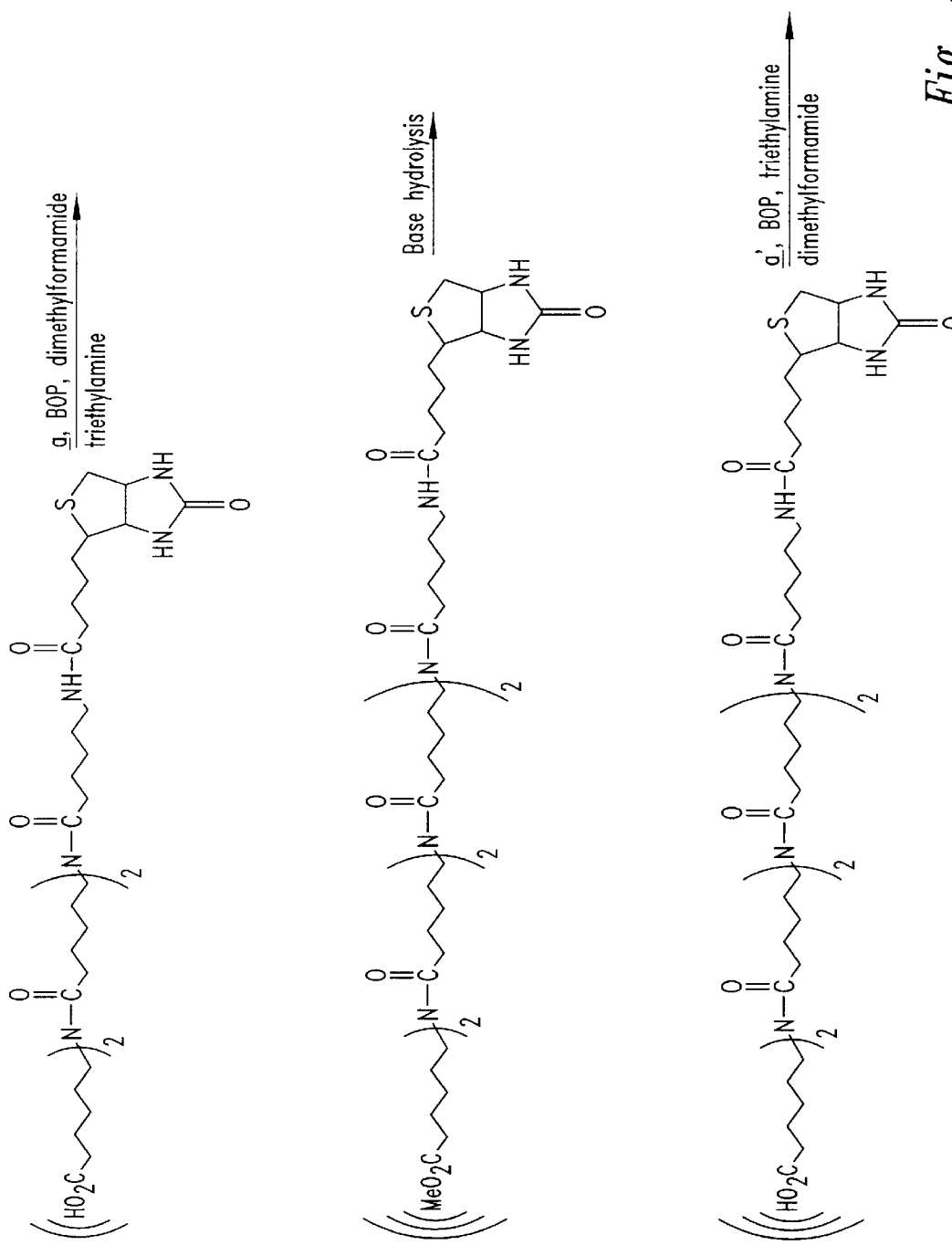
Figure 2C:
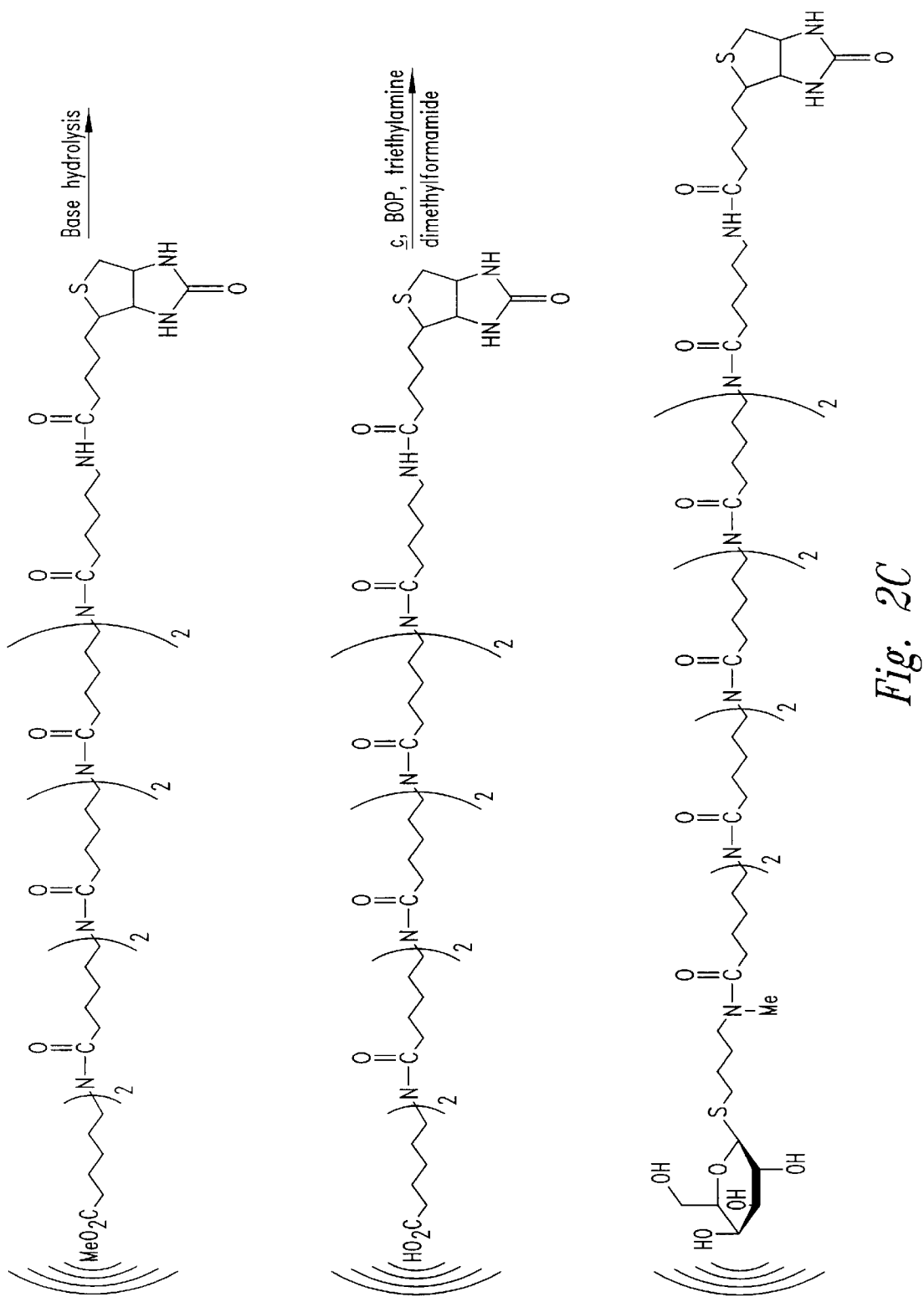
Figure 3A:
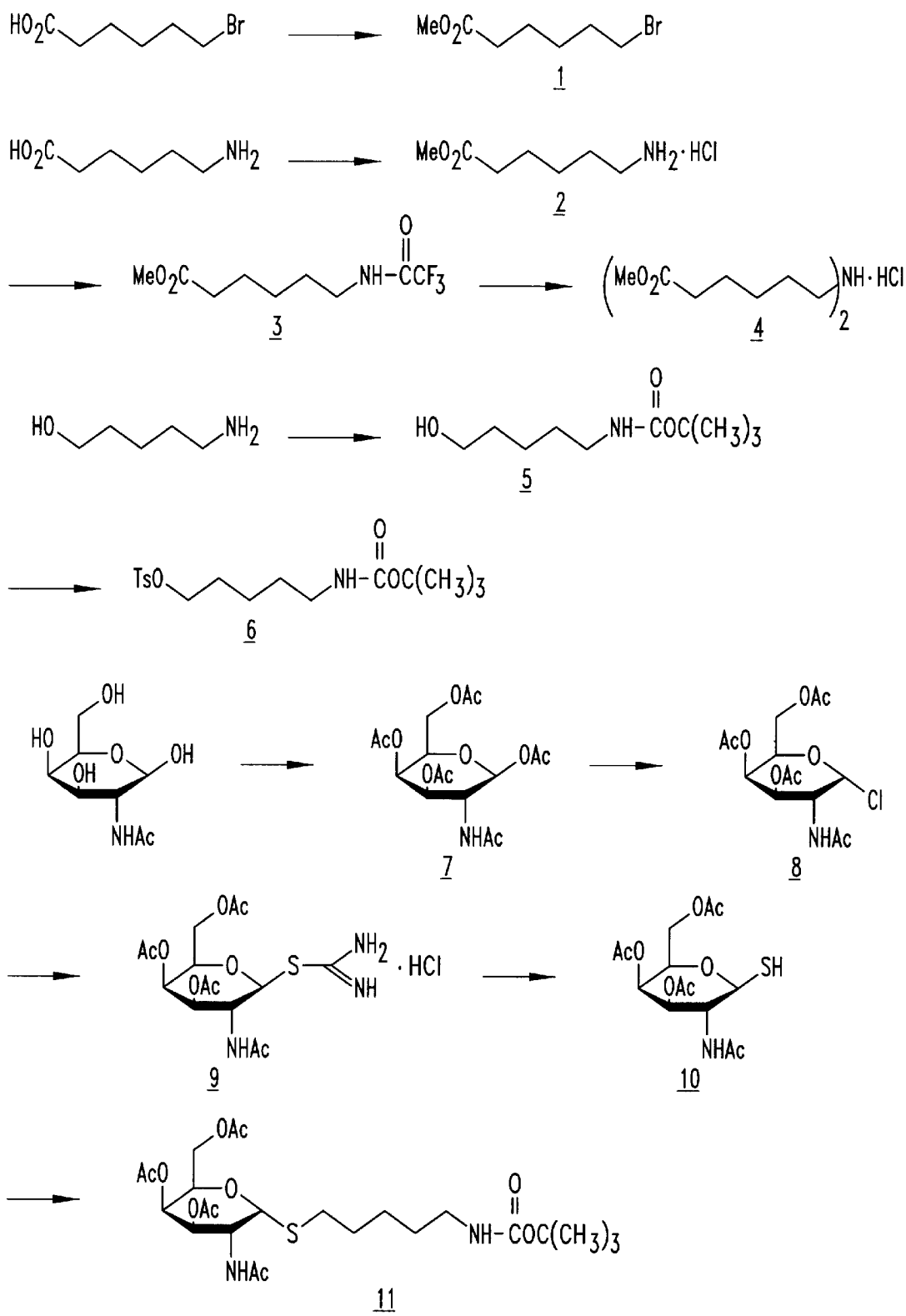
FIGS. 3a, 3b, 3c, 3d and 3e schematically depict the preparation of a sixteen N-acetyl-galactosamine (alpha-S) cluster-biotin CCA (compound 25).
Figure 3B:
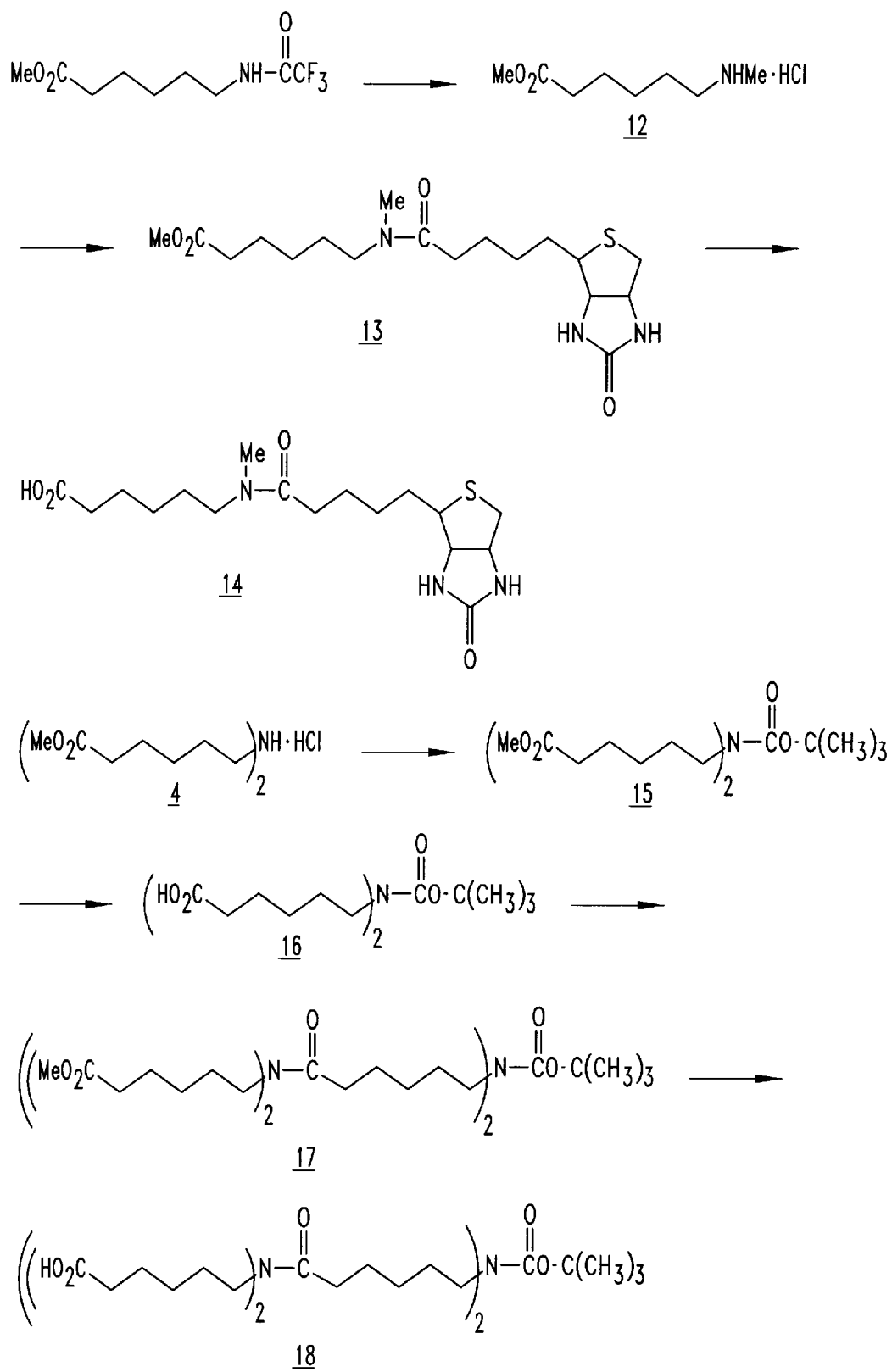
Figure 3C:
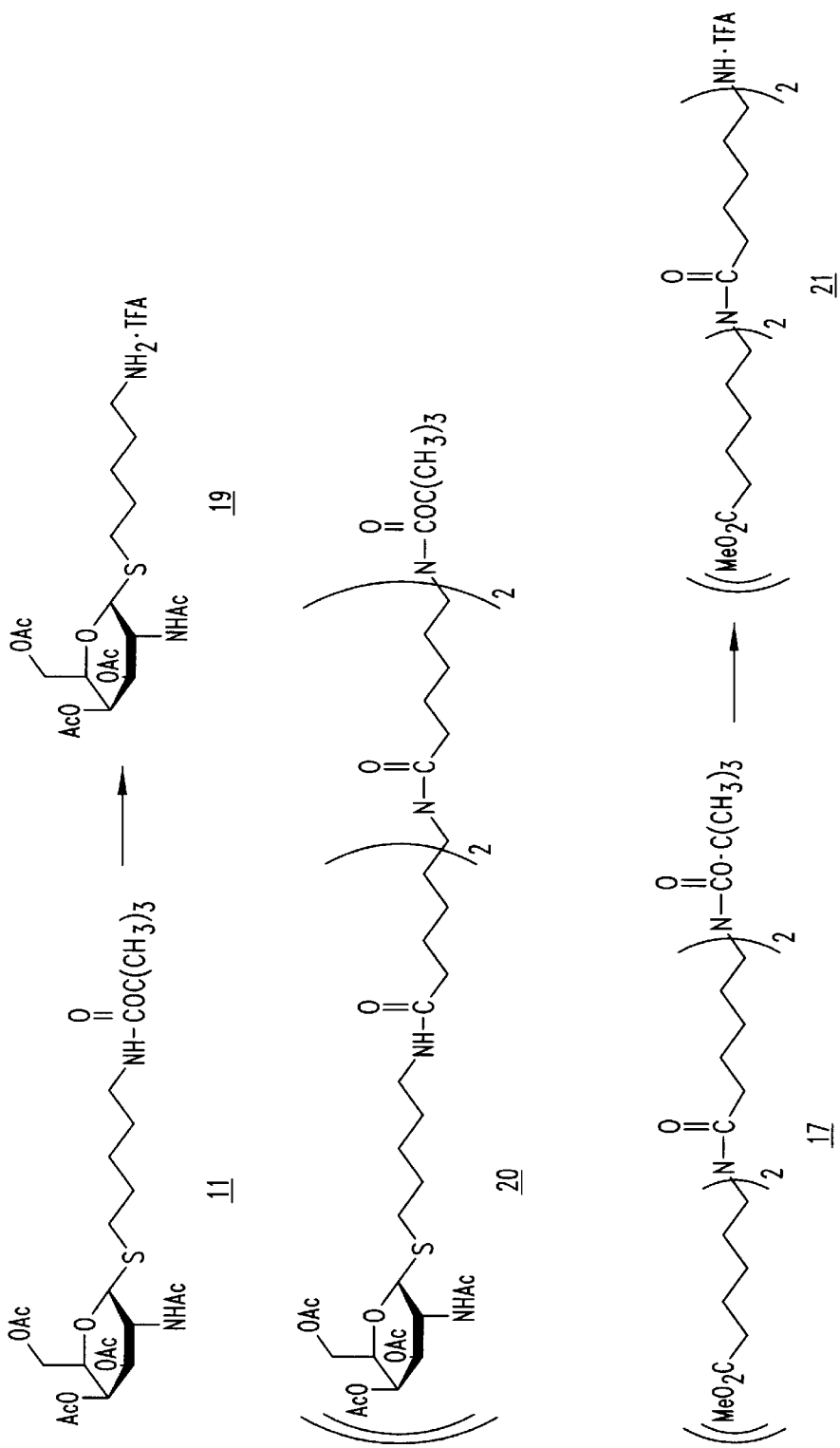
Figure 3D:
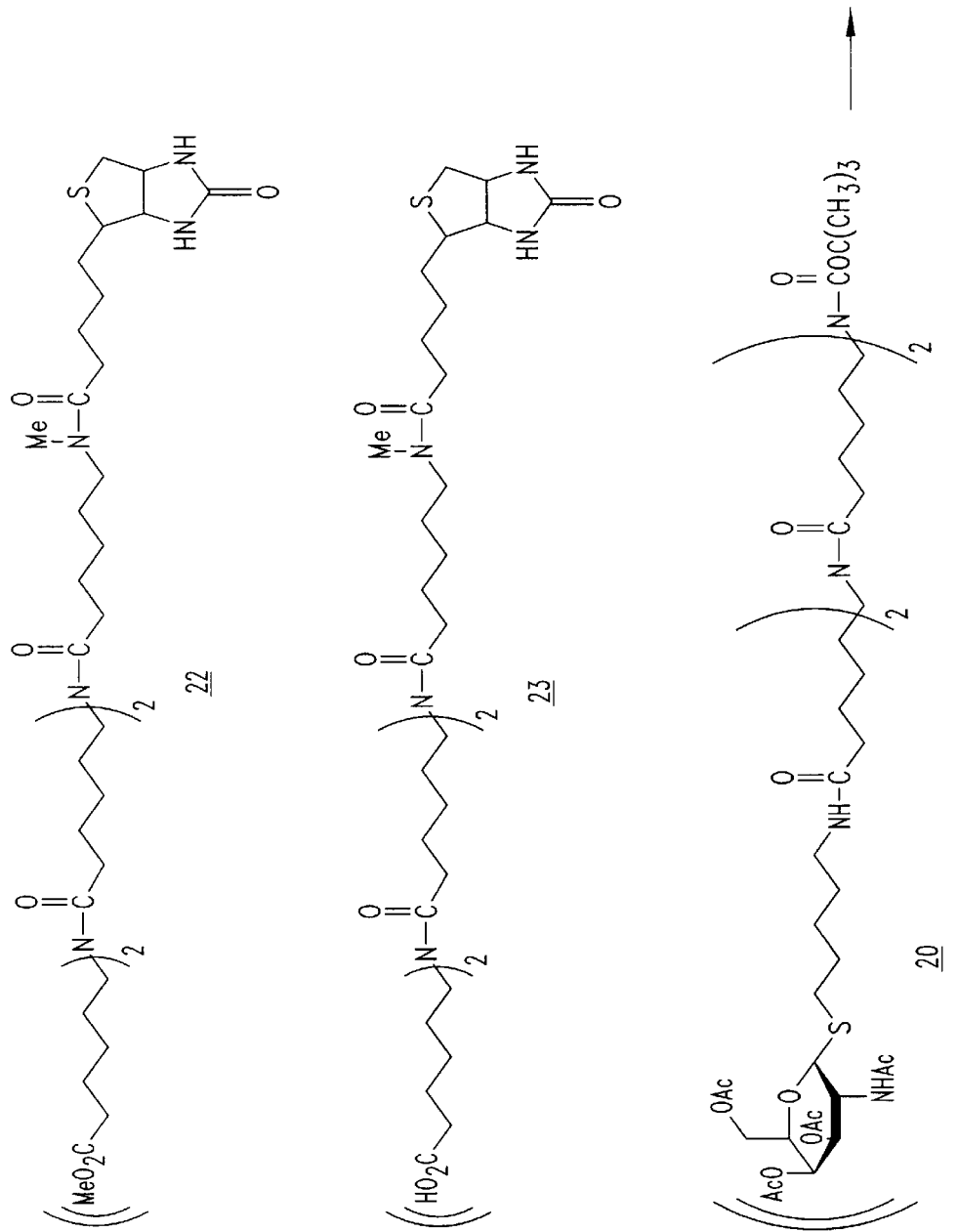
Figure 3E:
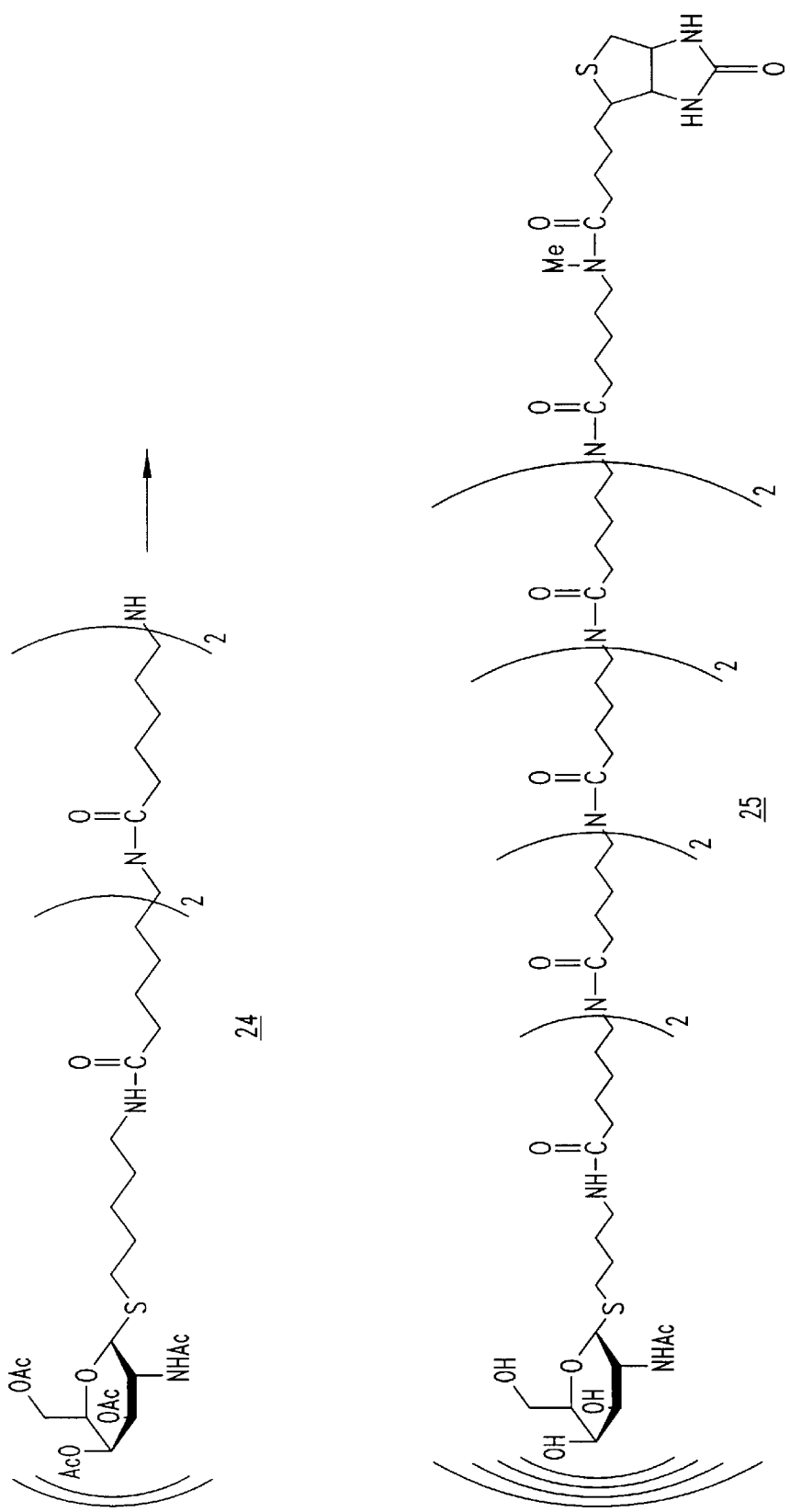
Figure 4:
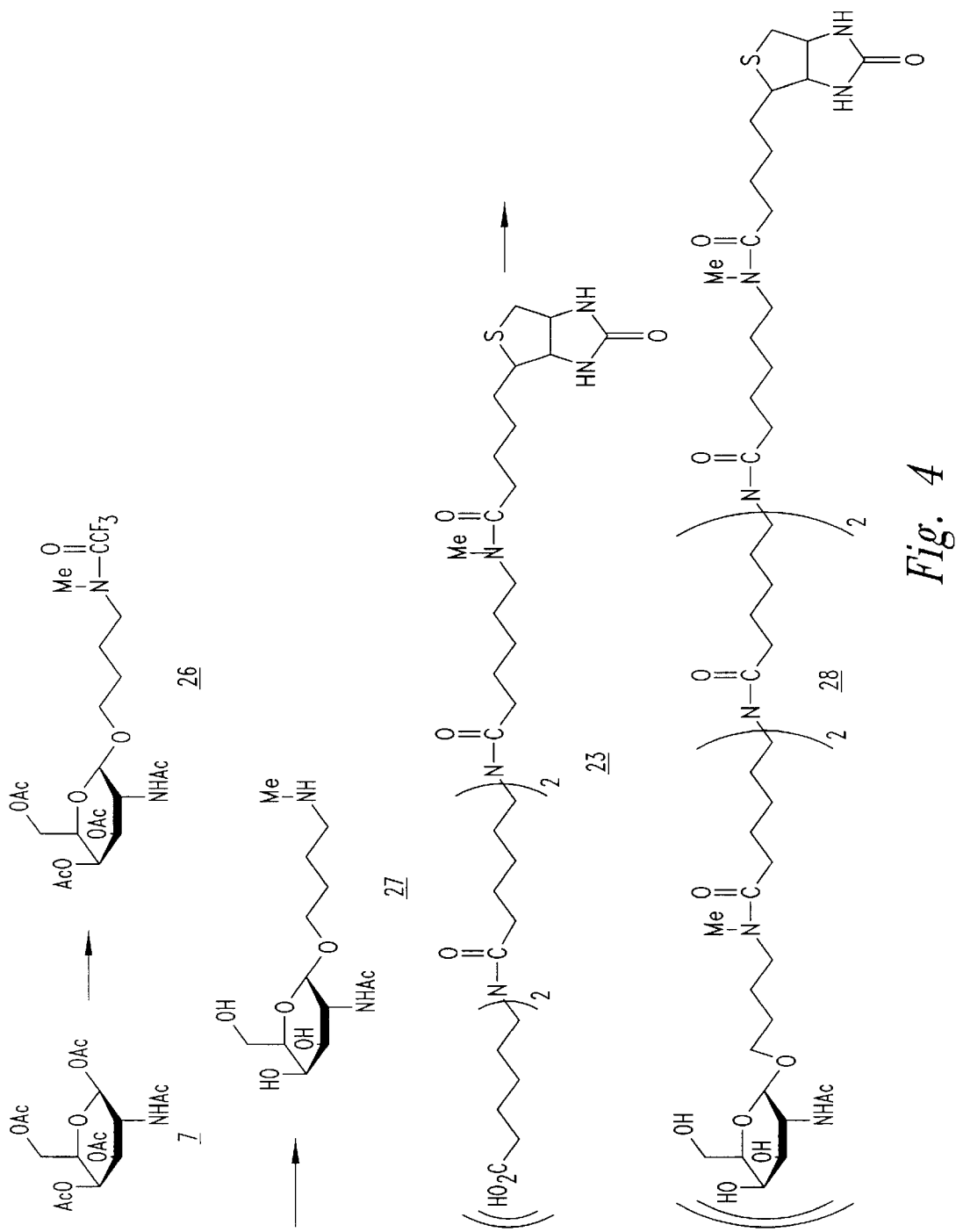
FIG. 4 schematically depicts the preparation of a four N-acetyl-galactosamine (alpha-O) cluster-biotin CCA (compound 28).
Figure 5:
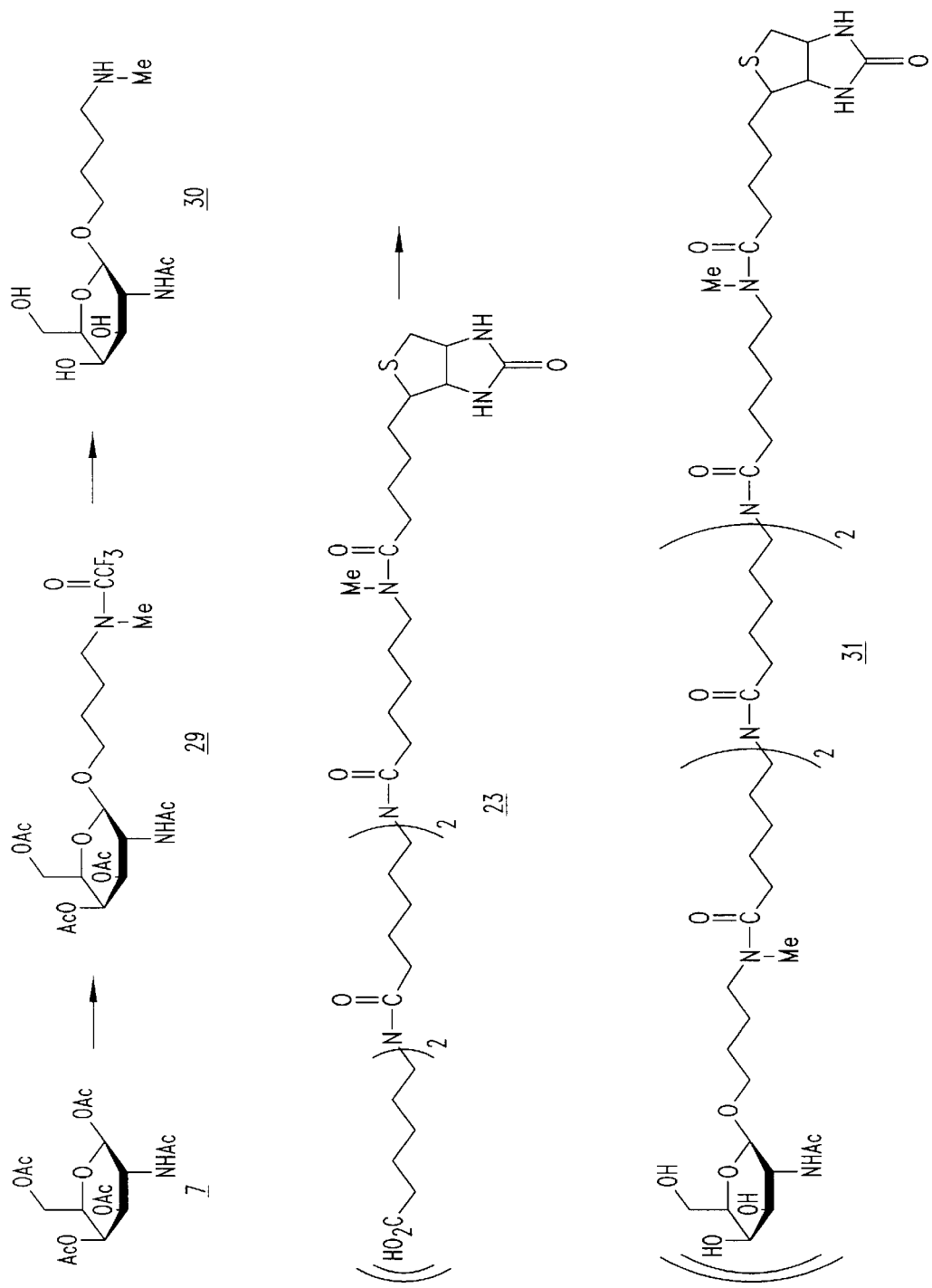
FIG. 5 schematically depicts the preparation of a four n-acetyl-galactosamine (beta-O) cluster-biotin CCA (compound 31).
Figure 6:
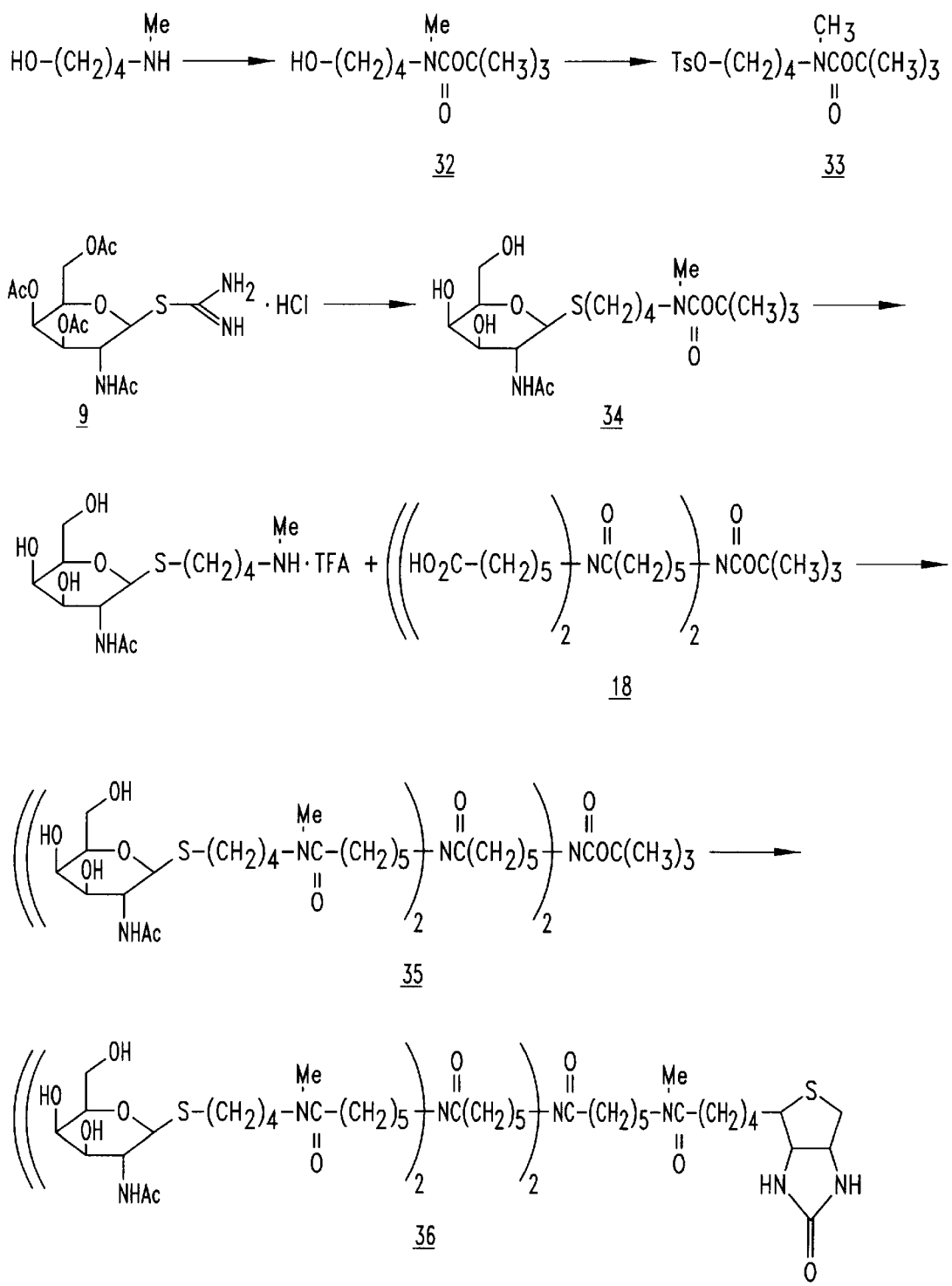
FIG. 6 schematically depicts the preparation of a four N-acetyl-galactosamine (beta-S) cluster-biotin CCA (compound 36).
Figure 7:
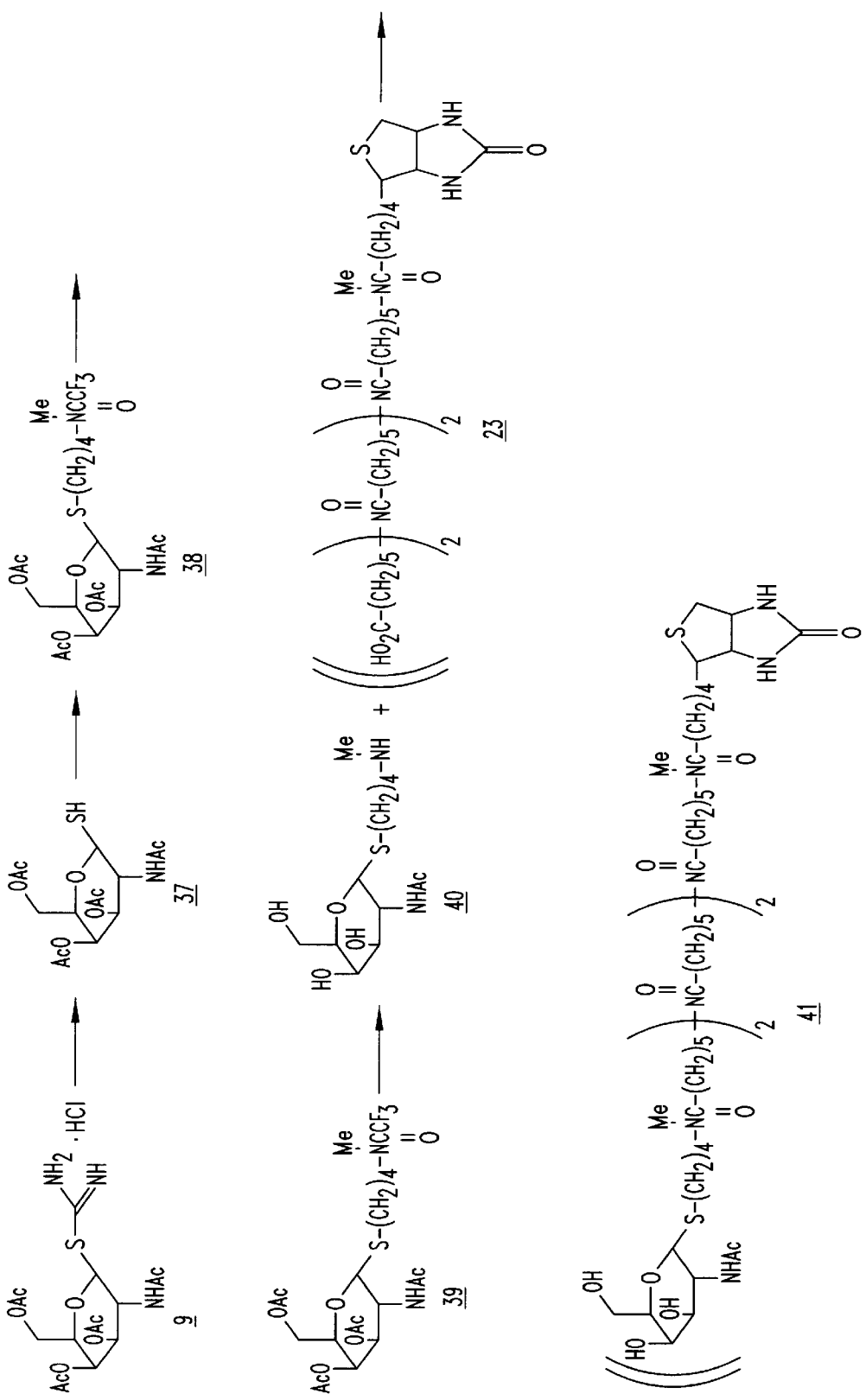
FIG. 7 schematically depicts the preparation of a four N-acetyl-galactosamine (alpha-S) cluster-biotin CCA (compound 41).

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, lectin/carbohydrate, ligand/receptor, S-protein/S-peptide, head activator protein (which binds to itself), cystatin-C/cathepsin B, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and is multivalent to bind a greater number of ligands. Univalent anti-ligands are also contemplated by the present invention. Anti-ligands of the present invention may exhibit or be derivatized to exhibit structural features that direct the uptake thereof, e.g., galactose residues that direct liver uptake. Avidin and streptavidin are used herein as prototypical anti-ligands.

Avidin: As defined herein, "avidin" includes avidin, streptavidin and derivatives and analogs thereof that are capable of high affinity, multivalent or univalent binding of biotin.

Ligand: As defined herein, a "ligand" is a relatively small, soluble molecule that binds with high affinity by anti-ligand and preferably exhibits rapid serum, blood and/or whole body clearance with administered intravenously in an animal or human. Biotin constructs are used as prototypical ligands.

Lower Affinity Ligand or Lower Affinity Anti-Ligand: A ligand or anti-ligand that binds to its complementary ligand-and-ligand pair member with an affinity that is less than the affinity with which native ligand or anti-ligand binds the complementary member. Preferably, lower affinity ligands and anti-ligands exhibit between from about $10^{-6}$ to $10^{-10}$M binding affinity for the native form of the complementary anti-ligand or ligand. For avidin/streptavidin and other extremely high affinity binding molecules, however, lower affinity may range between $10^{-6}$ to $10^{-13}$M. Lower affinity ligands and anti-ligands may be employed in clearing agents of the present invention.

Active Agent: A diagnostic or therapeutic agent ("the payload"), including radionuclides, drugs, anti-tumor agents, toxins and the like. Radionuclide therapeutic agents are used as prototypical active agent. Attachment of such radionuclide active agents to other moieties, either directly or via chelaton technology, may be accomplished as described herein or as known in the art.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Clearing Agent: An agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, reduced affinity, configuration or a combination thereof, that limit clearing agent access to the population of target cells recognized by a targeting moiety used in the same treatment protocol as the clearing agent.

Conjugate: A conjugate encompasses chemical conjugates (covalently or non-covalently bound), fusion proteins and the like.

Cluster Clearing Agent (CCA): A moiety capable of directing the clearance of a moiety to which it is bound upon administration or of a component to which it becomes associated with in vivo. CCAs of the present invention direct clearance via a hepatic pathway. Preferred CCAs of the present invention are characterized by a cluster hepatic clearance directing moiety and a binding moiety such as a ligand, an anti-ligand or a lower affinity derivative thereof. Preferred cluster hepatic clearance directing moieties are attached to the binding moiety via a single point of attachment.

Cluster Hepatic Clearance Directing Moiety: A plurality of sugar residues preferably arranged in a branched configuration along a cluster backbone in a manner in which the sugar residues are recognized by a hepatocyte receptor. Hepatic clearance directing moieties preferably contain from 3 to about 100 sugar residues, with from 3 to about 50 sugar residues preferred. Preferably, he branching network consists of two or three pronged branches, i.e., consists of 2, 4, 8, 16, 32 or 64 sugar residues or consists of 3, 9, 27, or 81 sugar residues. Two branched structures with 8, 16 or 32 sugar residues are more preferred as cluster hepatic clearance directing moieties of the present invention.

Cluster Backbone: A chemical framework to which sugar residues are bound. Preferably, the cluster backbone is formed of repetitive bifunctional units configured in a two or three pronged branching arrangement. Preferably he branching structure is iterative, such that 2-pronged units form 4, 8, 16, 32, etc, hexose bearing CCAs and 3-pronged units form 9, 27, 81, etc. hexose bearing CCAs. Aminocaproyl (HOOC—$(CH_2)_5$—$NH_2$) units are set forth herein as prototypical building blocks of cluster backbones, wherein the nitrogen atom provides the two-pronged attachment with the hydrogen atoms displaced by the formation of amide bonds. Other moieties useful as cluster backbone components are those bearing trivalent, tetravalent or higher valency atoms. The cluster is formed by derivatization of the available site son such trivalent, tetravalent or higher valency atoms. For example, nitrogen is trivalent, and therefore iterative, two-branched CCAs can be constructed with nitrogen bearing moieties, such as HOOC—$(CH_2)_n$—$NH_2$, wherein n is between from about 3 and about 8, heterobifunctional PEG structures, such as HOOC—$CH_2$—$(O(CH_2)_2)_n O(CH_2)_2$—$NH_2$, HOOC—$(CH_2)_2$—$(O(CH_2)_2)_n O(CH_2)_2$—$NH_2$ where n ranges from 1 to 5, and the like. Carbon is tetravalent, and therefore iterative, three-branched CCAs can be constructed with carbon bearing moieties, such as that described herein. Alternative base atoms and cluster backbone structures can be used, and skilled chemists are capable of identifying and synthesizing appropriate structures.

Binding Moiety: A ligand, anti-ligand or other moiety capable of in vivo association with a previously administered molecule (bearing the complementary ligand or anti-ligand, for example) or with another toxic or potentially toxic molecule present in the recipient's circulation or extravascular fluid space via recognition by the binding moiety of an epitope associated with the previously administered moiety or with the toxic or potentially toxic molecule.

The CCAs of the present invention are preferably employed in pretargeting protocols. "Two-step" pretargeting procedures feature targeting moiety-ligand or targeting moiety-anti-ligand (targeting moiety-receptor) administration, followed by administration of active agent conjugated to the opposite member of the ligand-anti-ligand pair. As step "1.5" in the two-step pretargeting methods of the present invention, a CCA is administered to facilitate the clearance of circulating targeting moiety-receptor conjugate.

In the two-step pretargeting approach, the clearing agent preferably does not become bound to the target cell population, either directly or through the previously administered and target cell bound targeting moiety-anti-ligand or targeting moiety-ligand ligand conjugate. An example of two-step pretargeting involves the use of biotinylated human transferrin as a clearing agent for avidin-targeting moiety conjugate, wherein the size of the clearing agent results in liver clearance of transferrin-biotin-circulating avidin-targeting moiety complexes and substantially precludes association with the avidin-targeting moiety conjugates bound at target cell sits. (See, Goodwin, D. A. , *Antibod. Immunoconj. Radiopharm.*, 4:427–34, 1991).

CCAs of the present invention contain a cluster hepatic clearance directing moiety and a binding moiety. Thus, CCAs of the present invention are bispecific in that the cluster hepatic clearance directing moiety mediates binding with the molecule to be cleared. These bispecific CCAs are capable of in vivo binding or association with molecules to be cleared and interaction with hepatic receptors to effect clearance of CCA-containing constructs by that route. Preferred CCAs of the present invention are suitable for use as a clearing agent in pretargeting protocols, including two step protocols.

Clearing agents useful in the practice of the present invention preferably exhibit one or more of the following characteristics:

rapid, efficient complexation with serum-associated targeting moiety-ligand (or anti-ligand) conjugate in vivo;

rapid clearance from the blood of serum-associated targeting moiety conjugate capable of binding a subsequently administered complementary anti-ligand or ligand containing molecule;

high capacity for clearing (or inactivating) large amounts of serum-associated targeting moiety conjugate; and low immunogenicity.

Clearing agents previously developed by the assignee of this patent application, incorporated human serum albumin (HSA), a plurality of hexoses and a plurality of ligands, as follows:

(Hexose)$_m$—Human Serum Albumin (HSA)—(Ligand)$_n$, wherein n is an integer from 1 to about 10 and m is an integer from 1 to about 45 and wherein the hexose is recognized by a liver receptor (e.g., Ashwell receptors).

The exposed hexose residues direct the clearing agent to rapid clearance by endocytosis into the liver through specific receptors therefor. These receptors bind the clearing agent or clearing agent-containing complexes, and induce endocytosis into the hepatocyte, leading to fusion with a lysosome and recycle of the receptor back to the cell surface. This clearance mechanism is characterized by high efficiency, high capacity and rapid kinetics. The rapid kinetics of hexose-mediated liver uptake, coupled with a relatively high affinity interaction between the binding moiety, such as a ligand, and the compound to be cleared, provide for rapid and efficient clearance, facilitating the use of intermediate or low molecular weight clearing agents such as the CCAs of the present invention.

CCAs of the present invention are designed to meet the four criteria set forth above as well. Three additional performance criteria were instituted for CCAs:

metabolic stability in at least one of the following physiological environments, serum, urine and liver;

low ability to compromise pretargeted receptor; and chemically defined structure.

Preferred CCAs may be characterized as small molecule clearing agents with regard to molecular weight (less than about 20,000 daltons) and structural homogeneity. More preferred CCAs or small molecule clearing agents, composed of biotin or a lower affinity biotin analog and a branched multi-sugar residue cluster hepatic clearance directing moiety, have utility for the clearance of streptavidin- or avidin-targeting moiety conjugates from non-target sites, e.g., the circulation, extravascular space, etc.

Other embodiments of the present invention involve the preparation and use of CCAs in clearance of other previously administered molecules or toxic or potentially toxic molecules generated in vivo, which compounds to be cleared are present in a patient's circulation or extravascular fluid space. Previously administered molecules may include active agent-containing conjugates (e.g., radionuclide-chelate-antibody which can be cleared by a CCA containing an anti-chelate or anti-antibody binding moiety; or radionuclide-chelate-antibody-biotin binding protein which can be cleared by a biotin-containing CCA); targeting moiety-receptor conjugates; or the like.

Preferred CCAs of the present invention are administered, permeate the circulation and penetrate the extravascular fluid space. Consequently, previously administered compounds or toxic or potentially toxic moieties that are present in the circulation or in the extravascular fluid space are accessible to the CCAs of the present invention. Circulating compounds are removed via association with the CCA and processing by liver receptors. Previously administered compounds or toxic or potentially toxic moieties, present in extravascular fluid space but not associated with a target cell or epitope, are removed via liver receptors as such compounds diffuse back into the circulation in association with CCAs.

CCA bound to a pretargeted agent (targeting moiety-anti-ligand conjugate, for example) dissociates and reassociates over time. Following dissociation and prior to reassociation, the pretargeted agent is available for binding to active agent-containing constructs. Binding of such active agent-containing constructs is expected to be favored due to a concentration gradient (i.e., higher concentration of active agent-containing construct than target-associated CCA). Another CCA embodiment of the present invention exhibits a favorable biodistribution which avoids such compromise of pretargeted receptor via direct receptor-CCA or CCA metabolite association. A preferred alternative CCA embodiment of the present invention incorporates a lower affinity binding moiety, which can be more easily replaced at the pretargeted receptor by subsequently administered active agent-higher affinity binding moiety construct.

Toxic or potentially toxic molecules that may be removed from a recipient's circulation or extravascular fluid space include: chemotherapeutics e.g., alkylators, heavy metals and the like. Binding moieties capable of associating with toxic or potentially toxic molecules present in the recipient's circulation or extravascular fluid space include antibodies or fragments thereof directed to epitopes that are characteristic of such toxin or potential toxin. Other useful binding moieties include oligonucleotides, ligands or anti-ligands.

Characteristics of useful binding moieties are discussed below. The binding between the binding moiety of the CCAs of the present invention and the molecule to be cleared from the circulation or extravascular fluid space need only be transient, i.e., exists for a sufficient amount of time to clear the molecule from circulation or extravascular fluid space to the liver. Also, it should be noted that the binding constant of the binding component is determined with regard to the CCA as a whole. That is, a biotin-containing CCA is expected to bind to avidin or streptavidin with a binding constant less than that of biotin itself. Experimentation has revealed that biotin-containing CCAs of the present invention are capable of clearance.

In general, the binding constant characterizing the interaction of the binding moiety of the CCA and the molecule to be bound thereby should be low enough to keep short the residence time of any CCA accreting to target sites. Also, the binding constant must be sufficiently high to capture the molecule to be bound and traffic that molecule to the liver. Consequently, CCA binding moieties having a binding constant in excess of about $10^8$ are preferred.

Binding moieties of the present invention include ligands, anti-ligands, and other target epitope-recognizing moieties. One skilled in the art can substitute acceptable moieties for the binding moieties discussed specifically herein. Preferred binding moieties are characterized by a molecular weight of a Fab fragment of a monoclonal antibody or lower. Such binding moieties may also be modified to include suitable functional groups to allow for attachment of other molecules of interest, e.g., peptides, proteins, nucleotides, and other small molecules.

Lower molecular weight bispecific CCA molecules, designed to contain appropriately spaced hexoses and biotin, when formulated, quickly cleared streptavidin-containing conjugate from circulation. Examples of such biotin-containing CCAs are set forth below.

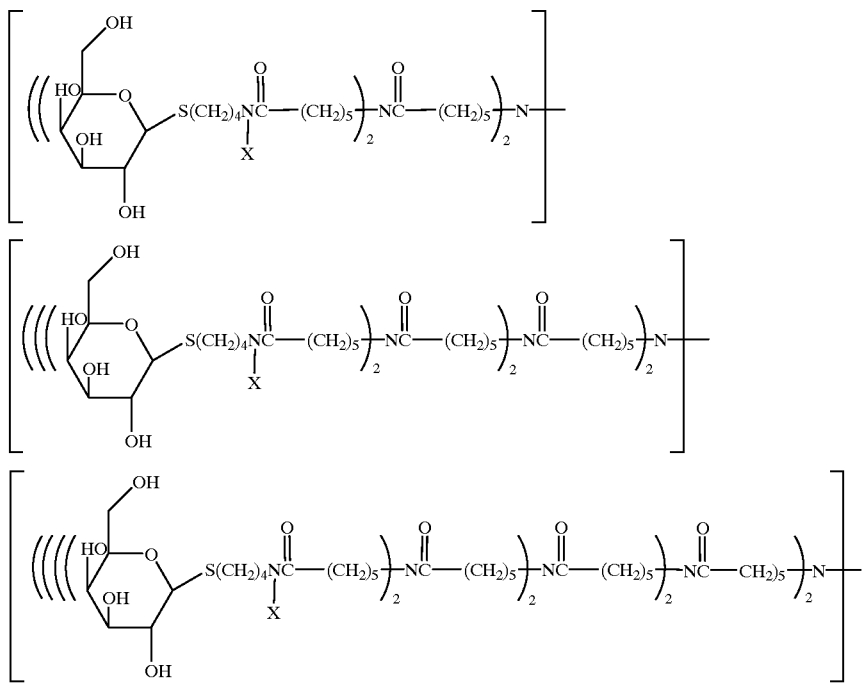

where X is H, methyl, lower alkyl or lower alkyl with heteroatoms. The term lower alkyl refers to moieties of straight or branched construction having from 1 to about 10 carbon atoms, with from 1 to about 6 carbon atoms preferred. The term herteroatom refers to sulfur, oxygen or nitrogen. The above structures bear 4, 8 and 16 galactose residues respectively. Further iteration in the branching allows expansion to include 32, 64, etc., galactose residues.

CCAs of the present invention are designed to interact with hepatic receptors to facilitate clearance of CCA-containing constructs via that route. Hepatocyte receptors which provide for effective clearance include in particular Ashwell receptors, mannose receptors associated with endothelial cells and/or Kupffer cells of the liver, the mannose 6-phosphate receptor, and the like. Hexoses which may be employed in the CCA structure include by way of example galactose, mannose, mannose 6-phosphate, N-acetylgalactosamine, pentamannosyl-phosphate, and the like. Hexoses recognized by Ashwell receptors include glucose, galactose, galactosamine, N-acetylgalactosamine, pentamannosyl phosphate, amnnose-6-phosphate and thioglycosides of galactose, galactosides, galactosamine, N-acetylgalactosamine, and mannosyl-6-phosphate and the like. A sufficient number of hexose residues are attached to biotin or to the selected biotin analog to provide for effective clearance, e.g., via the Ashwell receptors located on the surface of hepatocytes.

Preferably, CCAs are of a low enough molecular weight to provide for efficient diffusion into the extravascular space, thus providing for binding to both circulating and non-circulating conjugate. This molecular weight will preferably range from about 1,000 to about 20,000 daltons, more preferably about 2,000 to 16,000 daltons.

Preferable cluster hepatic clearance directing moieties of CCAs of the present invention are characterized by at least 3 hexose residues, e.g., glactose residue or N-acetylgalactosmaine residues. However, the invention is not limited thereby and embraces the attachment of any number of hexose residues or mixture thereof which results in an efficacious bispecific CCA.

The design of the cluster hepatic clearance directing component of the CCA, containing a hexose such as galactose or N-acetylgalactosamine, also depends upon a number of factors including:

(i) The number of hexose residues, e.g., galactose or N-acetylgalactosamine residues:

The literature suggests that galactose receptors are grouped on the surface of human hepatocytes as heterotrimers and possible bis-heterotrimers. Thus, for optimal affinity, the CCA should possess at least three galactose residues, and preferably more, to provide for "galactose clusters." In general, the CCA will contain from about 3 to about 50 galactose residues, preferably from about 3 to 32, and most preferably 16 galactose residues.

(ii) Distance between hexose residues:

Each galactose receptor is separated by a distance of 15, 22 and 25 Å. Thus, the galactose residues within each CCA should preferably be separated by a flexible linker which provides for a separation distance of at least 25 Å, to enable the sugars to be separated by at least that distance. It is expected that this minimum spacing will be more significant as the number of sugar residues, e.g., galactoses, are decreased. This is because larger number of galactoses will likely contain an appropriate spacing between sugars that are not immediately adjacent to one another, thus providing for the desired receptor interaction.

Assuming an average bond length of about 1.5 Å, this would mean that the sugar residues should ideally be separated by a spacer of not less than about 10 bond lengths, with at least 25 bond lengths being more preferred.

For example, galactoses or other sugar residues may be attached in a branched arrangement as follows, which is based on bis-homotris:

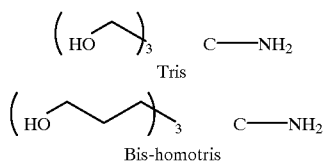

Preferably, each arm is extended, and terminates in a carboxylic acid terminus as follows:

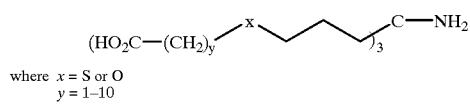

where $x$ = S or O
$y$ = 1–10

Exemplary clearing agents having such an arrangement are set forth below:

(iii) Distance between the cluster hepatic clearance directing moiety and the binding moiety of the CCA.

If many galactose or other sugar residues are linked to the biotin species, then the linker should be long enough to alleviate adverse steric effects which may result in diminished binding of the CCA to the molecule to be cleared and/or diminished binding of the complex to the hepatocyte receptor.

While the following parameters appear to be optimal for galactose it should be noted that these factors may vary with other hexoses or mixtures thereof, which may or may not bind to the same receptors, or may bind differently. For example, the inventors have now conducted a series of experiments and developed a second generation of CCAs based upon the hexosse N-acetylgalactosamine. In this development effort, the three design parameters discussed above were re-evaluated and additional design parameters were investigated.

With regard to criteria (i), the number of hexose residues, it was discovered that a smaller number of

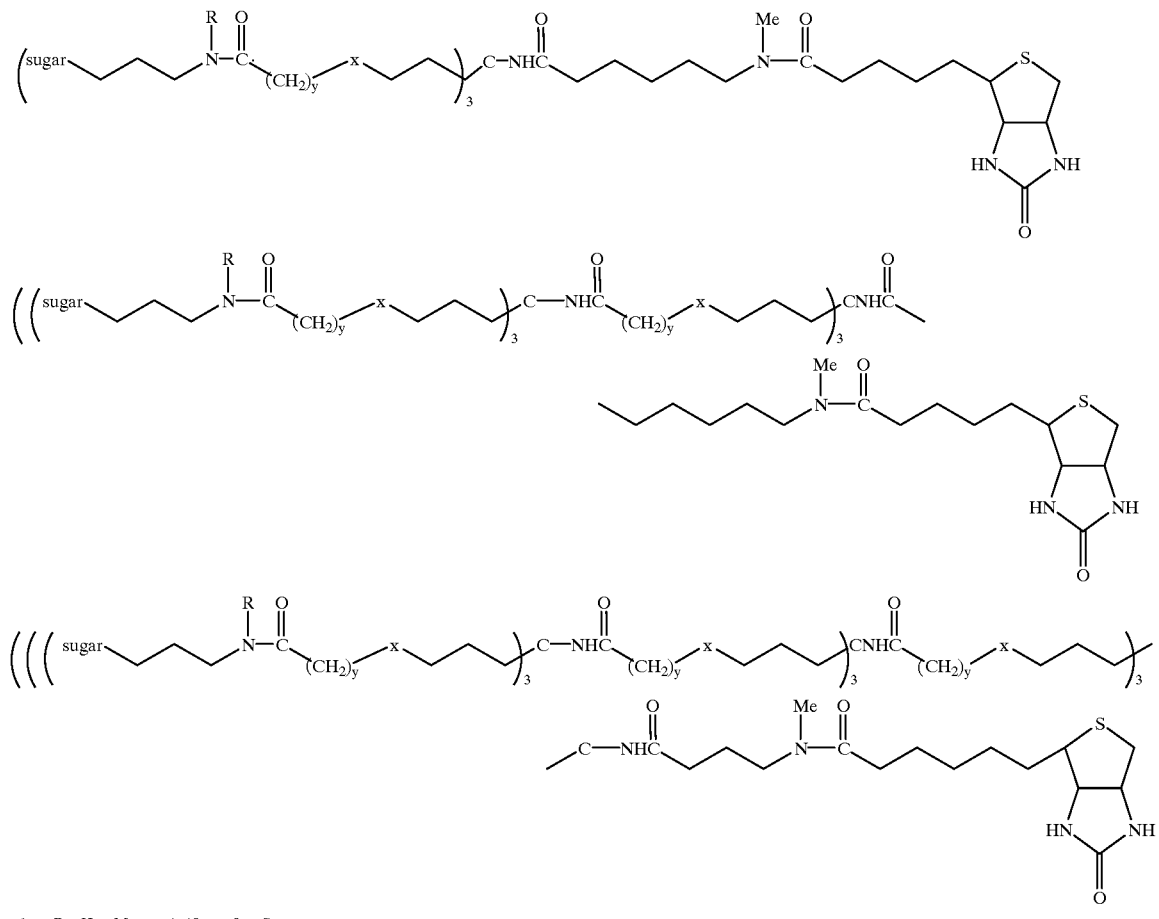

where R = H or Me; $y$ = 1–10; $x$ = O or S

Such an arrangement, with 0, 1 or 2 branched iterations, allows for the incorporation of 3, 9 or 27 sugars. Other iterative structures may be based upon the constructs, such as Asp (bis-LAC AHT)$_2$, set forth by Lee et al., *Biochemistry*, 23:4255–4261, 1984.

N-acetylgalactosamine hexose residues can be employed to achieve equivalent levels of clearance of targeting moiety-receptor. It appears therefore that N-acetylgalactosamine exhibits higher affinity for the Ashwell receptor than galactose.

Regarding criteria (ii), the distance between hexose residues, it was discovered that an increase in distance between the sugar residue and the cluster backbone (from four carbons to five carbons) resulted in enhanced affinity for Ashwell receptors. This enhancement is believed to be the result of greater conformational flexibility. Further increases in that distance provided additional enhancement in affinity but adversely impacted the solubility of the resulting CCAs. Consequently, chemical modification of such extended CCAs to improve solubility may be necessary. Such chemical modifications are within the ordinary skill in the chemical arts.

With respect to criteria (iii), the distance between the cluster hepatic clearance directing moiety and the binding moiety, the use of an extender which is stabilized against metabolic degradation between those moieties provided the following advantages: (1) relief from steric hindrance impacting binding moiety association with the compound it is designed to clear; and (2) enhanced in vivo stability against formation of binding moiety-containing CCA metabolites. However, some steric hindrance may be advantageous with regard to biotin-containing CCAs, because binding thereof to pretargeted receptor will likely be reduced. Consequently, selection of optimal structure in this regard involves an analysis of the affinity required to clear versus the affinity displacement by non-sterically hindered biotin-active agent constructs.

As an extender between the binding moiety and the cluster hepatic clearance directing moiety, a bifunctional linker is employed which is preferably characterized by one or more of the following characteristics: flexibility, ability to access all binding sites available on the moiety to be cleared (e.g., targeting moiety-anti-ligand conjugate), metabolic stability and the like. One such linker incorporates a simple linear carbon chain between two functional groups, such as aminocaproate ($—CO—(CH_2)_5—NH—$). Alternatively, linear or branched carbon chains containing heteroatoms, polymeric moieties containing heteroatoms, and the like may be used to link two functional groups. One such extender is $—CO—(CH_2)_2—(O—(CH_2)_2—O)_n—(CH_2)_2—NX—$, wherein n ranges from 1 to about 20 and X is hydrogen or branched or straight chain lower alkyl of 1 to about 6 carbon atoms, phenyl, benzyl, or a 2 to about 6 carbon lower alkyl group substituted with a phenyl moiety. The extender may be generated using a polyethylene glycol polymer and affords the advantage of metabolic stability, increased aqueous solubility, increased access to the construct to be cleared and greater hydrodynamic extension. Also, alternative functional groups may be selected by a person of ordinary skill in the art to link the extender to the binding moiety and to the cluster hepatic clearance directing moiety. Alternative extenders include, polymers such as dextran, poly-D-amino acids (formed of lysine, glutamic acid or the like), poly-amino-phosphonates (e.g., based upon alpha-phosphonomethyl amino acid compounds, such as the following:

$$HOOC—CH(NH_2)CH_2—\overset{\overset{O}{\|}}{P}(OH)_2).$$

Non-polymeric molecules such as aminoalkylhalides, capable of forming an amide with biotin or other binding component and a tertiary amine with the hexose cluster, and the like, may also be used as extenders in the practice of the present invention.

Further structural/functional studies were conducted on the N-acetylgalactosamine second generation CCAs in an effort to design an optimal CCA. As a result of this effort, more preferred CCAs of the present invention are characterized by one or more of the following structural features.

(A) Unnatural orientation of ligand (e.g., (L)-biotin) and anti-ligand (e.g., streptavidin formed from (D)-amino acids) impart enhanced stability to metabolic degradation.

(B) Secondary amide bond between sugar residues and the cluster backbone appears to contribute to higher affinity sugar-Ashwell receptor binding.

(C) Appropriate orientation for sugar attachment appears to impact affinity, and appropriate linking heteroatom appears to impact stability and affinity. For an oxygen linking heteroatom, a 1-beta linkage is preferred for galactose-containing CCAs, while a 1-alpha linkage is preferred for N-acetylgalactosamine-containing CCAs. Overall, sulfur linkers are preferred (appear to improve stability), and 1-alpha-S linkers are most preferred for N-acetylgalactosamine-containing CCAs.

(D) Tertiary amine adjacent to the binding moiety, such as a ligand or an anti-ligand, enhances in vivo stability of the CCA.

Examples of specific embodiments of preferred CCAs of the present invention are shown below:

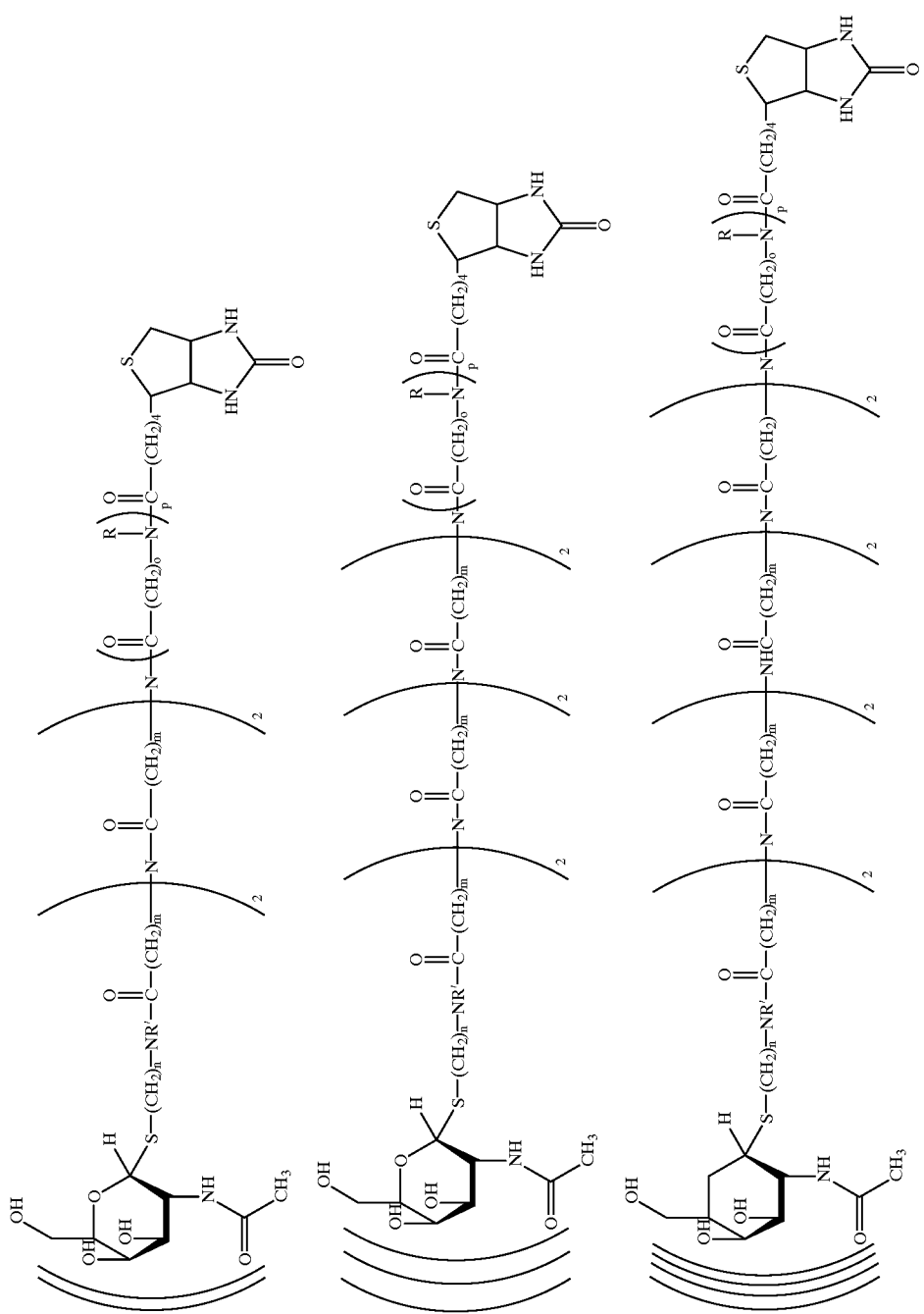

where n is an integer ranging from 1 to about 10, with from about 4 to about 8 preferred and with from about 4 to about 5 still more preferred; m is an integer ranging from about 3 to about 6, with 5 preferred; wherein o is an integer ranging from about 3 to about 6, with 5 preferred; p is an integer ranging from 1 to about 10, with from 1 to about 6 preferred and with from 1 to about 3 more preferred; and R is a straight or branched chain lower alkyl of from 1 to about 6 carbon atoms, phenyl, benzyl, or a 2 to about 6 carbon lower alkyl group substituted with a phenyl moiety.

At higher administered doses of CCA characterized by greater distance between the binding moiety (e.g., biotin) and the cluster hepatic clearance directing moiety, blockage of pretargeted receptor sites by the CCA is more likely. In this case, lower affinity biotin analogs may be employed as is more fully discussed below. An alternative way to diminish the affinity of the biotin ligand is to provide greater steric hindrance to biotin-avidin or biotin-streptavidin binding (in contrast to general bias for decreased steric hindrance as discussed above). On method to provide increased steric hindrance is by increasing the size, and therefore the steric impact, of the substituent used to form a tertiary amine on the amide nitrogen next adjacent to biotin in the CCA structure. For example, N-propyl, N-butyl, N-benzyl or like substitutions can be employed. Persons skilled in the art are familiar with substitutions of this type.

Given the teachings in this application one skilled in the art can, using available synthesis techniques, attach biotin to other hexose residues, or a mixture of different hexose residues via a cluster backbone and the ascertain those constructs which provide acceptable clearance.

Also, one skilled in the art can additionally substitute other complementary ligands for biotin, ideally those having small molecular weight. Such ligands may also be modified to include suitable functional groups to allow for the attachment of other molecules of interest, e.g., peptides, proteins, nucleotides, and other small molecules. Examples of suitable functional groups include, e.g., maleimides, activated esters, isocyanates, alkyul halides (e.g., iodoacetate), hydrazides, thiols, imidates and aldehydes.

In addition to the described therapeutic advantages of the described CCAs, they also afford cost, regulatory and safety advantages. The CCAs of the present invention are chemically well defined and therefore are amenable to relatively precise characterization. Also, such CCAs can be produced reproducible from readily available or easily synthesizable components.

One embodiment of the present invention provides CCAs having physical properties facilitating use for in vivo complexation and blood clearance of anti-ligand/ligand (e.g., avidin/biotin)-targeting moiety (e.g., antibody) conjugates. These CCAs are useful in improving the target:blood ratio of targeting moiety-containing conjugate. One application in which the target:blood ratio improvement is sought is in solid tumor imaging and therapy.

Other applications of these CCAs include lesional imaging or therapy involving blood clots and the like, employing antibody or other targeting vehicle-active agent delivery modalities. For example, an efficacious anti-clotting agent provides rapid target localization and high target:non-target ratio. Active agents administered in pretargeting protocols of the present invention using efficient clearing agents are targeted in the desirable manner and are, therefore, useful in the imaging/therapy of conditions such as pulmonary embolism and deep vein thrombosis.

The present invention provides methods of increasing active agent localization at a target cell site of a mammalian recipient, which methods include:

administering to the recipient a first conjugate comprising a targeting moiety and a member of a ligand-anti-ligand binding pair;

thereafter administering to the recipient a CCA incorporating a cluster hepatic clearance directing component, capable of directing the clearance of circulating first conjugate via hepatocyte receptors of the recipient, and a binding component; and subsequently administering to the recipient a second conjugate comprising an active agent and a ligand/anti-ligand binding pair member, wherein the second conjugate binding pair member is complementary to that of its first conjugate.

The present invention also provides methods for decreasing the background active agent concentration in otherwise conventional imaging protocols. These methods involve:

administering to the recipient a first conjugate including a targeting moiety, a member of a ligand-anti-ligand pair and an active imaging agent; and thereafter administering to the recipient a CCA incorporating a cluster hepatic clearance directing component, capable of directing the clearance of circulating first conjugate via hepatocyte receptors of the recipient, and a binding component capable of binding to the first conjugate, wherein upon administration of the CCA, serum-associated first conjugate is cleared and therefore the image background is diminished. In this manner, the quality of diagnostic images can be improved.

Figure 8:
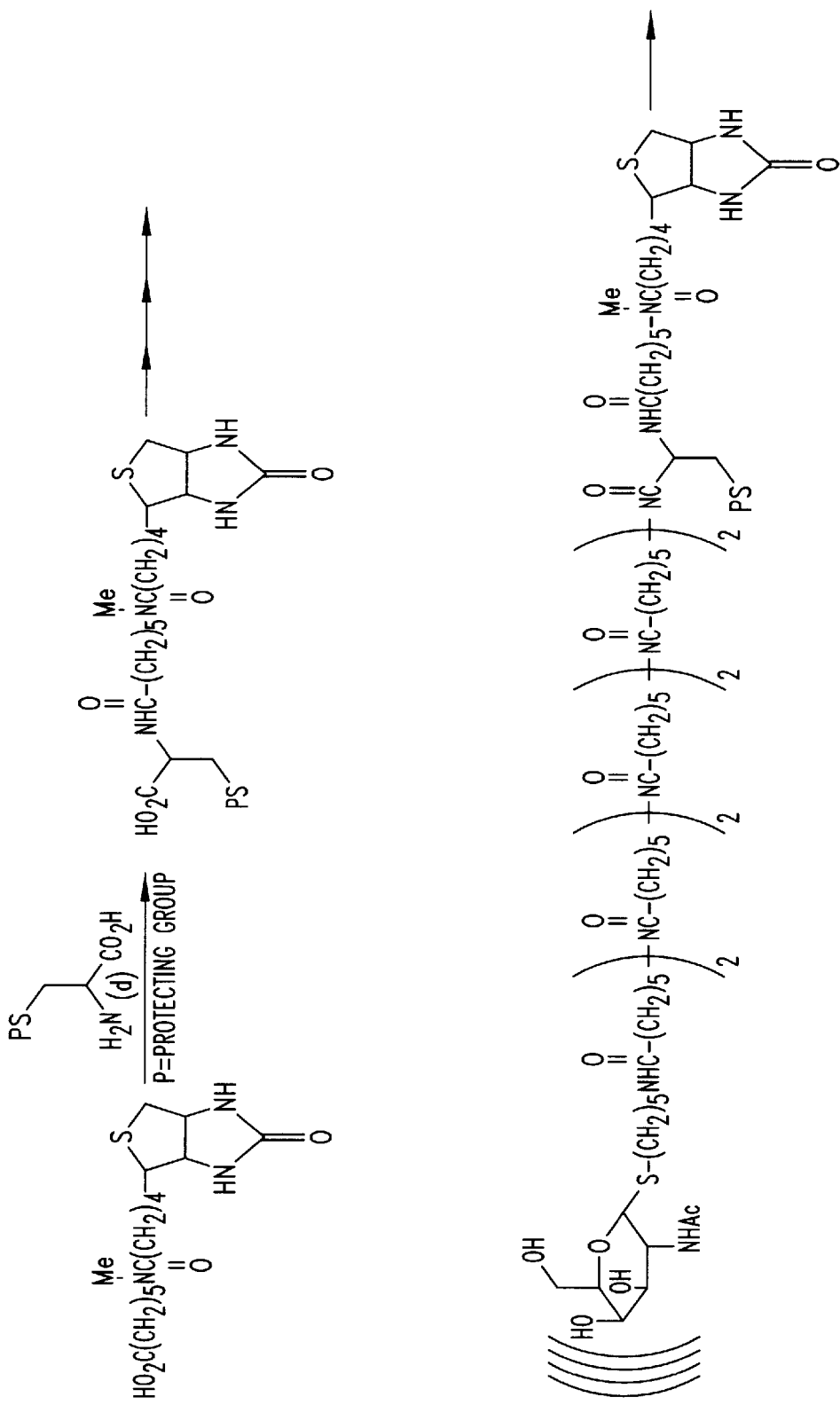
FIG. 8 schematically depicts the preparation of a CCA-protein clearing agent of the present invention.
Figure 8:
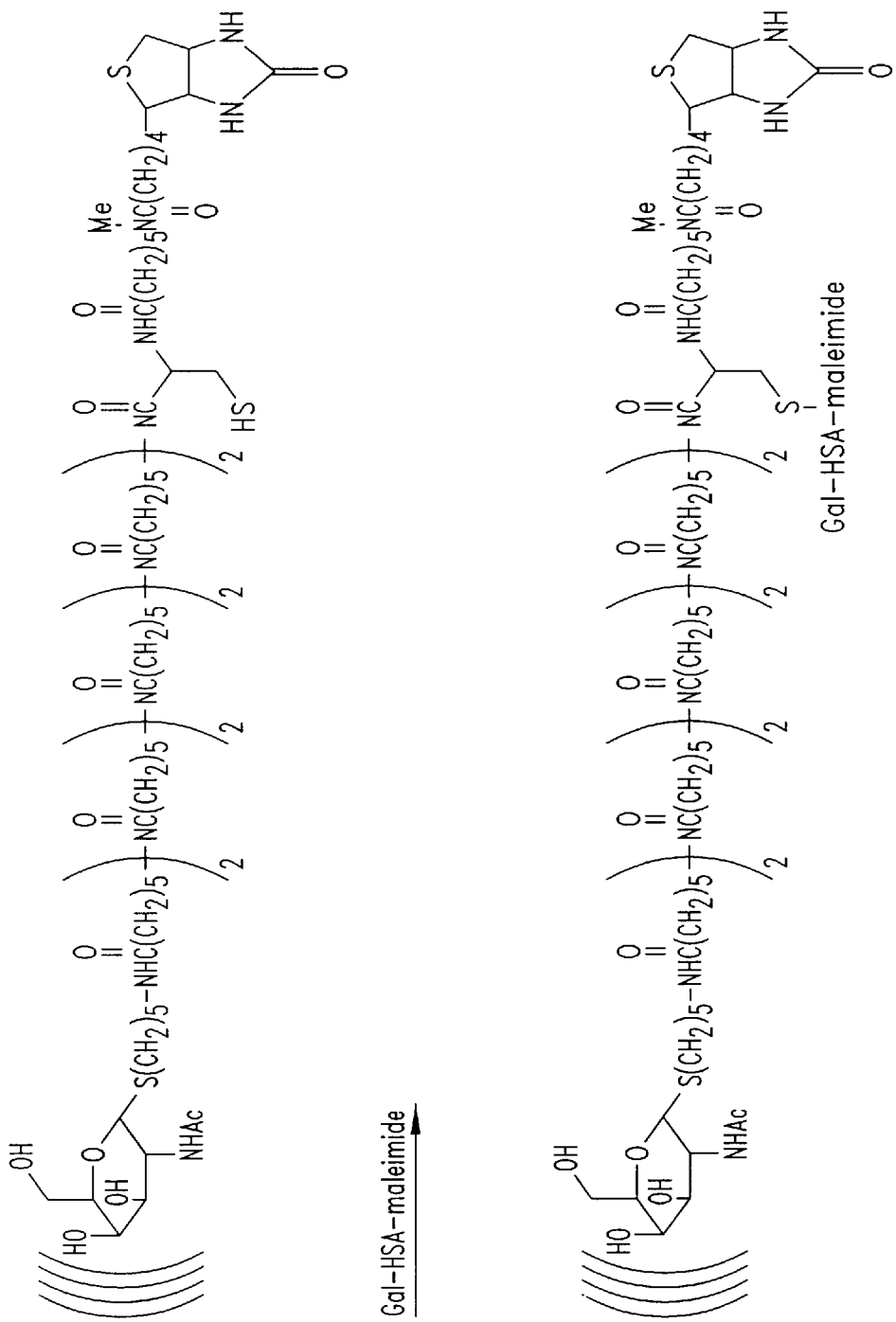

Another improvement of the present invention incorporates a CCA into a proteinaceous clearing agent. For example, HSA may be derivatized with one or more CCAs, preferably 1 or 2 CCAs and optionally by hexose residues. By virtue of the synthetic nature of the CCA and the methylated amide bond(s) incorporated in the linker/extender between the cluster and the binding moiety, the CCA is resistant to metabolic degradation. Consequently, any CCA-biotin metabolites of this proteinaceous clearing agent are likely to be retained in liver hepatocytes. One such construct, illustrated in the synthetic scheme of FIG. 8 incorporates a D-cysteine residue in the extender between biotin and the cluster which serves to donate a reactive thiol. The cysteine thiol may then be employed to bind to hexose-derivatized or non-hexose-derivatized HSA which is derivatized with a maleimide residue.

Clearing agent evaluation experimentation involving galactose- and biotin-derivatized clearing agents is detailed in Example III. The specific clearing agents examined during the Example III experimentation are human serum albumin derivatized with galactose and biotin and a 70,000 dalton molecular weight dextran derivatized with both biotin and galactose. The experimentation showed that proteins and polymers are derivatizable to contain both galactose and biotin and that the resultant derivatized molecule is effective in removing circulating streptavidin-protein conjugate from the serum of the recipient. Biotin loading was varied to determine the effects on both clearing the blood pool of circulating avidin-containing conjugate and the ability to deliver a subsequently administered biotinylated isotope to a target site recognized by the streptavidin-containing conjugate. The effect of relative doses of the administered components with respect to clearing agent efficacy was also examined. Experimentation relating to first generation hexose cluster-bearing moieties is set forth in Example V below. Experimentation involving second generation CCAs is set forth in Example VII below.

The present invention provides CCAs that incorporate ligand derivatives or anti-ligand derivatives, wherein such derivatives exhibit a lower affinity than the native form of the compound, employed in the same construct, for the complementary ligand/anti-ligand pair member (i.e., lower affinity ligands or anti-ligands). In embodiments of the present invention employing a biotin-avidin or biotin-streptavidin ligand/anti-ligand pair, preferred CCAs incorporate either lower affinity biotin (which exhibits a lower affinity for avidin or streptavidin than native biotin) or lower affinity avidin or a streptavidin (which exhibits a lower affinity for biotin than native avidin or streptavidin).

In two-step pretargeting protocols employing the biotin-avidin or biotin-streptavidin ligand-anti-ligand pair, lower affinity biotin, lower affinity avidin or lower affinity streptavidin may be employed. Exemplary lower affinity biotin molecules, for example, exhibit the following properties: bind to avidin or streptavidin with an affinity less than that of native biotin ($10^{-15}$); retain specificity for binding to avidin or streptavidin; are non-toxic to mammalian recipients; and the like. Exemplary lower affinity avidin or streptavidin molecules, for example, exhibit the following properties: bind to biotin with an affinity less than native avidin or streptavidin; retain specificity for binding to biotin; are non-toxic to mammalian recipients; and the like.

Exemplary lower affinity biotin molecules include 2'-thiobiotini; 2'-iminobiotin; 1'-N-methoxycarbonyl-biotin; 3'-N-methoxycarbonylbiotin; 1-oxy-biotin; 1-oxy-2'-thiobiotin; 1-oxy-2'-iminobiotin; 1-sulfoxide-biotin; 1-sulfoxide-2'-thiobiotin; 1-sulfoxide-2'-iminobiotin; 1-sulfone-biotin; 1-sulfone-2'-thio-biotin; 1-sulfone-2'-iminobiotin; imidazolidone derivatives such as desthiobiotin (d and dl optical isomers), dl-desthiobiotin methyl ester, dl-desthiobiotinol, D-4-n-hexyl-imidazolidone, L-4-n-hexylimidazolidone, dl-4-n-butyl-imidazolidone, dl-4-n-propylimidazolidone, dl-4-ethyl-imidazolidone, dl-4-methylimidazolidone, imidazolidone, dl-4,5-dimethylimidazolidone, meso-4,5-dimethylimidazolidone, dl-norleucine hydantoin, D-4-n-hexyl-2-thiono-imidazolidine, d-4-n-hexyl-2-imino-imidazolidine and the like; oxazolidone derivatives such as D-4-n-hexyl-oxazolidone, D-5-n-hexyloxazolidone and the like; [5-(3,4-diamino-thiophan-2-yl] pentanoic acid; lipoic acid; 4-hydroxy-azobenzene-2'-carboxylic acid; and the like. Preferred lower affinity biotin molecules for use in the practice of the present invention are 2'-thiobiotin, desthiobiotin, 1-oxy-biotin, 1-oxy-2'-thiobiotin, 1-sulfoxide-biotin, 1-sulfoxide-2'-thiobiotin, 1-sulfone-biotin, 1-sulfone-2'-thiobiotin, lipoic acid and the like. These exemplary lower affinity biotin molecules may be produced substantially in accordance with known procedures therefor. Incorporation of the exemplary lower affinity biotin molecules into CCAs proceeds substantially in accordance with procedures described herein in regard to biotin incorporation.

Much has been reported about the binding affinity of different biotin analogs to avidin. Based upon what is known in the art, the ordinary skilled artisan could readily select or use known techniques to ascertain the respective binding affinity of a particular biotin analog to streptavidin, avidin or a derivative thereof.

The present invention further provides methods of increasing active agent localization at a target cell site of a mammalian recipient, which methods include:
administering to the recipient a first conjugate comprising a targeting moiety and a member of a ligand-anti-ligand binding pair;
thereafter administering to the recipient a CCA incorporating a cluster hepatic clearance directing moiety capable of directing the clearance of circulating first conjugate via hepatocyte receptors of the recipient, wherein the CCA also incorporates a lower affinity complementary member of the ligand-anti-ligand binding pair employed in the first conjugate; and
subsequently administering to the recipient a second conjugate comprising an active agent and a ligand/anti-ligand binding pair member, wherein the second conjugate binding pair member is complementary to that of the first conjugate and, preferably, constitutes a native or high affinity form thereof.

The "targeting moiety" of the present invention binds to a defined target cell population, such as tumor cells. Preferred targeting moieties useful in this regard include antibody and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, Univ. Mich. Med. Bull., 20:284–6, 1956), affinity-purified polyclonal or fragments thereof (Chao et al., Res. Comm. in Chem. Path. & Pharm., 9:749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, Nature, 256: 495–97, 1975; Eur. J. Immunol., 6: 511-19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Types of active agents (diagnostic or therapeutic) useful herein include toxins, anti-tumor agents, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

Preferred toxins in this regard include holotoxins, such as abrin, ricin, modeccin, Pseudomonas exotoxin A, Diphtheria toxin, pertussin toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein. Extremely highly toxic toxins, such as palytoxin and the like, are also contemplated for use in the practice of the present invention.

Preferred drugs suitable for use herein include conventional chemotherapeutics, such as vinblastine, doorubicin, bleomysin, methotrexate, 5-fluorouracil, 6-thioguanine, cytarabine, cyclophosphamide and cis-platinum, as well as other conventional chemotherapeutics as described in Cancer: Principles and Practice of Oncology, 2d ed., V. T. DeVita, Jr., S. Hellman, S. A. Rosenberg, J. B. Lippincott Co., Philadelphia, Pa. 1985, Chapter 14. A particularly preferred drug within the present invention is a trichothecene.

Trichothecenes are drugs produced by soil fungi of the class Fungi imperfecti or isolated from Baccharus megapotamica (Bamberg, J. R. Proc. Molec. Subcell. Biol. 8:41–110, 1983; Jarvis & Mazzola, Acc. Chem. Res. 15:338–395, 1982). They appear to be the most toxic molecules that contain only carbon, hydrogen and oxygen (Tamm, C. Fortschr. Chem. Org. Naturst. 31:61–117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: Scirpene, Roridin C, dihydrotrichothecene, Scirpen-4, 8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,5-diacetoxyscirpenol, 7-hydroxydiacetoxyscirpenol, 8-hydroxydiacetoxy-scirpenol (Neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin.

Representative examples of Group B simple trichothecenes include: Trichothecolone, Trichothecin, deoxynivalenol, 3-acetyldeoxynivalenol, 5-acetyldeoxynivalencl, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant Baccharis megapolamica, and these are described in the literature, for instance as disclosed by Jarvis et al. (Chemistry of Alleopathy, ACS Symposium Series No. 268: ed. A. C. Thompson, 1984, pp. 149–159).

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1nitrosourea, N,N'- hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (see *NCI Investigational Drugs, Pharmaceutical Data* 1987 NIH Publication No. 88-2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use Radionuclides are well-known in the art and include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Ga, $^{68}$Ga, $^{64}$Cu, $^{67}$Cu, $^{75}$Br, $^{76}$Br, $^{77}$Br, $^{99m}$Tc, $^{11}$C, $^{13}$N, $^{15}$O, $^{166}$Ho and $^{18}$F. Prefered therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu.

Other anti-tumor agents, e.g., agents active against proliferating cells, are administrable in accordance with the present invention. Exemplary anti-tumor agents include cytokines, such as IL-2, tumor necrosis factor or the like, lectin inflammatory response promoters (selectins), such as L-selectin, E-selectin, P-selectin or the like, and like molecules.

Ligands suitable for use within the present invention include biotin, haptens, lectins, epitopes, dsDNA fragments, enzyme inhibitors and analogs and derivatives thereof. Useful complementary anti-ligands include avidin (for biotin), carbohydrates (for lectins) and antibody, fragments or analogs thereof, including mimetics (for haptens and epitopes) and zinc finger proteins (for dsDNA fragments) and enzymes (for enzyme inhibitors). Preferred ligands and anti-ligands bind to each other with an affinity of at least about $k_D$ $10^9$M. Other useful ligand/anti-ligand systems include S-protein/S-peptide, head activator protein (which binds to itself), cystatin-C/cathepsin B, and the like.

One preferred chelate system for use in the practice of the present invention is based upon a 1,4,7,10-tetraazacyclododecane-N,N',N'',N'''-tetra acetic acid (DOTA) construct. Because DOTA strongly binds Y-90 and other radionuclides, it has been proposed for use in radioimmunotherapy. For therapy, it is very important that the radionuclide be stably bound within the DOTA chelate and that the DOTA chelate be stably attached to an effector, such as a ligand or an anti-ligand.

The strategy for design of preferred DOTA molecules incorporating biotin for use in the practice of embodiments of the present invention involved three primary considerations:

1) in vivo stability (including biotinidase and general peptidase activity resistance), with an initial acceptance criterion of 100% stability for 1 hour;
2) renal excretion; and
3) ease of synthesis.

The same or similar criteria are applicable to alternative binding moieties, such as ligands or anti-ligands, as can be readily ascertained by one of ordinary skill in the art.

The DOTA-biotin conjugates that are preferably employed in the practice of the present invention reflect the implementation of one or more of the following strategies:

1) substitution of the carbon adjacent to the cleavage susceptible amide nitrogen;
2) alkylation of the cleavage susceptible amide nitrogen;
3) substitution of the amide carbonyl with an alkyl amino group;
4) incorporation of D-amino acids as well as analogs or derivatives thereof; or
5) incorporation of thiourea linkages.

DOTA-biotin conjugates in accordance with the present invention are described in published PCT Patent Application No. PCT/US/93/05406. A method of preparing preferred DOTA-biotin embodiments is described in Example II hereof.

The preferred linkers are useful to produce DOTA-biotin or other DOTA-small molecule conjugates having one or more of the following advantages:

bind avidin or streptavidin with the same or substantially similar affinity as free biotin;

bind metal $M^{+3}$ ions efficiently and with high kinetic stability;

are excreted primarily through the kidneys into urine;

are stable to endogenous enzymatic or chemical degradation (e.g., bodily fluid amidases, peptidases or the like);

penetrate tissue rapidly and bind to pretargeted avidin or streptavidin; and are excreted rapidly with a whole body residence half-life of less than about 5 hours.

One component to be administered in a preferred two-step pretargeting protocol is a targeting moiety-anti-ligand or a targeting moiety-ligand conjugate. Streptavidin-proteinaceous targeting moiety conjugates are preferably prepared as described in Example I below, with the preparation involving the steps of preparation of SMCC-derivitized streptavidin; preparation of DTT-reduced proteinaceous targeting moiety; conjugation of the two prepared moieties; and purification of the monosubstituted or disubstituted (with respect to streptavidin) conjugate from crosslinked (antibody-streptavidin-antibody) and aggregate species and unreacted starting materials. The purified fraction is preferably further characterized by one or more of the following techniques: HPLC size exclusion, SDS-PAGE, immunoreactivity, biotin binding capacity and in vivo studies.

CCAs of the present invention may be administered in single or multiple doses or via continuous infusion. A single dose of a biotin-containing CCA, for example, produces a rapid decrease in the levelof circulating targeting moiety-streptavidin, followed by a small increase in that level, presumably caused, at least in part, by re-equilibration of targeting moiety-streptavidin within the recipient's physiological compartments. A second or additional CCA doses may then be employed to provide supplemental clearance of targeting moiety-streptavidin. Alternatively, CCA may be infused intravenously for a time period sufficient to clear targeting moiety-streptavidin in a continuous manner.

The dose of CCAs of the present invention will depend upon numerous patient-specific and clinical factors, which clinicians are uniquely qualified to assess. In general, the dose of the CCA to be administered will depend on the dose of the targeting conjugate or other previously administered component to be cleared that is either measured or expected to remain in the serum compartment at the time the CCA is administered. Alternatively, the dose of the CCA will depend on the measured or expected level of toxic agent to be cleared. Generally, a single CCA dose will range from about 20 mg to about 500 mg, with from about 50 mg to about 200 mg preferred. It is important to note that preclinical testing of CCA agents has revealed that great lattitude exists in effective CCA dose range.

One embodiment of the present invention in which rapid acting CCAs are useful is in the delivery of Auger emitters, such as I-125, I-123, Er-165, Sb-119, Hg-197, Ru-97, Tl-201 and Br-77, or nucleus-binding drugs to target cell nuclei. In these embodiments of the present invention, targeting moieties that localize to internalizing receptors on target cell surfaces are employed to deliver a targeting moiety-containing conjugate (i.e., a targeting moiety-anti-ligand conjugate in the preferred two-step protocol) to the target cell population. Such internalizing receptors include EGF receptors, transferrin receptors, HER2 receptors, IL-2 receptors, other interleukins and cluster differentiation receptors, somatostatin receptors, other peptide binding receptors and the like.

After the passage of a time period sufficient to achieve localization of the conjugate to target cells, but insufficient to induce internalization of such targeted conjugates by those cells through a receptor-mediated event, a rapidly acting CCA is administered. In a preferred two-step protocol, an active agent-containing ligand or anti-ligand conjugate, such as a biotin-Auger emitter or a biotin-nucleus acting drug, is administered as soon as the CCA has been given an opportunity to complex with circulating targeting moiety-containing conjugate, with the time lag between CCA and active agent administration being less than about 24 hours. In this manner, active agent is readily internalized through target cell receptor-mediated internalization. While circulating Auger emitters are thought to be non-toxic, the rapid, specific targeting afforded by the pretargeting protocols of the present invention increases the potential of shorter half-life Auger emitters, such as I-123, which is available and capable of stable binding.

The invention is further described through presentation of the following examples. These examples are offered by way of illustration, and not by way of limitation.

EXAMPLE I

Targeting Moiety-Anti-Ligand Conjugate for Two-Step Pretargeting In Vivo

A. Preparation of SMCC-derivitized streptavidin.

31 mg (0.48 mol) streptavidin was dissolved in 9.0 ml PBS to prepare a final solution at 3.5 mg/ml. The pH of the solution was adjusted to 8.5 by addition of 0.9 ml of 0.5 M borate buffer, pH 8.5. A DMSO solution of SMCC (3.5 mg/ml) was prepared, and 477 1 (4.8 mol) of this solution was added dropwise to the vortexing protein solution. After 30 minutes of stirring was purified by G-25 (PD-10, Pharmacia, Picastaway, N.J.) column chromatography to remove unreacted or hydrolyzed SMCC. The purified SMCC-derivitized streptavidin was isolated (28 mg, 1.67 mg/ml).

B. Preparation of DTT-reduced NR-LU-10. To 77 mg NR-LU-10 (0.42 mol) in 15.0 ml PBS was added 1.5 ml of 0.5 M borate buffer, pH 8.5. A DTT solution, at 400 mg/ml (165 1) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

C. Conjugation of SMCC-streptavidin to DTT-reduced NR-LU-10. DTT-reduced NR-LU-10 (63 mg, 29 ml, 0.42 mol) was diluted with 44.5 ml PBS. The solution of SMCC-streptavidin (28 mg, 17 ml, 0.42 mol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

D. Purification of conjugate. For small scale reactions, monosubstituted or disubstituted (with regard to streptavidin) conjugate was obtained using HPLC Zorbax (preparative) size exclusion chromatography. The desired monosubstituted or disubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted or disubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increaseing salt gradient in 20 mM diethanolamine adjusted to pH 8.6 with sodium hydroxide.

E. Characterization of Conjugate.

1. HPLC size exclusion was conducted as described above with respect to small scale purification.
2. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di-substituted conjugates.
3. Immunoreactivity was assessed, for example, by competitive binding ELISA is compared to free antibody. Values obtained were within 10% of those for the free antibody.
4. Biotin binding capacity was assessed, for example, by titrating a known quantity of conjugate with p-[I-125] iodobenzoylbiocytin. Saturation of the biotin binding sites was observed upon addition of 4 equivalences of the labeled biocytin.

5. In vivo studies are useful to characterize the reaction product, which studies include, for example, serum clearance profiles, ability of the conjugate to target antigen-positive tumors, tumor retention of the conjugate over time and the ability of a biotinylated molucle to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

For example, FIG. 1 depicts the tumor uptake profile of the NR-LU-10-streptavidin conjugate (Ab/SA, referred to in this example as LU-10-StrAv) in comparison to a control profile of native NR-LU-10 whole antibody and a control profile of streptavidin. LU-10-StrAv was radiolabeled on the streptavidin component only, giving a clear indication that LU-10-StrAv localizes to target cells as efficiently as NR-LU-10 whole antibody itself.

EXAMPLE II

Synthesis of DOTA-Biotin Conjugates

A. Synthesis of Nitro-Benzyl-DOTA.

The synthesis of aminobenzyl-DOTA was conducted substantially in accordance with the procedure of McMurry et al., *Bioconjugate Chem.*, 3: 108–117, 1992. The critical step in the prior art synthesis is the intermolecular cyclization betwen disuccinimidyl N-(tert-butoxycarbonyl) iminodiacetate and N-(2-aminoethyl)-4-nitrophenyl alaninamide to prepare 1(tert-butoxycarbonyl)-5-(4-nitrobenzyl)-3,6,11-trioxo-1,4,7,10-tetraazacyclododecane. In other words, the critical step is the intermolecular cyclization between the bis-NHS ester and the diamine to give the cyclized dodecane. McMurry et al. conducted the cyclization step on a 140 mmol scale, dissolving each of the reagents in 100 ml DMF and adding via a syringe pump over 48 hours to a reaction pot containing 4 liters dioxane.

A 5x scale-up of the McMurry et al. procedure was not practical in terms of reaction volume, addition rate and reaction time. Process chemistry studies revealed that the reaction addition rate could be substantially increased and that the solvent volume could be greatly reduced, while still obtaining a similar yield of the desired cyclization product. Consequently on a 30 mmol scale, each of the reagents was dissolved in 500 ml DMF and added via addition funnel over 27 hours to a reaction pot containing 3 liters dioxane. The addition rate of the method employed involved a 5.18 mmol/hour addition rate and a 0.047 M reaction concentration.

B. Synthesis of an N-methyl-glycine linked conjugate.

The N-methyl glycine-linked DOTA-biotin conjugate was prepared by an analogous method to that used to prepare D-analine-linked DOTA-biotin conjugates. N-methyl-glycine (trivial name carcosine, available from Sigma Chemical Co.) was condensed with biotin-NHS ester in DMF and triethylamine to obtain N-methyl glycyl-biotin. N-methyl-glycyl biotin was then activated with EDCI and NHS. The resultant NHS ester was not isolated and was condensed in situ with DOTA-aniline and excess pyridine. The reaction solution was heated at 60° C. for 10 minutes and then evaporated. The residue was purified by preparative HPLC to give [N-methyl-N-biotinyl)-N-glycyl]-aminobenzyl-DOTA.

1. Preparation of (N-methyl)glycyl biotin. DMF (8.0 ml) and triethylamine (0.61 ml, 4.35 mmol) were added to solids N-methyl glycine (182 mg, 2.05 mmol) and N-hydroxy-succinimidl biotin (500 mg, 1.46 mmol). The mixture was heated for 1 hour in an oil bath at 85° C. during which time the solids dissolved producing a clear and colorless solution. The solvents were then evaporated. The yellow oil residue was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H—NMR (DMSO): 1.18–1.25 (m, 6H, $(CH_2)_3$), 2.15, 2.35 (2 t's, 2H, $CH_2CO$), 2.75 (m, 2H, $SCH_2$), 2.80, 3.00 (2 s's, 3H, $NCH_3$), 3.05–3.15 (m, 1H, SCH), 3.95, 4.05 (2 s's, 2H, $CH_2N$), 4.15, 4.32 (2 m's, 2H, 2CHN's), 6.35 (s, NH), 6.45 (s, NH).

2. Preparation of [(N-methyl-N-biotinyl)glycyl] aminobenzyl-DOTA. N-hydroxysuccinimide (10 mg, 0.08 mmol) and EDCI (15 mg, 6.08 mmol) were added to a solution of (N-methylglycyl biotin (24 mg, 0.08 mmol) in DMF (1.0 ml). The solution was stirred at 23 C for 64 hours. Pyridine (0.8 ml) and aminobenzyl-DOTA (20 mg, 0.04 mmol) were added. The mixture was heated in an oil bath at 63° C. for 10 minutes, then stirred at 23 C for 4 hours. The solution was evaporated. The residue was purified by preparative HPLC to give the product as an off white solid (8 mg, 0.01 mmol) in 27% yield.

H—NMR ($D_2O$): 1.30–1.80 (m, 6H), 2.40, 2.55 (2 t's, 2H, $CH_2CO$), 2.70–4.2 (complex multiplet), 4.35 (m, CHN), 4.55 (m, CHN), 7.30 (m, 2H, benzene hydrogens), 7.40 (m, 2H, benzene hydrogens).

EXAMPLE III

Clearing Agent Evaluation Experimentation

A. Galactose- and Biotin-Derivatization of Human Serum Albumin (HSA). HSA was evaluated because it exhibits the advantages of being both inexpensive and non-immunogenic. HSA was derivatized with varying levels of biotin (1-about 9 biotins/molecule) via analogous chemistry to that previously described with respect to AO. More specifically, to a solution of HSA available from Sigma Chemical Co. (5–10 mg/ml in PBS) was added 10% v/v 0.5 M sodium borate buffer, pH 8.5, followed by dropwise addition of a DMSO solution of NHS—LC-biotin (Sigma Chemical Co.) to the stirred solution at the desired molar offering (relative molar equivalents of reactants). The final percent DMSO in the reaction mixture should not exceed 5%. After stirring for 1 hour at room temperature, the reaction was complete. A 90% incorporation efficiency for biotin on HSA was generally observed. As a result, if 3 molar equivalences of the NHS ester of LC-biotin was introduced, about 2.7 biotins per HSA molecule were obtained. Unreacted biotin reagent was removed from the biotin-derivatized HSA using G-25 size exclusion chromatography. Alternatively, the crude material may be directly galactoxylated. The same chemistry is applicable for biotinylating non-previously biotinylated dextran.

HSA-biotin was then derivatized with from 12 to 45 galactoses/molecule. Galactose derivatization of the biotinylated HSA was performed according to the procedure of Lee, et al., *Biochemistry*, 15: 3956, 1976. More specifically, a 0.1 M methanolic solution of cyanomethyl-2,3,4,6-tetra-O-acetyl-1thio-D-galactopyranoside was prepared and reacted with a 10% v/v 0.1 M NaOMe in methanol for 12 hours to generate the reactive galactosyl thioimidate. The galactosylation of biotinylated HSA began by initial evaporation of the anhydrous methanol from a 300 fold molar excess of reactive thioimidate. Biotinylated HSA in PBS, buffered with 10% v/v 0.5 M sodium borate, was added to the oily residue. After stirring at room temperature for 2 hours, the mixture was stored at 4° C. for 12 hours. The galactosylated HSA-biotin was then purified by G-25 size exclusion chromatography or by buffer exchange to yield the desired product. The same chemistry is exploitable to galactosylating dextran. The incorporation efficiency of galactose on HSA is approximately 10%.

70 micrograms of Galactose-HSA-Biotin (G—HSA—B), with 12–45 galactose residues and 9 biotins, was administered to mice which had been administered 200 micrograms of StrAv—MAb or 200 microliters of PBS 24 hours earlier. Results indicated that G—HSA—B is effective in removing StrAv—MAb from circulation. Also, the pharmacokinetics of G—HSA—B is unperturbed and rapid in the presence or absence of circulating MAb—StrAv.

B. Non-Protein Clearing Agent. A commercially available form of dextran, molecular weight of 70,000 daltons, pre-derivatized with approximately 18 biotins/molecule and having an equivalent number of free primary amines was studied. The primary amine moieties were derivatized with a galactosylating reagent, substantially in accordance with the procedure therefor described above in the discussion of HSA-based clearing agents, at a level of about 9 galactoses/molecule. The molar equivalence offering ratio of galactose to HSA was about 300:1, with about one-third of the galactose being converted to active form. 40 Micrograms of galactose-dextran-biotin (GAL—DEX—BT) was then injected i.v. into one group of mice which had received 200 micrograms MAb—StrAv conjugate intravenously 24 hours earlier, while 80 micrograms of GAL—DEX—BT was injected into other such mice. GAL—DEX—BT was rapid and efficient at clearing StrAv—MAb conjugate, removing over 66% of circulating conjugate in less than 4 hours after clearing agent administrtion. An equivalent effect was seen at both clearing agent doses, which correspnd to 1.6 (40 micrograms) and 3.2 (80 micrograms) times the stoichiometric amount of circulating StrAv conjugate present.

C. Dose Ranging for G—HSA—B Clearing Agent. Dose ranging studies followed the following basic format:

200 micrograms MAb—StrAv conjugate administered;
24 hours later, clearing agent administered; and
2 hours later, 5.7 micrograms PIP-biocytin administerd.

Dose ranging studies were performed with the G—HSA—B clearing agent, starting with a loading of 9 biotins per molecule and 12–45 galactose residues per molecule. Doses of 20, 40, 70 and 120 micrograms were administerd 24 hours after a 200 microgram dose of MAb—StrAv conjugate. The clearing agent administrations were followed 2 hours later by administration of 5.7 micrograms of I-131-PIP-biocytin. Tumor uptake and blood retention of PIP-biotcytin was examined 44 hours after administration thereof (46 hours after clearing agent administration). The results showed that a nadir in blood retention of PIP-biocytin was achieved by all doses greater than or equal to 40 micrograms of G—HSA—B. A clear, dose-dependent decrease in tumor binding of PIP-biocytin at each increasing dose of G—HSA—B was present, however. Since no dose-dependent effect on the localization of MAb—StrAv conjugate at the tumor was observed, this data was interpreted as being indicative of relatively higher blocking of tumor-associated MAb—StrAv conjugate by the release of biotin from catabolized clearing agent. Similar results to those described earlier for the asialoorosomucoid clearing agent regarding plots of tumor/blood ratio were found with respect to G—HSA—B, in that an optimal belance between blood clearance and tumor retention occurred around the 40 microgram dose.

Because of the relatively large molar amounts of biotin that could be released by this clearing agent at higher doses, studies were undertaken to evaluate the effect of lower levels of biotinylation on the effectiveness of the clearing agent. G—HSA—B, derivatized with either 9, 5 or 2 biotins/molecule, was able to clear MAb—StrAv conjugate from blood at equal protein doses of clearing agent. All levels of biotinylation yielded effective, rapid clearance of MAb—StrAv from blood.

Comparison of these 9-, 5-, and 2-biotin-derivatized clearing agents with a single biotin G—HSA—B clearing agent was carried out in tumored mice, employing a 60 microgram dose of each clearing agent. This experiment showed each clearing agent to be substantially equally effective in blood clearance and tumor retention of MAb—StrAv conjugate 2 hours after clearing agent administration. The G—HSA—B with a single biotin was examined for the ability to reduce binding of a subsequently administered biotinylated small molecule (PIP-biocytin) in blood, while preserving tumor binding of PIP-biocytin to prelocalized MAb—StrAv conjugate. Measured at 44 hours following PIP-biocytin administration, tumor localization of both the MAb—StrAv conjugate and PIP-biocytin was well preserved over a broad dose range of G—HSA—B with one biotin/molecule (90 to 180 micrograms). A progressive decrease in blood retention of PIP-biocytin was achieved by increasing doses of the single biocytin G—HSA—B clearing agent, while tumor localization remained essentially constant, indicating that this clearing agent, with a lower level of biotinylation, is preferred. This preference arises because the single biotin G—HSA—B clearing agent is both effective at clearing MAb—StrAv over a broader range of doses (potentially eliminating the need for patient-to-patient titration of optimal dose) and appears to release less competing biotin into the systemic circulation than the same agent having a higher biotin loading level.

Another way in which to decrease the effect of clearing agent-released biotin on active agent-biotin conjugate binding to prelocalized targeting moiety-streptavidin conjugate is to attach the protein or polymer or other primary clearing agent component to biotin using a retention linker. A retention linker has a chemical structure that is resistant to agents that cleave peptide bonds and, optionally, becomes protonated when localized to a catabolizing space, such as a lysosome. Preferred retention linkers of the present invention are short strings of D-amino acids or small molecules having both of the characteristics set forth above. An exemplary retention linker of the present invention is cyanuric chloride, which may be interposed between an epsilon amino group of a lysine of a proteinaceous primary clearing agent component and an amine moiety of a reduced and chemically altered biotin carboxy moiety (which has been discussed above) to form a compound of the structure set forth below.

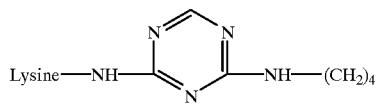

When the compound shown above is catabolized in a catabolizing space, the heterocyclic ring becomes protonated. The ring protonation prevents the catabolite from exiting the lysosome. In this manner, biotin catabolites containing the heterocyclic ring are restricted to the site(s) of catabolism and, therefore, do not compete with active-agent-biotin conjugate for prelocalized targeting moiety-streptavidin target sites.

Comparisons of tumor/blood localization of radiolabeled PIP-biocytin observed in the G—HSA—B dose ranging studies showed that optimal tumor to background targeting was achieved over a broad dose range (90 to 180 micrograms), with the results providing the expectation that even larger clearing agent doses would also be effective. Another key result of the dose ranging experimentation is that G—HSA—B with an average of only 1 biotin molecule is presumably only clearing the MAB—StrAv conjugate via the Ashwell receptor mechanism only, because too few biotins are present to cause cross-linking and aggregation of MAb—StrAv conjugates and clearing agents with such aggregates being cleared by the reticuloendothelial system.

D. Tumor Targeting Evaluation Using G—HSA—B. The protocol for this experiment was as follows:

Time 0: administer 400 micrograms MAb—StrAv conjugate;

Time 24 hours: administer 240 micrograms of G—HSA—B with one biotin and 12–45 galactoses and Time 26 hours: administer 6 micrograms of direct MAb-radiolabel administration. Subsequent experimentation has resulted in AUC tumor/AUC blood over 1000% greater than that achievable by comparable conventional MAb-radiolabel administration. In addition, the HSA-based clearing agent is expected to exhibit a low degree of immunogenicity in humans.

EXAMPLE IV

First Generation CCA (Small Molecule Clearing Agent) Preparation

This procedure is shown schematically in FIG. 2.

Methyl 6-bromohexanoate. To a 1 L round bottom flask, charged with 20 g (102.5 mmol) of 6-bromohexanoic acid and 50 mL of methanol, was bubbled hydrogen chloride gas for 2–3 minutes. The mixture was stirred at room temperature for 4 hours and concentrated to afford 21.0 g of the product as a yellow oil (99%); $^1$H—NMR (200 MHz, $d_6$-DMSO); 3.57 (s, 3H), 3.51 (t, 2H), 2.30 (t, 2H), 1.78 (pentet, 2H), and 1.62–1.27 (m, 4H) ppm.

Methyl 6-aminohexanoate hydrochloride. To a 1 L round bottom flask, charged with 40.0 g aminocaproic acid, was added 500 mL of methanol. Hydrogen chloride gas was bubbled through the mixture for 5 minutes, and the mixture was stirred at room temperature for 5 hours. The mixture was then concentrated via rotary evaporation and then under full vacuum pump pressure (<0.1 mm Hg) to afford 55 g of the product as a white solid (99%): $^1$H—NMR (200 MHz, $CD_3OD$); 3.67 (s, 3H), 3.02 (t, 2H), 2.68 (s, 3H), 2.48 (t, 2H), and 2.03–1.87 (pentet, 2H) ppm.

Methyl 6-(trifluoroacetamido)-hexanoate: To a 1 L round bottom flask, charged with 25.0 g (138 mmol) of methyl 6-aminohexanoate hydrochloride and 500 mL of methylene chloride, was added 24 mL (170 mmol) trifluoroacetic anhydride. The mixture was cooled in an ice bath, and 42 mL (301 mmol) of triethylamine was added over a 25–30 minute period. The mixture was stirred at 0° C. to room temperature for 2 hours and then concentrated. The residue was diluted with 150 mL of diethyl ether and 150 mL of petroleum ether, and the resulting solution was washed first with 1 N aqueous HCl (3×150 mL) and then with saturated aqueous sodium bicarbonate (3×150 mL). The organic phase was dried over magnesium sulfate, filtered and concentrated to give 32.9 g

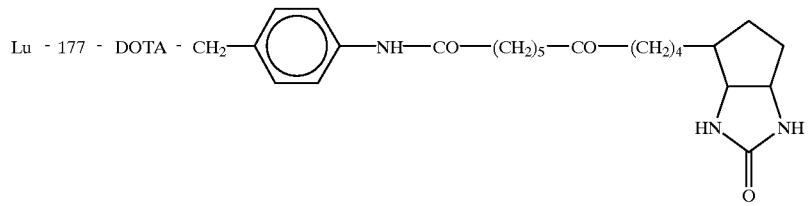

Lu-177 is complexed with the DOTA chelate using known techniques therefor.

Efficient delivery of the Lu177-DOTA-biotin small molecule was observed, 20–25% injected dose/gram of tumor. These values are equivalent with the efficiency of the delivery of the MAb—StrAv conjugate. The AUC tumor/AUC blood obtained for this non-optomized clearing agent dose was 300% greater than that achievable by comparable of the product as a pale yellow oil (99%): $^1$H—NMR (200 MHz, $d_6$-DMSO); 9.39 (m, 1H), 3.57 (s, 3H), 3.14 (q, 2H), 2.29 (t, 2H), 1.60–1.38 (m, 4H), and 1.32–1.19 (m, 2H) ppm.

N,N'-Bis(6-methoxycarbonylhexyl)amine hydrochloride. To a 500 mL dry round bottom flask, charged with 12.0 g (50.0 mmol) of the secondary amide, methyl 6-trifluoroacetamido)-hexanoate, and 250 mL of dry tetrahydrofuran, was added 2.2 g (55 mmol, 1.1 equiv) of 60% sodium hydride. The mixture was stirred at room temperature for 30 minutes and then 10.25 g (49.0 mmol, 0.98 equiv) of the alkyl bromide, methyl 6-bromohexanoate, was added. The mixture was stirred at reflux for 3 hours. an additional 5.80 g (27.7 mmol, 0.55 equiv) of methyl 6-bromohexanoate was added, and the mixture was stirred at reflux for 70 hours. The mixture was cooled, diluted with 150 mL of 1 N aqueous HCl and then extracted with ethyl acetate (3×100 mL). The organic extracts were combined, dried over magnesium sulfate, filtered and concentrated. The residue was diluted with 200 mL of methanol and then treated with 30 mL of 10 N aqueous sodium hydroxide. The mixture was stirred at room temperature for 18 hours and then concentrated. The residue was diluted with 200 mL of deionized water and acidified to pH 1–2 with 37% concentrated HCl. The solution was washed with diethyl ether (3×100 mL). The aqueous phase was concentrated. The residue was diluted with 200 mL of methanol and reconcentrated. The subsequent residue was diluted with 250 mL of methanol, and HCl gas was bubbled through for 2–3 minutes followed by stirring at room temperature for 3 hours. The mixture was concentrated. The residue was diluted with 300 mL of methanol and filtered to remove inorganic salts. The filtrate was treated with 3 g of activated charcoal, filtered through Celite (manufactured by J. T. Baker) and concentrated. The residue, an off-white solid, was recrystallized from 100 mL of 2-propanol to afford 7.0 g of the product as a white solid. Concentration of the filtrate and further recrystallization of the residue yielded an additional 1.65 g of the product for a total of 8.65 g (56%): $^1$H—NMR (200 MHz, d$_6$-DMSO); 3.57 (s, 3H), 2.90–2.73 (m, 4H), 2.30 (t, 4H), 1.67–1.44 (m, 8H), and 1.37–1.20 (m, 4H) ppm.

Methyl 4-methylaminobutyrate hydrochloride. To a 1 L round bottom flask, charged with 30.0 g (195 mmol) of 4-methylaminobutyric acid and 500 mL of methanol, was bubbled HCl gas for 1–2 minutes. The mixture was stirred at room temperature for 3–4 hours and then concentrated to afford 32.5 g of the product as a foamy, off-white solid (99%): $^1$H—NMR (200 MHz, CD$_3$OD); 3.67 (s, 3H), 3.03 (t, 2H), 2.68 (s, 3H), 2.48 (t, 2H), and 2.03–1.87 (pentet, 2H) ppm.

4-Methylaminobutanol. To a 1 L round bottom flask, charged with 32.5 g (194 mmol) of the ester, methyl 4-methylaminobutyrate hydrochloride, was added 500 mL of 1 M borane in tetrahydrofuran over a 1 hour period at 0° C. After the addition was complete, the mixture was refluxed for 20 hours, cooled to 0° C., and the excess borane was destroyed by careful addition of 100 mL of methanol. After all the methanol was added, the mixture was stirred at room temperature for 1 hour and then concentrated. The residue was diluted with 400 mL of methanol and then HCl gas was bubbled into the solution for 5 minutes. The mixture was refluxed for 16 hours. The mixture was cooled, concentrated and then diluted with 250 mL of deionized water. the product was initially free based by addition of 10 N aqueous sodium hydroxide, to a pH of 9–9.95, and then by addition of 70 g of AG 1 X-8 anion exchange resin (hydroxide form) commercially available from BioRad), and by stirring the solution for 2 hours. The resin was filtered off and washed with 150 mL of deionized water. The aqueous filtrates were combined and concentrated. The residue was diluted with 200 mL of 2-propanol and filtered. The collected solids were rinsed with 100 mL of 2-propanol. The organic filtrates were combined and concentrated. The residue was distilled under reduced pressure to afford 12.85 g of the product as a colorless oil (bp 68° C. at 0.1–0.2 mm HG; 64%): $^1$H—NMR (200 MHz, D$_2$O); 3.52 (t, 2H), 2.56 (t, 2H), 2.31 (s, 3H), and 1.65–1.43 (m, 4H) ppm.

4-(N-Methyl-trifluoroacetamido)-1-butanol. To a 250 mL round bottom flask, charged with 10.0 g (96.9 mmol) of the amine, 4-methylaminobutanol, in 100 mL of dry methanol, was added 17.5 mL (147 mmol) of ethyl trifluoroacetate. The mixture was stirred at room temperature for 24 hours and then concentrated to afford 18.55 g of the product as a near colorless oil (96%): $^1$H—NMR (200 MHz, D$_2$O); 3.63 and 3.50 (2t's, 4H), 3.20 and 3.05 (d and s, 3H), and 1.82–1.47 (m, 4H) ppm.

1-(p-Toluenesulfonyloxy)-4-(N-methyl-trifluoroacetamido)butane. To a 1 L dry round bottom blask; charged with 17.0 g (85.4 mmol) of the alcohol, 4-(N-methyl-trifluoroacetamido-1-butanol, in 400 mL of methylene chloride, was added 17.1 g (89.7 mmol, 1.05 equiv) of toluenesulfonyl chloride followed by 30 mL (213 mmol, 2.5 equiv) of triethylamine at 0° C. over a 10 minute period. The mixture was stirred at 0° C. to room temperature for 15 hours and then washed with 5% v/v aqueous HCl (3×200 mL). the organic phase was dried over magnesium sulfate, filtered and concentrated. The residue was chromatographed on silica gel, eluting with 50:50 hexane/methylene chloride and then with methylene chloride, to give 25.1 g of the product as a pale yellow oil (83%): $^1$H—NMR (200 MHz, CDCL$_3$); 7.80 (d, 2H), 7.37 (d, 2H), 4.07 (m, 2H), 3.41 (m, 3H), 3.09 and 2.98 (q and s, 3H), 2.45 (s, 3H), and 1.68 (m, 4H) ppm: TLC (methylene chloride) R$_f$=0.31.

1-S-(2,3,4,6-tetra-O-acetyl-beta-D-galacto-pyranosyl)-2-thiopseudourea hydrobromide. To a 250 mL round bottom flask, charged with 5.08 g (60.3 mmol, 1.09 equiv) of thiourea and 36 mL of acetone, was added 25.0 g (66.7 mmo9l) of tetra-acetyl-alpha-D-galactopyranosyl bromide. The mixture ws stirred at reflux for 15–20 minutes and then cooled on ice. The mixture was filtered into a Buchner funnel and rinsed with 25 mL of ice cold acetone. The solids were treated with 50 mL of acetone, refluxed for 15 minutes, cooled on ice, and filtered. The solids were rinsed with 25 mL of cold acetone, air dried and then dried under vacuum to give 22.6 g of the product as a white solid (76%): $^1$H—NMR (200 MHz, d$_6$-DMSO); 9.4–9.0 (broad d, 4H), 5.63 (d, 1H), 5.38 (d, 1H), 5.23 (dd, 1H), 5.09 (t, 1H), 4.40 (t, 1H, 4.04 (dd, 1H), 2.13 (s, 3H), 2.08 (s, 3H), 2.00 (s, 3H), 1.93 (s, 3H) ppm.

4-(N-Methylaminobutyl)-1-thio-beta-D-galactopyranoside. To a 500 mL round bottom flask, charged with 20.7 g (42.5 mmol, 1.07 equiv) of the thiopseudourea hydrobromide prepared as described above in 70 mL of deionized water, was added 6.4 g (46.3 mmol, 1.16 equiv) of potassium carbonate and 4.7 g (45.2 mmol, 1.13 equiv) of sodium bisulfite followed immediately by 14.1 g (39.9 mmol, 1.0 equiv) of the tosylate, 1-(p-toluenesulfonyloxy)-4-(N-methyl-trifluoroacetamido)butane in 70 mL of acetone. The mixture was stirred at room temperature for 16 hours. The mixture was diluted with 50 mL of brine and extracted with ethyl acetate (3×200 mL). The organic extracts were combined, dried over magnesium sulfate, filtered and concentrated. The residue was chromatographed on silica gel, eluting first with 75% methylene chloride/hexane, followed by methylene chloride, then with 2% methanol/methylene chloride and finally with 10% methanol/methylene chloride. Fractions containing alkylation product with different degrees of acetylation were combined and concentrated. The residue was diluted with 250 mL of methanol and 150 mL of deionized water and treated with 110 g of AG-1 X-8 resin (hydroxide form; 2.6 m equiv/g dry weight) commercially available from BioRad. The mixture was stirred at room temperature for 18 hours. The mixture was filtered, and the resin was rinsed with methanol (2×150 mL). The filtrates were combined and concentrated to afford 6.1 g of product (54%): $^1$H—NMR (200 MHz, $D_2O$); 4.38 (d, 1H), 3.88 (d, 1H), 3.69–3.41 (m, 5H), 2.82–2.64 (m, 4H), 2.43 (s, 3H), and 1.68–1.57 (, 4H) ppm.

Biotin bis-methyl ester: To a 50 mL round bottom flask, charged with 1.00 g (3.23 mmol, 1.13 equiv) of amine hydrochloride, N,N'-bis-(6-methoxycarbonyl-hexyl)amine hydrochloride), and 1.30 g (2.86 mmol) of caproamidobiotin-NHS-ester (preparable by standard methods or commercially available from Sigma Chemical Company) and 10 mL of dry dimethylformamide, was added 1.5 mL (10.6 mmol) of triethylamine. The mixture was stirred at 85° C. for 2 hours and then concentrated via reduced pressure rotary evaporation. The residue was chromatographed on silica gel, eluting with 75:25:0.05 ethyl acetate/methanol/acetic acid, to afford 1.63 g of the product as a white foamy solid (98%): $^1$H—NMR (200 MHz $d_6$-DMSO); 7.72 (t, 1H), 6.41 (s, 1H), 6.34 (s, 1H), 4.29 (m, 1H, 4.11 (m, 1H), 3.57 (s, 6H), 3.23–2.91 (m, 7H) 2.81 (dd, 1H), 2.55 (d, 1H), 2.35–2.13 (m, 6H), 2.03 (t, 2H) 1.65–1.10 (m, 24H) ppm: TLC; $R_f$=0.58 (75:25:0.01 ethyl acetage/methanol/acetic acid).

Biotin bis-acid: To a 200 mL round botom flask, charged with 1.61 g (2.63 mmol) of biotin bis-methyl ester and 50 mL of methanol, was added 5 mL of 3 N aqueous sodium hydroxide. The mixture was stirred at 40° C. for 3 hours and then concentrated via reduced pressure rotary evaporation. The residue was diluted with 50 mL of deionized water, and then 3 N aqueous HCl was added until a pH of 1–2 was attained. The mixture was again concentrated. The residue was chromatographed on C-18 reverse phase silica gel, eluting first with 20:80:−0.1 acetonitrile/water/trifluoroacetic acid and then with 50:50:0.1 acetonitrile/water/trifluoroacetic acid. The fractions containing product were combined and concentrated. The residue was diluted with 40 mL of water and 20 mL of acetonitrile. The solution was frozen (−70° C.) and lyophilized to afford 1.42 g of the product as a fluffy white solid (92%): $^1$H—NMR (200 MHz $d_6$-DMSO); 7.72 (t, 1H), 6.61 (broad s, 2H), 4.29 (m, 1H), 4.11 (m, 1H), 3.35–2.93 (m, 7H) 2.81 (dd, 1H), 2.55 (d, 1H), 2.28–2.12 (m, 6H), 2.03 (t, 2H), 1.68–1.10 (m, 24H) ppm: TLC; $R_f$=0.30 (50:50:0.01 acetonitrile/water/trifluoroacetic acid).

Biotin tetra-methyl ester: To a 50 mL round bottom flask, charged with 350 mg (0.599 mmol) of the biotin bis-acid, 402 mg (1.30 mmol, 2.16 equiv) of amine hydrochloride, N,N'-bis-(6-methoxycarbonyl-hexyl)amine hydrochloride), and 10 mL of dry dimethylformamide, was added 556 mg (1.26 mmol, 2.10 equiv) BOP and 500 microliters (3.54 mmol, 5.91 equiv) of triethylamine. The mixture was stirred at room temperature for 2 hours and then concentrated via reduced pressure rotary evaporation. The residue was chromatographed on C-18 reverse phase silica gel, eluting first with 50:50 methanol/water and then with 85:15 methanol/water, to afford 618 mg of the product as a foamy white solid (95%): $^1$H—NMR (200 MHz $d_6$-DMSO); 7.71 (t, 1H), 6.1 (broad s, 2H), 4.29 (m, 1H), 4.11 (m, 1H), 3.57 (s, 12H, 3.25–2.91 (m, 15H) 2.81 (dd, 1H), 2.55 (d, 1H), 2.35–2.12 (m, 14H), 2.02 (t, 2H), 1.65–1.10 (m, 48H) ppm: TLC; $R_f$=0.48 (85:15 methanol/water).

Biotin tetra-acid: To a 50 mL round bottom flask, charged with 350 mg (0.319 mmol) of biotin tetra-methyl ester and 15 mL of methanol, was added 5 mL of 1 N aqueous sodium hydroxide and 5 mL of deionized water. The mixture was stirred at room temperature for 14 hours and then concentrated via reduced pressure rotary evaporation. The residue was diluted with 15 mL of deionized water, acidified to pH 1–2 by addition of 6 N aqueous HCl and then reconcentrated. The residue was chromatographed on C-18 reverse phase silica gel, eluting first with 50:50 methanol/water and then with 70:30 methanol/water. The fractions containing the product were combined and concentrated. The residue was diluted with 10 mL of water and 8 mL of acetonitrile. The solution was frozen (−70° C.) and lyophilized to afford 262 mg of the product as a fluffy white solid (79%): $^1$H—NMR (200 MHz $d_6$-DMSO); 7.71 (t, 1H), 6.41 (s, 1H), 6.34 (s, 1H), 4.29 (m, 1H), 4.11 (m, 1H), 3.25–2.93 (m, 15H) 2.81 (dd, 1H), (dd, 1H), 2.55 (d, 1H), 2.31–2.10 (m, 14H), 2.02 (t, 2H), 1.63–1.09 (m, 48H) ppm: TLC; $R_f$=0.45 (70:30 methanol/water).

Biotin octa-methyl ester: To a 25 mL round bottom flask, charged with 220 mg (0.710 mmol, 4.93 equiv) of amine hydrochloride, N,N'-bis-(6-methoxycarbonyl-hexyl)amine hydrochloride), 150 mg (0.144 mmol) of the biotin tetra-acid, and 5 mL of dry dimethylformamide, was added 300 mg (0.678 mmol), 4.71 equiv) BOP followed by 500 microliters (3.54 mmol, 24.0 equiv) of triethylamine. The mixture was stirred at room temperature for 3 hours and then concentrated via reduced pressure rotary evaporation. The residue was chromatographed on C-18 reverse phase silica gel, eluting first with 60:40 methanol/water and then with 90:10 methanol/water, to afford 246 mg of the product as a foamy white solid (83%): $^1$H—NMR (200 MHz $d_6$-DMSO); 7.71 (t, 1H), 6.41 (s, 1H), 6.34 (s, 1H), 4.29 (m, 1H), 4.11 (m, 1H), 3.57 (s, 24H), 3.25–2.91 (m, 31H) 2.81 (dd, 1H), (d, 1H), 2.32–2.12 (m, 30H), 2.02 (t, 2H), 1.65–1.08 (m, 96H) ppm: TLC; $R_f$=0.42 (90:10 methanol/water).

Biotin octa-acid. To a 50 mL round bottom flask, charged with 235 mg (0.114 mmol) of biotin octa-methyl ester and 10 mL of methanol, was added 5 mL of 1 N aqueous sodium hydroxide and 5 mL of deionized water. The mixture was stirred at room temperature for 14 hours and then concentrated via reduced pressure rotary evaporation. The residue was diluted with 10 mL of deionized water, acidified to pH 1–2 by addition of 6 N aqueous HCl and then reconcentrated. The residue was chromatographed on C-18 reverse phage silica gel, eluting first with 50:50 methanol/water and then with 75:25 methanol/water. The fractions containing the product were combined and concentrated. The residue was diluted with 20 mL of 1:1 (ratio by volume) acetonitrile/water. The solution was frozen (−70° C.) and lyophilized to afford 202 mg of the product as a fluffy white solid (91%): $^1$H—NMR (200 MHz d$_6$-DMSO); 7.71 (t, 1H), 6.41 (s, 1H), 6.34 (s, 1H), 4.29 (m, 1H), 4.11 (m, 1H), 3.29–2.91 (m, 31H) 2.81 (dd, 1H), 2.55 (d, 1H), 2.31–2.10 (m, 30H), 2.03 (t, 2H), 1.65–1.09 (m, 96H) ppm: TLC; R$_f$=0.51 (75:25 methanol/water).

Biotin hexadeca-methyl ester: To a 25 mL round bottom flask, charged with 154 mg (0.497 mmol, 10.0 equiv) of amine hydrochloride, N,N'-bis-(6-methoxycarbonyl-hexyl) amine hydrochloride), 97 mg (0.0497 mmol) of the bioxin octa-acid, and 5 mL of dry dimethylformamide, was added 202 mg (0.457 mmol, 9.2 equiv) BOP followed by 500 microliters (3.54 mmol, 71.2 equiv) of triethylamine. The mixture was stirred at room temperature for 8 hours and then concentrated via reduced pressure rotary evaporation. The residue ws chromatographed on silica gel, eluting first with 70:30 methanol/water and then with 95:5 methanol/water, to afford 149 mg of the product as a foamy white solid (75%): $^1$H—NMR (200 MHz d$_6$-DMSO); 7.71 (t, 1H), 6.41 (s, 1H), 6.34 (s, 1H), 4.29 (m, 1H), 4.11 (m, 1H), 3.57 (s, 48H), 3.25-2.92 (m, 63H) 2.81 (dd, 1H), 2.55 (d, 1H), 2.35-2.11 (m, 62H), 2.01 (t, 3H), 1.65-1.08 (m, 192H)ppm: TLC; R$_f$=0.31 (95:5 methanol/water).

Biotin hexadecyl-acid: To a 50 mL round bottom flask, charged with 141 mg (0.0353 mmol) of biotin hexadeca-methyl ester and 15 mL of methanol, was added 8 mL of 1N aqueous sodium hydroxide and 5 mL of deionized water. The mixture was stirred at room temperature for 14 hours and then concentrated via reduced pressure rotary evaporation. The residue was diluted with 15 mL of deionized water, acidified to pH 1–2 by addition of 6N aqueous HCl and then reconcentrated. The residue was chromatographed on C-18 reverse phase silica gel, eluting first with 60:40 methanol/water and then with 85:15 methanol/water. The fractions containing the product were combined and concentrated. The residue was diluted with 20 mL of 1:1 acetonitrile/water. The solution was frozen (−70° C.) and lyophilized to afford 130 mg of the product as a fluffy white solid (75%): $^1$H-NMR (200 MHz d$_6$-DMSO); 7.71 (t, 1H), 6.41 (s, 1H), 6.34 (s, 1H), 4.29 (m, 1H), 4.11 (m, 1H), 3.26-2.92 (m, 63H) 2.81 (dd, 1H), 2.55 (d, 1H), 2.35-2.10 (m, 62H), 2.01 (t, 2H), 1.65-1.09 (m, 192H) ppm: TLC; R$_f$=0.64 (85:15 methanol/water).

Hexadeca-galactosyl biotin: To a 25 mL round bottom flask, charged with 125 mg (0.0332 mmol) of biotin hexadeca-acid, 179 mg (0.636 mmol, 19.2 equiv.) of galactose-amine, 4-(N-methylaminobutyl)-1-thio-beta-D-galactopyranoside, and 4 mL of dry methylformamide, was added 264 mg (0.587 mmol, 18.0 equiv) of BOP followed by 400 microliters (3.87 mmol, 86.5 equiv) of dry triethylamine. The mixture was stirred at room temperature for 17 hours and then concentrated via reduced pressure rotary evaporation. The residue was chromatographed on C-18 reverse phase silica gel, eluting first with 60:40 methanol/water and then with 75:25 methanol/water. The fractions containing the product were combined and concentrated and rechromatographed on C-18 reverse phase silica gel, eluting first with 40:60:01 acetonitrile/water/trifluoroacetic acid and then with 50:50:01 acetonitrile/water/trifluoroacetic acid. The fractions containing the product were again combined and concentrated. The residue was dissolved in 20 mL of water. The solution was frozen (−70° C.) and lyophilized to afford 173 mg of the product as a fluffy white solid (75%): $^1$H-NMR (200 MHz D$_2$O); 4.52 (m, 1H), 4.37 (d, 15H), 3.90 (d, 16H), 3.70-3.42 (m, 80H), 3.41-3.05 (m, 95H), 2.98-2.82 (2s and 2m, 49H), 2.80-2.49 (m, 33H), 2.44-2.11 (m, 64H), 1.75-1.10 (m, 256H) ppm: TLC; R$_f$=0.53 (75:25 methanol/water).

The above procedure is designed for the formation of a galactose cluster of 16 galactose residues. The four or eight galactose versions can be made in accordance with this procedure by proceeding from the tetra acid or the octa acid to the galactose derivatization step, which was described above for the 16-galactose cluster. Similarly, 32, etc. galactose cluster constructs can be prepared in accordance with the present invention by introduction of more iterations of the methyl ester and acid formation steps. When the desired number of acid residues are formed, the galactose derivization step is employed, with the proportions of the components adjusted to accommodate the number of acid residues.

EXAMPLE V

First Generation CCA (Small Molecule Clearing Agent) Evaluation

In order to demonstrate the efficacy of the described small molecule clearing agents, a number of such conjugates were synthesized using a biotin binding moiety and galactose residue cluster directors. These conjugates were synthesized using different numbers of attached galactose residues. In addition, these conjugates contained either the long chain linker (LC=containing an aminocaproyl spacer between the amine associated with galactose and the carboxyl moiety associated with the biotin) or the short chain liner (SC= direct link between the amine associated with galactose and the carboxyl moiety associated with the biotin) as set forth below.

The conjugates involved in the testing are depicted below:
(Galactosyl)₁-SC-Biotin
MW: 507.64
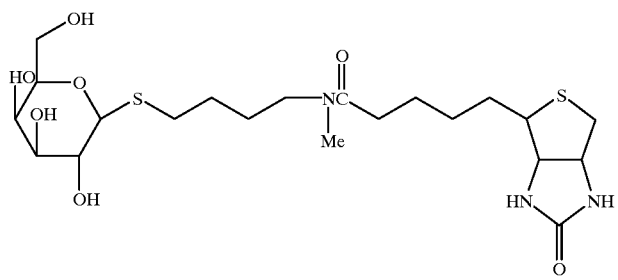
(Galactosyl)₁-LC-Biotin
MW: 620.80
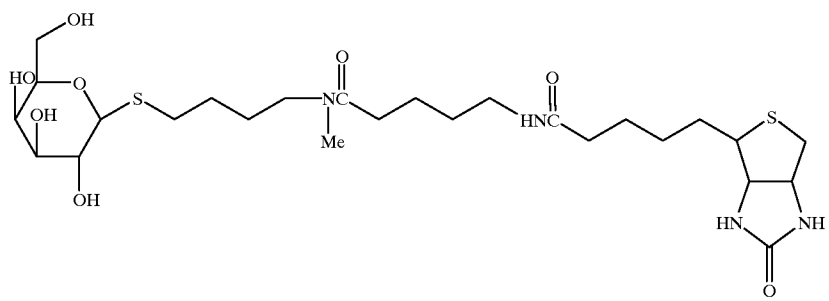
(Galactosyl)₂-SC-Biotin
MW: 998.27
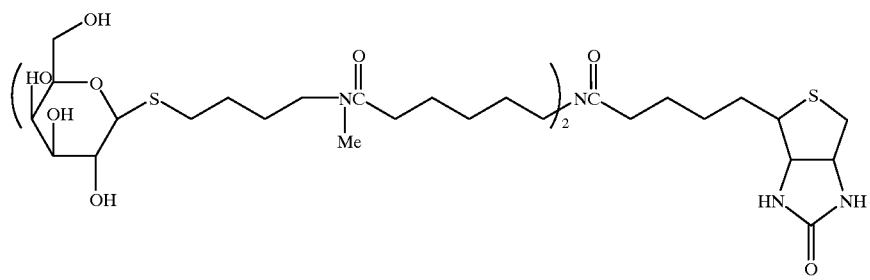
(Galactosyl)₄-SC-Biotin
MW: 1979.63
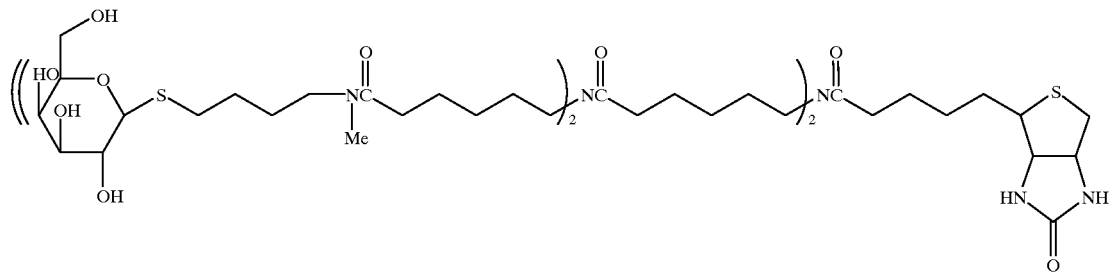
(Galactosyl)₄-LC-Biotin
MW: 2092.79
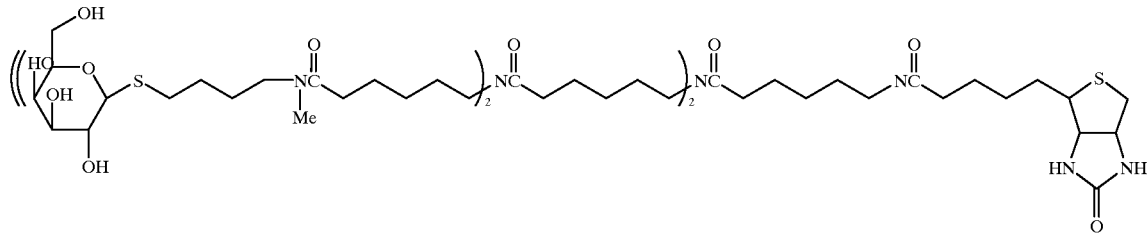

-continued (Galactosyl)₈-SC-Biotin

MW: 3942.28

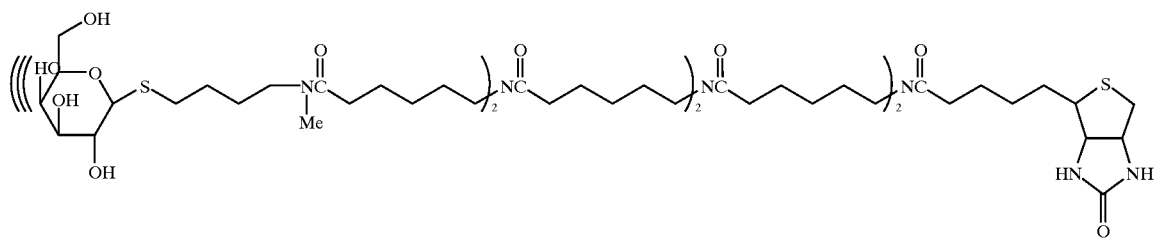

(Galactosyl)₈-LC-Biotin

MW: 4055.42

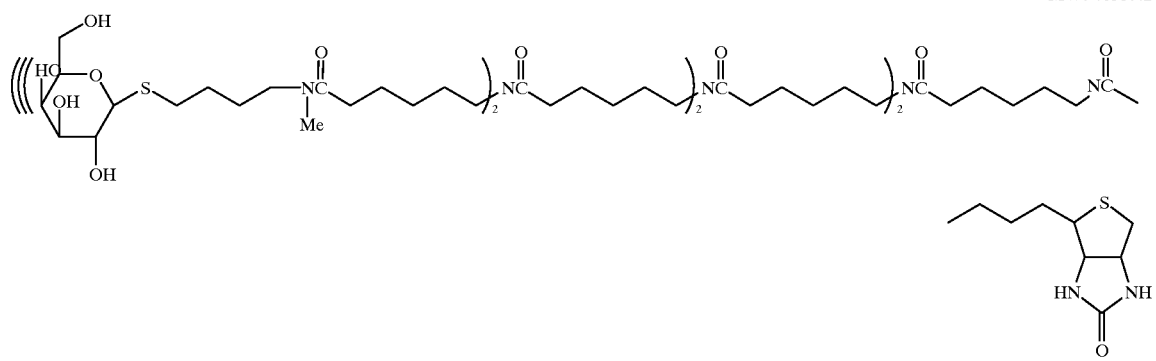

(Galactosyl)₁₆-LC-Biotin

MW: 7961.81

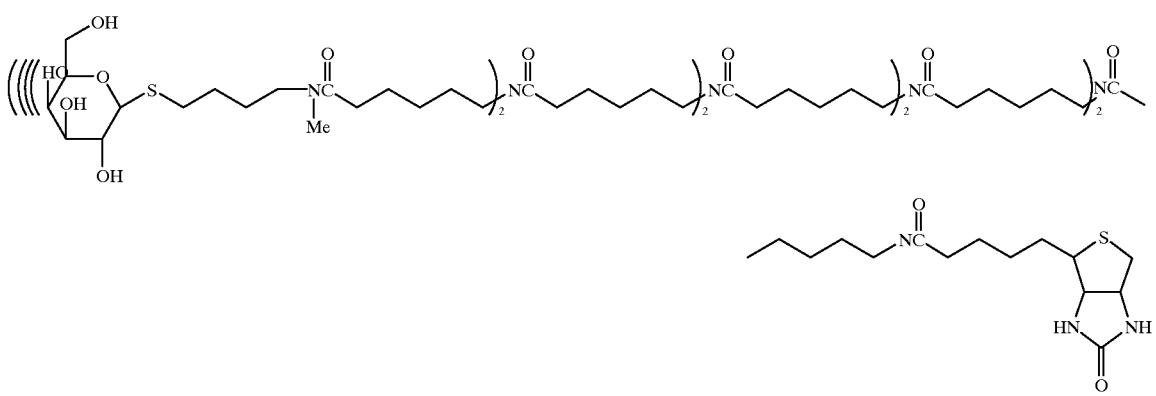

Some or all of these compounds were assayed for their clearance directing activity in two sets of experiments. The first set of experiments involved ex vivo preparation of a precomplexed monoclonal antibody-streptavidin-biotin-galactose cluster conjugate labeled with I-125, intravenous administration of the conjugate in a mouse model, and measuring serum levels of the conjugate over time. The second set of experiments involved intravenous administration of MAb-streptavidin conjugate followed by administration of biotin-galactose cluster conjugate.

NR-LU-10 antibody (MW 150 kD) was conjugated to streptavidin (MW 66 kD) (as described in Example II above), and radiolabeled with $^{125}$I/PIP-NHS as described below. The antibody component of the conjugate was radio-iodinated using p-aryltin phenylate NHS ester (PIP-NHS) and $^{125}$I sodium iodide. In general, the experimentation involving the 2, 4 and 8 galactose-biotin constructs was conducted in an analogous manner to that for the 16 galactose-biotin construct as described below.

The data from these experiments indicates that no significant increase in serum clearance (in comparison to the MAb-Streptavidin conjugate itself) occurs until at least 4 galactose residues are attached to the biotin molecule. In addition, the data indicates that the longer linker separating the galactose cluster from the biotin molecule resulted in better clearance rates. This is consistent with the inventors' belief that the galactose cluster interferes with binding to the conjugate to be cleared if an appropriate length spacer is not used to minimize steric interactions or that sugar-hepatocyte interaction is sterically precluded.

In a third set of experiments conducted in vivo in the pretargeting format (e.g., administration of radiolabeled MAb-streptavidin conjugate followed by administration of clearing agent], the (galactosyl)₈-LC-biotin conjugate was also compared to galactose-HSA-biotin prepared as described above. This comparison was conducted in a Balb/c mouse model and was for the ability to clear an I-125 labeled monoclonal antibody-streptavidin conjugate (I-125 LU-10- streptavidin) from circulation as a function of time. The results of this experiment indicate that the (galactosyl)$_8$-LC-biotin conjugate is comparable to galactosylated-HSA-biotin in its ability to clear the streptavidin-containing conjugate from circulation. Subsequent experiments have further shown that hepatic-directed compounds containing 16 galactose residues provide for even better clearance than those containing 8 galactose residues.

Experiments were designed and executed to evaluate a 16 galactose cluster-biotin construct without the stabilizing tertiary amine structure of the nitrogen of the amide closest to the biotin, the preparation of such a stabilized construct being described above in Example V.

BALB/c female mice (20–g) were injected i.v. with 120 micrograms of NR-LU-10-streptavidin conjugate radiolabeled with I-125, and blood was serially collected from n=3 mice. The clearance of the conjugate from the blood was measured of these control mice. Separate groups of mice were injected with either 120 or 12 micrograms of radiolabeled monoclonal antibody-streptavidin conjugate which had been precomplexed with the 16 galactose-biotin construct by mixing the biotin analog at a 20-fold molar excess with the antibody conjugate, and purifying the excess small molecule from the protein by size exclusion chromatography. Both doses of precomplexed conjugate showed extremely rapid clearance from the blood, relative to the antibody conjugate control.

Having shown that precomplexed material could clear rapidly and efficiently from the blood, experiments were conducted to measure the effectiveness of various doses of the 16 galactose-biotin construct to form rapidly clearing complexes in vivo. Mice received 400 micrograms of I-125 NR-LU-10-streptavidin conjugate intravenously, and approximately 22 hours later received the 16 galactose-biotin construct at doses of 100 50, or 10:1 (456, 28 and 45 micrograms, respectively) molar excess to circulating monoclonal antibody-streptavidin conjugate. While each dose was effective at clearing conjugate, the most effective dose (both kinetic and absolute) was the 10:1 dose. For the larger doses, there appears to be some saturation of the liver receptor, since both larger doses show a plateau in conjugate clearance for about 1 hour after administration of the 16 galactose-biotin construct. The larger doses may be sufficiently high to achieve competition between complexed and non-complexed 16-galactose-biotin for liver receptors, thereby precluding all but a small initial fraction of the complexed MAb-streptavidin conjugate from clearing via the liver. Following the plateau period, clearing of the conjugate remained slow and was eventually less complete than that achieve with the lower dose (approximately 10% of the conjugate remained in circulation at the higher doses, in comparison to 2% for the lower dose). An alternative explanation for this finding rests on the fact that the 16-galactose-biotin construct was not stabilized to potential biotinidase-mediated cleavage (e.g., the chemical synthesis did not incorporate a methyl, lower alkyl, carboxylic acid, lower alkyl carboxylic acid or like group was not bound to the amide nitrogen most closely adjacent the biotin rather than hydrogen). If the 16 galactose-biotin construct is unstable, sufficient biotin may be released at higher doses to that a significant portion of circulating conjugate became blocked thereby and, consequently, was not cleared via hepatic-mediated uptake.

Evident in all groups is the lack of a "rebound" or gradual increase in blood levels of circulating conjugate following disruption of the equilibrium between vascular and extravascular concentrations of conjugate. This constitutes the best evidence to date that galactose cluster-biotin constructs extravasate into extravascular fluid, and that conjugate which is complexed extravascularly clears very rapidly when it passes back into the vascular compartment.

Further experimentation in the same animal model compared (galactose)$_{35}$-HSA-(biotin$_2$ clearing agents prepared as described above and decreasing doses of 16 galactose-biotin construct as in vivo clearing agents. A 46 microgram dose of 16 galactose-biotin was found to be optimal and more effective than the previously optimized dose of (galactose)$_{35}$-HSA-(biotin)$_2$. Lower (12 and 23 microgram) and higher (228 microgram) doses of 16 galactose-biotin were less efficient at removing circulating conjugate, and the lower doses showed a significant rebound effect, indicating that incomplete complexation with circulating conjugate may have occurred.

Having shown that effective clearing could be achieved with the appropriate does of 16 galactose-biotin construct, studies were undertaken in tumored nude mice to evaluate the potential blockade of tumor-associated conjugate by the small 16 galactose-biotin. Mice bearing either SW-1222 colon tumor xenografts or SHT-1 small cell lung cancer (SCLC) tumor xenografts were pretargeted with NR-LU-1-streptavidin conjugate and, 22 hours later, received 46 micrograms of 16 galactose-biotin. After 2 hours, Y-90-DOTA-biotin prepared as described above was administered, and its uptake and retention in tumor and non-target tissues was evaluated by sacrifice and tissue counting for radioactivity 2 hours post-administration.

In comparison to historical controls employing (galactose)$_{35}$-HSA-(biotin)$_2$, tumor targeting was slightly lower in the high antigen-expressing colon xenograft and was slightly higher in the low antigen-expressing SCLC xenograft. Given the normal variability in such experiments, tumor uptake of radioactivity was assessed as roughly equivalent, a surprising result given the potential for target uptake of 16 galactose-biotin. Non-target organ uptake was comparable in all tissues except liver, where animals receiving 16 galactose-biotin showed slightly higher levels. The historical controls were conducted with a 3 hour time period between clearing agent and radioactivity administration. When such a 3 hour period was allowed between 16 galactose-biotin and radioactivity administration, the liver levels were lower and comparable to that of the HSA-containing agent (approximately 1% injected dose/gram).

Experiments were also carried out using I-125 labeled MAb-streptavidin conjugate and IN-111 labeled DOTA-biotin to assess the relative stoichiometry of those materials at the tumor target site using 16 galactose-biotin as a clearing agent. Previous studies with (galactose)$_{35}$-HSA-(biotin)$_2$ had shown that an expected 4:1 ratio of DOTA-biotin to MAb-streptavidin (streptavidin has 4 biotin binding sites) could be achieved at the tumor with an optimized dose of that clearing agent. When a similar protocol was employed with the 16 galactose-biotin construct, the ratio of DOTA-biotin to MAb-streptavidin was only 2.65. This indicated that some filling of tumor-associated streptavidin may have occurred, although the nature of such blockage (16 galactose-biotin or biotin released therefrom) was undetermined. Experiments to assess the nature of this blockade are underway.

In summary, galactose cluster conjugates exhibited ability to clear circulating conjugate, provided the galactose cluster contains a sufficient number of appropriately spaced galactosyl residues. 16 Galactose-biotin has proven to be an effective construct for clearing MAb-streptavidin from the circulation (both vascular and extravascular spaces). Despite an apparent blockade of some pretargeted biotin binding sites at the tumor, efficient tumor targeting can still be achieved using this agent. Stabilization of the linkage between biotin and the galactose cluster may minimize any tumor-associated biotin binding site compromise by the galactose cluster-biotin construct.

EXAMPLE VI

Second Generation CCA Preparation

Preparation of second generation CCAs is shown schematically in FIGS. 3–7.

A. Preparation of 16-N-AcetylGalactosamine-Biotin-CCA (alpha-sulfur) Corresponding to Compound 25 in FIG. 3.

Preparation of Methyl 6-bromohexanoate (1)

To a 2 liter round bottomed flask, charged with 99.7 g (0.511 mol) of 6-bromohexanoate (Aldrich Chemical Co., Milwaukee, Wis.) and 1 liter of methanol, was bubbled hydrogen chloride gas for 1–2 minutes. The mixture was stirred at 20–30° C. for 18 h and then concentrated via rotary evaporation. The residue was diluted with 500 mL of diethyl ether and washed with 150 mL of de-ionized water, 200 mL of saturated sodium bicarbonate, and then once again with 200 mL of de-ionized water. The organic phase was dried over anhydrous magnesium sulfate, filtered and concentrated via rotary evaporation. The residue was distilled under vacuum to afford 99.6 g of the product (1) as a colorless oil (93%): b.p.=93–96° C. at 3 mm Hg: $^1$H NMR ($d_6$-DMSO) d 3.57 (3H, s), 3.51 (2H, t), 2.30 (2H, t), 1.78 (2H, pentet) and 1.62-1.28 (4H, m) ppm.

Preparation of Methyl 6-Aminohexanoate Hydrochloride (2)

To a 2 liter round bottom flask, charged with 101.3 g (0.722 mol) of 6-aminohexanoate (Aldrich Chemical Co.) in 1 liter of methanol was bubbled hydrogen chloride gas for 3–4 minutes. the mixture was stirred at 20–30° C. for 16 h and then concentrated via rotary evaporation. The residue was twice diluted with 500 mL of methanol and re-concentrated (<0.5 mm Hg) to afford 140.1 g of the product (2) as a white solid (100%): $^1$H NMR ($d_6$-DMSO) d 9.40 (1H, broad triplet), 3.57 (3H, s), 3.15 (2H, quartet), 2.29 (2H, t), 1.60-1.38 (4H, m) and 1.32-1.19 (2H, m) ppm.

Preparation of Methyl 6-(Trifluoroacetamido)hexanoate (3 3)

To a 2 liter round bottom flask, charged with 100.2 g (0.552 mol) of amine hydrochloride 2 and 1 liter of methanol was added 100 g (0.703 mol) of ethyl trifluoroacetate followed by 120 mL (0.861 mol) of triethylamine. The mixture was stirred at 20–30° C. for 19 h and then concentrated via rotary evaporation. The residue was diluted with 500 mL of diethyl ether and then filtered. The filtrate was washed with 3×300 mL aliquots of 1N aqueous HCl, 200 mL of de-ionized water, 2×200 mL aliquots of saturated aqueous sodium bicarbonate and finally with 200 mL of de-ionized water. The organic phase was dried over anhydrous magnesium sulfate, filtered and concentrated. The residue was distilled under vacuum to afford 115.8 g of the product (3) as a colorless oil: b.p.=113–116° C. at 120 mm Hg: $^1$H NMR ($d_6$-DMSO) d 3.57 (3H, s), 2.75 (2H, m), 2.29 (2H, t), 1.60-1.40 (4H, m) and 1.37-1.19 (2H, m) ppm.

Preparation of N,N-Bis-(5-Methoxycarbonylpentyl)amine Hydrochloride (4)

To a 5 liter three neck flask equipped with a reflux condenser connected to a gas bubbler, charged with 20.9 g of 60% sodium hydride (0.523 mol) in 1 liter of anhydrous dioxane, was added 100 g (0.416 mol) of secondary amide 3 in 200 mL of dry dioxane over a 20 minute period. The mixture was stirred at 20–30° C. for 1 h, and then 130 g (0.622 mol) of bromide 1 in 100 mL of dioxane was added. The mixture was heated to reflux and stirred for 7 h. An additional 10 g of 1 was added and the resulting mixture stirred for 15 h more. The mixture was cooled and concentrated via rotary evaporation. The residue was diluted with 600 mL of 1N aqueous HCl and extracted with 1 liter of ethyl acetate. The organic phase was then washed with 250 mL of de-ionized water, 250 mL of 5% aqueous sodium metabisulfite, and finally with 250 mL of de-ionized water. The organic phase was dried over anhydrous magnesium sulfate, filtered and concentrated.

The residue was diluted with 300 mL of de-ionized water and 500 mL of methanol and treated with 200 mL of 10N aqueous sodium hydroxide. The mixture was stirred at 20–30° C. for 16 h and concentrated to a thick syrup via rotary evaporation. The residue was diluted with 800 mL of deionized water and acidified to pH 1–2 with 200 mL of concentrated HCl. The mixture was washed with 3×300 mL aliquots of diethyl ether and the aqueous phase then concentrated to a thick syrup via rotary evaporation. The residue was diluted with 1 liter of dry methanol and re-concentrated via rotary evaporation. The residue was diluted with 1 liter of dry methanol and then hydrogen chloride gas was bubbled into the mixture of 2–3 minutes. The mixture was stirred at 20–30° C. for 18 h, and then vacuum filtered through Celite (manufactured by J. T. Baker). The solids were rinsed with 200 mL of methanol. The combined filtrates were concentrated. The residue was diluted with 1 liter of methanol and hydrogen chloride gas again bubbled into the mixture for 2–3 minutes. The mixture was stirred for 3 h and then concentrated. The residue was diluted with 1 liter of methanol and 10 g of activated charcoal was added. The mixture was stirred for 30 minutes and then vacuum filtered through Celite. The solids were washed with 100 mL of methanol and the combined filtrates concentrated. The residue was dissolved in hot 2-propanol and then allowed to recrystallize, first at room temperature and then with the use of an ice bath. The solids were filtered and rinsed with 3×75 mL aliquots of cold 2-propanol. The solids were air dried to afford 70.5 g of the product (4) as a white solid. The filtrates were combined and concentrated. The residue was recrystallized from 200 mL of 2-propanol to afford an additional 15.3 g of product for a total of 85.8 g (67%): $^1$H NMR ($d_6$-DMSO) d 8.69 (2H, broad), 3.57 (6H, s), 2.82 (4H, m), 2.30 (4H, t), 1.67-1.43 (8H, m) and 1.28-1.19 (4H, m) ppm;

$^1$H NMR (CD$_3$OD) d 3.66 (6H, s), 3.42 (4H, t), 2.34 (4H, t), 1.75-1.55 (8H, m) and 1.45-1.25 (4H, m) ppm.

Preparation of N-BOC-5-Aminopentanol (5)

To a 2 liter three neck round bottom flask, fitted in the center neck with 500 mL addition funnel and in a side neck with an adaptor venting to a gas bubbler, was added 40 g (0.388 mol) of 5 aminopentanol in 500 mL of dry acentonitrile. Then 84.5 g (0.387 mol) of di-t-butyl-dicarbonate in 400 mL of dry acetonitrile was added over a 50 minute period. The mixture was stirred at 20–30° C. for 15 h and then concentrated. The residue was diluted with 600 mL of ethyl acetate and washed with 2×200 mL aliquots of 0.5N aqueous HCl and 2×200 mL aliquots of de-ionized water. The organic phase was dried over anhydrous magnesium sulfate, vacuum filtered, and concentrated, first via rotary evaporation and then using full vacuum pump pressure (<0.5 mm Hg), to afford 74.5 g of the product (5) as a near colorless oil (88%): $^1$H NMR (d$_6$-DMSO) d 6.72 (1H, broad triplet), 4.31 (1H, t), 3.43-3.27 (2H, m), 2.87 (2H, quartet), and 1.45-1.10 (15H, s and multiplet) ppm; $^1$H NMR (CDCl$_3$) d 4.58 (1H, broad s), 3.65 (2H, t), 3.13 (2H, quartet), and 1.70-1.30 (15H, singlet and multiplet) ppm: Thin Layer Chromatography (Visualization with ninhydrin spray and heat); Silica Gel, R$_f$=0.28 ($^{95}$/$_5$ methylene chloride/methanol).

Preparation of N-BOC-5-Aminopentyltoluenesulfonate (66)

To a 1 liter round bottom flask, charged with 74.5 g (0.366 mol) of N-BOC-aminopentanol (6) in 400 mL of methylene chloride, was added 45 mL of anhydrous pyridine followed by 74.1 g (0.389 mol) of p-toluenesulfonyl chloride. The mixture was stirred at room temperature for 17 h, diluted with 200 mL of methylene chloride and washed with 400 mL of 0.5N HCl, 2×200 mL aliquots of 0.5N HCl, and 2×100 mL aliquots of de-ionized water. The organic phase was dried over anhydrous magnesium sulfate, vacuum filtered, and concentrated. The residue was chromatographed on 11×23 cm of silica gel, eluting first with methylene chloride and then with 3:97 ethyl acetate/methylene chloride. The fractions containing product were combined and concentrated, first via rotary evaporation and then under full vacuum pump pressure (<0.5 mm Hg), to afford 82.13 g of the product (6) as a white solid: $^1$H NMR (CDCl$_3$) d 7.77 (2H, d), 7.31 (2H, d), 4.45 (1H, broad s), 3.98 (2H, t), 3.03 (2H, t), 2.41 (3H, s), and 1.80-1.20 (15H, singlet and multiplet)ppm: Thin Layer Chromatography (Visualization with ninhydrin spray and heat); Silica Gel, R$_f$=0.50 (3:97 ethyl acetate/methylene chloride).

Preparation of 1-b,3,4,6-Tetra-O-Acetyl-N-Acetyl-Galactosamine (7)

To a 500 mL round bottom flask charged with 25.0 g (116 mmol) of galactosamine hydrochloride (Sigma Chemical Co., St. Louis, Mo.) was added 180 mL of anhydrous pyridine and then 115 mL of acetic anhydride (1.22 mol). The mixture was stirred at 20–30° C. for 44 h and then poured into a 2 liter beaker containing 600 g of ice and 600 mL of de-ionized water. The mixture was stirred at room temperature for 10–15 minutes and then vacuum filtered. The collected solids were rinsed with 4×100 mL aliquots of de-ionized water, air dried for 2 h and then dried under full vacuum pump pressure (<0.5 mm Hg) for 14 h to give 39.8 g of the product as a white sole (88%): $^1$H NMR (d$_6$-DMSO) d 7.89 (1H, d), 5.63 (1H, d), 5.16 (1H, d), 5.07 (1H, dd), 4.28-3.92 (4H, m), 2.11 (3H, s), 2.02 (3H, s), 1.99 (3H, s), 1.90 (3H, s) and 1.88 (3H, s) ppm.

Preparation of 3,4,6-Tri-O-Acetyl-N-Acetyl-Galactosamine-1-b-Pseudothiourea Hydrochloride (9)

To a 1 liter round bottom flask, charged with 39.8 g (102 mmol) of 7, was added 400 mL of acetyl chloride. The mixture was stirred at 47–48° C. for 64 h. The mixture was concentrated and then twice diluted with 200 mL of methylene chloride and re-concentrated, first via rotary evaporation and then under full vacuum pump pressure (<0.5 mm Hg), to afford 40.2 g of the crude product (8) as a dark amber foamy solid: H NMR (CDCl$_3$) d 6.24 (1H, d), 5.61 (1H, d), 5.43 (1H, dd), 5.27 (1H, dd), 4.83-4.71 (1H, m), 4.48 (1H, t), 4.22-4.01 (2H, 2 dd's), 2.15 (3H, s), 2.02 (3H, s), 2.00 (3H, s) and 1.98 (3H, s) ppm. To the crude chloride (8), in a 1 liter round bottom flask, was added 9.3 g (122 mmol) of thiourea and 150 mL of acetone. The mixture was stirred at reflux for 40 minutes and then cooled in an ice bath for 30 minutes and then vacuum filtered. The collected solids were rinsed with 2×75 m aliquots of acetone. The solids were then air dried for 45 minutes and then dried further under full vacuum pump pressure (<0.5 mm Hg) for 2 h to afford 33.0 g of the product (9) as a light beige solide (74% overall yield from 7): $^1$H NMR (d$_6$-DMSO) d 9.38 and 9.12 (2 broad s's, 3H), 8.36 (1H, d), 5.56 (1H, d), 5.34 (1H, d), 5.01 (1H, dd), 4.38 (1H, t), 4.22-4.00 (3H, m), 2.11 (3H, s), 2.01 (3H, s), 1.92 (3H, s) and 1.81 (3H, s) ppm.

Preparation of 1-b-Mercapto 3,4,6-Tri-O-Acetyl-N-Acetyl-Galactosamine (10)

To a 1 liter round bottom flask, charged with 30.0 g (67.9 mmol) of the pseudothiourea (9) in 175 mL of methylene chloride and 175 mL of de-ionized water was added 7.08 g (37.24 mmol) of sodium metabisulfite followed by careful addition of 10.2 g (74.5 mmol) of potassium carbonate. The mixture was stirred at room temperature for 40 minutes and the mixture then transferred to a 500 mL separatory funnel. The layers were separated and the aqueous phase was then extracted with 2×125 mL aliquots of methylene chloride. The organic extracts were combined, dried over anhydrous sodium sulfate, filtered and concentrated to give 24.2 g (10) of the product as a very pale yellow (off-white) solid (98%): $^1$H NMR (CDCl$_3$) d 6.24 (1H, d), 5.61 (1H, d), 5.43 (1H, dd), 5.27 (1H, dd), 4.83-4.71 (1H, m), 4.48 (1H, t), 4.22-4.01 (2H, 2 dd's), 2.15 (3H, s), 2.02 (3H, s), 2.00 (3H, s) and 1.98 (3H, s) ppm.

Preparation of 3,4,6-Tri-O-Acetyl-N-Acetyl-Galactosamine-1-a-S-[5'-Thiopentyl-N-BOC-Amine] (11)

To a 1 liter round bottom flask, charged with 24.2 g (66.6 mmol) of the thiol (10) under nitrogen atmosphere, was added 350 mL of dry acetonitrile. The mixture was heated to 40–42° C., the solids eventually dissolving over a 20 minute period. 1,8-Diazabicyclo[5.4.0]undec-7-ene (DBU commercially available from Aldrich Chemical Company, 10.5 mL, 70.2 mmol) was then added and the mixture stirred for 20 minutes. Then, 24.0 g (67.1 mmol) of the tosylate 6 in 75 mL of acetonitrile was added over a 3–4 minute period. The resultant mixture was stirred at 40-25° C. for 1.5 h and then concentrated. The residue was diluted with 400 mL of methylene chloride and washed first with 250 mL of 0.5N aqueous HCl and then with 250 mL of 5% aqueous sodium bicarbonate. The organic phase was dried over anhydrous magnesium, vacuum filtered, and concentrated via rotary evaporation. The residue was chromatographed on 21×7 cm of silica gel (manufactured by E. M. Merck), eluting with 55/42.5/2.5 ethyl acetate/hexane/ethanol. The fractions containing product were combined, concentrated and re-chromatographed on 21×7 cm of RP-18 silica gel (manufactured by J. T. Baker), eluting with 500 mL each of 50/50, 60/40, 65/35, and 70/30 methanol/water and then with 75/25 methanol/water until all of the desired product had eluted from the column. The fractions containing product were combined and concentrated. The residue was diluted with 500 mL of methylene chloride and treated with anhydrous magnesium sulfate. The mixture was vacuum filtered and the filtrate was concentrated, first via rotary evaporation and then under full vacuum pump pressure (<0.5 mm Hg) to afford 17.9 g of the product (11) as a foamy white solid: $^1$H NMR ($d_6$-DMSO) d 9.38 and 9.12 (2 broad s's, 3H), 8.36 (1H, d), 5.56 (1H, d), 5.34 (1H, d), 5.01 (1H, dd), 4.38 (1H, t), 4.22-4.00 (3H, m), 2.11 (3H, s), 2.01 (3H, s), 1.92 (3H, s) and 1.81 (3H, s) ppm: Thin Layer Chromatography (Visualization with p-anisaldehyde spray and heat); Silica Gel, $R_f$=0.50 (57/40.5/2.5 ethyl acetate/hexane/ethanol); RP-18 Silica Gel, $R_f$=0.21 (65/35 methanol/water).

Preparation of Methyl-6-Methylaminohexanoate Hydrochloride (12)

To a 2 liter three neck round bottom flask, charged with 8.77 g of 60% NaH in mineral oil (219 mmol, 1.1 equiv.) in 500 mL of anhydrous tetrahydrofuran, was fitted a 500 mL addition funnel in the center neck. Then, 34.5 g (144 mmol) of secondary amide in 3 in 300 mL of anhydrous tetrahydrofuran was added over a 30 minute period. The mixture was stirred for 50 additional minutes and then 22.6 mL (363 mmol) of iodomethane was added. The mixture was stirred at room temperature for 23 h and then transferred to a 2 liter round bottom flask and concentrated via rotary evaporation. The residue was treated with 400 mL of 1N aqueous HCl and then extracted with 300 mL of ethyl acetate and then with 2×200 mL aliquots of ethyl acetate. The organic extracts were combined and first washed with 3×125 mL aliquots of 5% aqueous sodium thiosulfate and then with 100 mL of de-ionized water. The organic phase was dried over anhydrous magnesium sulfate, vacuum filtered, and concentrated. The residue was dissolved in 250 mL of methanol and re-concentrated. The residue was dissolved in 250 mL of methanol and treated with 50 mL of 10N aqueous sodium hydroxide followed by 100 mL of de-ionized water. The mixture was stirred at room temperature for 17 h, diluted with an additional 50 mL of de-ionized water and then washed with 3×200 mL aliquots of hexane. The aqueous phase was concentrated via rotary evaporation. The residue was diluted with 500 mL of methanol and hydrogen chloride gas was bubbled into the mixture for 2–3 minutes (10 g). The mixture was stirred at room temperature for 3 h and then vacuum filtered and concentrated via rotary evaporation. To the residue was added 500 mL of methanol and then hydrogen chloride gas was again bubbled into the mixture for 2–3 minutes (9.2 g). The mixture was stirred at room temperature for 18 h. The mixture was cooled in an ice bath and then vacuum filtered. The filtrate was concentrated by rotary evaporation. The residue was twice diluted with 250 mL of methanol and re-concentrated. The residue was diluted with 300 mL of 2-propanol and treated with 4 g of activated charcoal for 30 minutes. The mixture was vacuum filtered through Celite and the solids rinsed with 2×75 mL aliquots of 2-propanol. The filtrates were combined and concentrated, first via rotary evaporation and then under full vacuum pump pressure. The residue was diluted with 250 mL of methanol and re-concentrated, first via rotary evaporation and then under full vacuum pump pressure. The residue was diluted with 250 mL of methanol and hydrogen chloride gas was bubbled into the mixture for 1–2 minutes (5.0 g). The mixture was stirred at room temperature for 2 h and then concentrated via rotary evaporation. The residue was twice diluted with 250 mL of methanol and concentrated, first via rotary evaporation and finally under full vacuum pump pressure (<0.5 mm Hg) to afford 23.91 g of the product (12) as a very light yellow foamy solid (85%): $^1$H NMR ($d_6$-DMSO) d 8.72 (2H, broad s), 3.58 (3H, s), 2.82 (2H, m), 2.49 (3H, s), 2.32 (2H, t), 1.68-1.45 (4H, m) and 1.39-1.21 (2H, m) ppm; $^1$H NMR (CD$_3$OD) d 3.63 (3H, s), 2.97 (2H, t), 2.34 (2H, t), 1.75-1.56 (4H, m) and 1.49-1.31 (2H, m) ppm.

Preparation of N-Methyl-N-(5-Methoxycarbonylpentyl) Biotinamide (13)

To a 500 mL round bottom flask, charged with 9.00 g (36.8 mmol) of biotin (Sigma Chemical Company), 7.93 g (40.5 mmol, 1.1 equiv.) of amine hydrochloride 12, and 200 mL of anhydrous dimethylformamide was added 17 mL of triethylamine (120 mmol) followed by 17.1 g (38.7 mmol, 1.05 equiv.) of benzotriazolyloxytris(dimethylamino) phosphonium hexaphosphonate (BOP, commercially available from Aldrich Chemical Company and Chem-Impex International, Wood Dale, Ill.) coupling agent. The reaction was stirred at room temperature for 13 h and then concentrated. The residue was diluted with 100 mL of 2-propanol and 300 mL of methylene chloride and the resulting mixture was washed with 2×150 mL aliquots of 1N aqueous HCl and then with 150 mL of de-ionized water. The organic phase was dried with anhydrous magnesium sulfate and vacuum filtered. The solids were rinsed with 100 mL of 25% 2-propanol/methylene chloride. The combined filtrates were concentrated. The residue was chromatographed on 9×22 cm of silica gel, eluting with 20% methanol/ethyl acetate. The fractions containing product (13) were combined and concentrated via rotary evaporation. The residue was chromatographed on 7×18 cm of RP-18 silica gel, eluting with 800 mL of 50:50 methanol/water, 1 liter of 55:45 methanol/water and 2 liters of 60:40 methanol/water. The fractions containing product (13) were combined and concentrated, first via rotary evaporation and finally under full vacuum pump pressure (<0.5 mm Hg) to afford 11.58 of the product (13) as a near colorless oil: $^1$H NMR ($d_6$-DMSO) d 6.42 (1H, s), 6.33 (1H, s), 4.29 (1H, m), 4.12 (1H, m), 3.57 (3H, s), 3.22 (2H, t), 3.09 (1H, m), 2.91 and 2.77 (3H, 2 s), 2.81 (1H, dd), 2.57 (1H, d), 2.34-2.19 (4H, m) and 1.70-1.10 (12H, m) ppm; $^1$H NMR (CD$_{3pk\ OD)\ d}$ 4.48 (1H, dd), 4.29 (1H, dd), 3.63 and 3.62 (3H, 2 s), 3.34 (2H, t), 3.20 (1H, m), 3.02 and 2.88 (3H, 2 s), 2.91 (1H, dd), 2.68 (1H, d), 2.43-2.27 (4H, m) and 1.80-1.20 (12H, m) ppm; Thin Layer Chromatography (Visualization with p-aminocinnimaldehyde spray); Silica Gel, $R_f$=0.31 (80/20 ethyl acetate/methanol); RP-18 Silica Gel, $R_f$=0.29 (60/40 methanol/water).

Preparation of N-Methyl-N-(5-Hydroxycarbonylpentyl) Biotinamide (14)

To a 1 liter round bottom flask, charged with 11.58 g (30.0 mmol) of 13 in 100 mL of methanol was added 50 mL of 1N aqueous sodium hydroxide. The mixture was stirred for 2–3 h and then concentrated via rotary evaporation. The residue was transferred to a 250 mL round bottom flask in a total of 75 mL of de-ionized water. With vigorous stirring, the pH of the solution was adjusted to 1.5–2 by addition of 1N aqueous HCl, the product precipitating out as a white solid in the process. The mixture was vacuum filtered. The collected solids were rinsed with 3×50 mL aliquots of ice cold de-ionized water. The solids were air dried for 3 h and then under full vacuum pump pressure (<0.5 mm Hg) for 21 h to afford 10.07 g of the product (14) as a white solid (90%): $^1$H NMR (d$_6$-DMSO) d 6.43 (1H, s), 6.35 (1H, s), 4.30 (1H, m), 4.12 (1H, m), 3.23 (2H, t), 3.10 (1H, m), 2.91 and 2.78 (3H, 2 s), 2.81 (1H, dd), 2.57 (1H, d), 2.30-2.13 (4H, m) and 1.79-1.10 (12H, m) ppm; $^1$H NMR (CD$_3$OD) d 4.48 (1H, dd), 4.29 (1H, dd), 3.35 (2H, t), 3.19 (1H, m), 3.02 and 2.88 (3H, 2 s), 2.91 (1H, dd), 2.68 (1H, d), 2.43-2.23 (4H, m) and 1.83-1.21 (12H, m) ppm; Thin Layer Chromatography (Visualization with p-aminocinnimaldehyde spray); RP-18 Silica Gel, R$_f$=0.50 ($^{60}$/$_{40}$ methanol/water).

Preparation of N-BOC-N,N-Bis-(5-Methoxycarbonylpentyl)amine (15)

To a 500 mL round bottom flask, charged with 6.43 g (29.1 mmol) of di-t-butyl-dicarbonate and 9.00 g (29.1 mmol) of N,N-bis-(5-methoxycarbonylpentyl)-amine hydrochloride (4), was added 125 mL of anhydrous acetonitrile followed by 7.5 mL of triethylamine. The mixture was stirred at room temperature for 22 h and then concentrated via rotary evaporation. The residue was diluted with 300 mL of ethyl acetate and washed with 2×100 mL aliquots of 0.1N aqueous HCl, 100 mL of de-ionized water and 100 mL of 5% aqueous sodium bicarbonate. The organic phase was dried over magnesium sulfate, vacuum filtered and concentrated, first via rotary evaporation and then under full vacuum pump pressure (<0.5 mm Hg) to afford 10.5 g of product (15) as a near colorless oil (97%): $^1$H NMR (d$_6$-DMSO) d 3.57 (6H, s) 3.07 (4H, t), 2.28 (4H, t), 1.60-1.10 and 1.37 (21H, m and s) ppm; Thin Layer Chromatography (Visualization with ninhydrin spray and heat); Silica Gel, R$_f$=0.33 ($^{20}$/$_{80}$ ethyl acetate/hexane); RP-18 Silica Gel, R$_f$=0.17 ($^{70}$/$_{30}$ methanol/water).

Preparation of N-BOC-N,N-Bis-(5-Hydroxycarbonylpentyl)amine (16)

To a 500 mL round bottom flask, charged with 10.5 g of bis-methyl ester 15, was added 75 mL of methanol followed by 75 mL of 1N aqueous sodium hydroxide. The mixture was stirred at room temperature for 16 h and then concentrated via rotary evaporation. The residue was diluted with 75 mL of de-ionized water and the pH of the resultant solution adjusted to 2.0-2.5 by slow addition of approximately 75 mL of 1N aqueous HCl. Then, 200 mL of ethyl acetate was added and the mixture stirred vigorously for 3 minutes. The mixture was transferred to a separatory funnel and the layers separated. The aqueous phase was extracted with 2×150 mL aliquots of ethyl acetate. The organic extracts were combined, dried over anhydrous magnesium sulfate, and vacuum filtered. The filtrates were concentrated, first via rotary evaporation and then under full vacuum pump pressure (<0.5 mm Hg),, to afford 9.52 gof the product as a viscous, nearly colorless oil (98%): $^1$H-NMR (d$_6$-DMSO) d 3.07 (4H, t), 2.28 (4H, t), 1.58-1.10 and 1.37 (21H, m and s) ppm; Thin Layer Chromatography (Visualization with ninhydrin spray and heat); RP-18 Silica Gel, R$_f$=0.44 ($^{70}$/$_{30}$ methanol/water).

Preparation of N-BOC-N,N-Bis-(N',N'-Bis(5-Methoxycarbonylpentyl)-5-Carbamyl pentyl)Amine (17)

To a 1 liter round bottom flask, charged with 9.52 g (27.6 mmol) of bis-acid 16 in 250 mL of anhydrous dimethylformamide, was added 19.0 (61.3 mmol) of N,N-bis-(5-methoxycarbonylpentyl)amine hydrochloride (4) followed by 30 mL of triethylamine. While the mixture was stirred, 25.7 g (58.1 mmol) of BOP was added. The resulting mixture was stirred at room temperature for 14 h and then concentrated via rotary evaporation. The residue was diluted with 750 mL of ethyl acetate and washed with 250 mL of 0.2N aqueous HCl, 100 mL of 0.1N aqueous HCl, 100 mL of de-ionized water, and 2×100 mL aliquots of 5% aqueous sodium bicarbonate. The organic phase was dried over anhydrous magnesium sulfate, vacuum filtered, and concentrated via rotary evaporation. The residue was chromatographed on 9×21 cm of silica gel, eluting first with 70% ethyl acetate/hexane and then with 100% ethyl acetate. The fractions containing product (17) were combined and concentrated via rotary evaporation. The residue was chromatographed on 7×23 cm of RP-18 silica gel, eluting with first with 75:25 methanol/water. The fractions containing product were combined and concentrated, first via rotary evaporation and then under full vacuum pump pressure. The residue was diluted with 500 mL of diethyl ether and the resulting solution was dried with anhydrous magnesium sulfate. The mixture was vacuum filtered and the filtrate was concentrated, first via rotary evaporation and then under full vacuum pump pressure (<0.5 mm Hg), to afford 17.80 g of product (17) as a near colorless, viscous, oil (75%): $^1$H-NMR (d$_6$-DMSO) d 3.57 (12H, s), 3.18 and 3.07 (12H, 2 t's), 2.32-2.16 (12H, m), 1.61-1.09 and 1.37 (45H, m and s) ppm; Thin Layer Chromatography (Visualization with ninhydrin spray and heat); Silica Gel, R$_f$=0.50 (ethyl acetate); RP-18 Silica Gel, R$_f$=0.30 ($^{85}$/$_{15}$ methanol/water).

Preparation of N-BOC-N,N-Bis-(N',N'-Bis(5-Hydroxycarbonylpentyl)-5-Carbamyl pentyl)Amine (18)

To a 500 mL round bottom flask, charged with 7.88 g (9.20 mmol) of the tetramethyl ester (18) in 75 mL of methanol, was added 70 mL of 1N aqueous sodium hydroxide. The mixture was stirred at room temperature for 16 h and then concentrated via rotary evaporation to a thick syrup. The residue was diluted with 50 mL of de-ionized water and, with vigorous stirring, the pH of the solution was adjusted to 2–2.5 by slow addition of approximately 70 mL of 1N aqueous HCl, the product (18) oiling out (one liquid phase separates from another liquid phase) in the process. The mixture was extracted with 200 mL of 3:12-propanol/methylene chloride, and then 3×100 mL aliquots of 3:12-propanol/methylene chloride. The organic extracts were combined, dried over anhydrous magnesium sulfate, filtered and concentrated, first via rotary evaporation and then under full vacuum pump pressure (<0.5 mm Hg) to afford 7.70 g of a near colorless, thick syrup, consisting (by NMR integration) of 6.93 g of the desired product (18, 94%) and 0.77 g of 2-propanol: $^1$H-NMR (d$_6$-DMSO) d 3.18 and 3.07 (12H, 2 t's), 2.37-2.12 (12H, m), 1.60-1.10 and 1.37 (45H, m and s) ppm; Thin Layer Chromatography (Visualization with ninhydrin spray and heat); RP-18 Silica Gel, R$_f$=0.50 ($^{70}$/$_{30}$ methanol/water).

Preparation of N-BOC-Tet-Gal-NAc-1-a-S-C5 Branch (20)

To a 250 mL round bottom flask, charged with 4.05 g (7.38 mmol) of 3,4,6-tri-O-acetyl-N-acetyl-galactosamine-1-a-S[5'-thiopentyl-N-BOC-amine] (11), was added 20 mL of methylene chloride followed by 20 mL of trifluoroacetic acid. The mixture was stirred at room temperature for 15 minutes. The mixture was concentrated via rotary evaporation and the residue was thrice diluted with 75 mL of methylene chloride and re-concentrated to afford 6.27 g of residue, a mixture of desired product (19) and residual trifluoroacetic acid: $^1$H-NMR (CD$_3$OD) d 5.61 (1H, d), 5.41 (1H, dd), 5.01 (1H, dd), 4.62-4.47 (2H, m), 4.11 (2H, d), 2.91 (2H, t), 2.74-2.48 (2H, m), 2.11 (3H, 2s), 2.00 (3H, s), 1.93 and 1.91 (6H, 2 s), and 1.37-1.10 (6H, m) ppm. To a separate 250 mL round bottom flask, charged with 1.33 g of the syrup containing 90% 18 by weight (net 1.20 g, 1.50 mmol), was added 50 mL of anhydrous dimethylformamide. In order to remove residual 2-propanol, the mixture was concentrated first via rotary evaporation and then under full vacuum pump pressure (<0.5 mm Hg). To the residue was added 20 mL of anhydrous dimethylformamide and 10 mL of dry triethylamine. To the resultant, stirred, solution was added a dimethylformamide solution of the crude 19 (in a total of 30 mL of anhydrous dimethylformamide) and the resultant mixture stirred at room temperature for 2 h. The mixture was then concentrated via rotary evaporation. The residue was then diluted with 250 mL of methylene chloride and washed with 2×100 mL aliquots of 1N aqueous HCl, 100 mL of de-ionized water, and then with 100 mL of saturated aqueous sodium bicarbonate. The organic phase was dried over anhydrous magnesium sulfate, vacuum filtered, and concentrated via rotary evaporation. The residue was chromatographed on 5.5×19 cm of RP-18 silica gel, eluting with 250 mL each of 65:35 methanol/water, 70:30 methanol/water, 75:25 methanol/water, and then with 800 mL of 80:20 methanol/water. The fractions containing product were combined, and concentrated, first via rotary evaporation and then under full vacuum pump pressure to afford 3.55 g of a foamy white solid (94%). this material was then chromatographed on 5.5×20 cm of silica gel, eluting with 80:20 ethyl acetate/methanol. The fractions containing only the desired product (20) were combined and concentrated, first via rotary evaporation and then under full vacuum pump pressure (<0.5 mm Hg), to afford 2.83 g of the desired product as a pure white foamy solid (75% ): $^1$H-NMR (CD$_3$OD) d 5.58 (4H, d), 5.42 (4H, dd), 5.01 (4H, dd), 4.63-4.51 (8H, m), 4.20-4.00 (8H, m), 3.35-3.10 (20H, m), 2.73-2.47 (8H, m), 12.32 (4H, t), 2.25-2.08 (20H, m and s), 2.00 (12H, s), 1.93 and 1.91 (24H, 2 s), 1.71-1.20 (69H, m and s) ppm; Thin Layer Chromatography (Visualization with ninhydrin spray and heat); Silica Gel, R$_f$=0.47 (75:25 ethyl acetate/methanol); RP-18 Silica Gel, R$_f$=0.33 ($^{80}$/$_{20}$ methanol/water).

Preparation of N-Methyl-N-(((N",N"-Bis(5-Methoxycarbonylpentyl)-N',N'-Bis-(5-Carbamylpentyl))-5-Carbamylpentyl)Biotinamide(22)

To a 250 mL round bottom flask, charged with 1.50 g (1.75 mmol) of N-BOC-N,N-bis-(N',N'-bis(5-methoxycarbonylpentyl)-5-carbamyl pentyl)-amine (17) in 15 mL of methylene chloride, was added 15 mL of trifluoroacetic acid. The mixture was stirred at room temperature for 15 minutes and then concentrated. The residue was diluted with 50 mL of methylene chloride and then concentrated via rotary evaporation. The residue was then diluted with 50 mL of methanol and re-concentrated via rotary evaporation. The residue was again re-diluted with 50 mL of methylene chloride and re-concentrated, first via rotary evaporation and then under full vacuum pump pressure (<0.5 mm Hg). to the residue was added 30 mL of anhydrous dimethylformamide, 4 mL of dry triethylamine, 715 mg (1.90 mmol) of N-methyl-N-(5-methoxycarbonylpentyl)-biotinamide (13), and finally 840 mg (1.90 mmol) of BOP. The mixture was stirred at room temperature for 3 h and then concentrated via evaporation. The residue was chromatographed on 4.5×18 cm of RP-18 silica gel, eluting with 200 mL each of 55:45 methanol/water, 60:40 methanol/water, 70:30 methanol/water, and 600 mL of 80/20 methanol/water. The fractions containing product were combined and concentrated, first via rotary evaporation and then under full vacuum pump pressure (<0.5 mm Hg), to afford 1.75 g of the product as a near colorless oil (90%): $^1$H-NMR (d$_6$-DMSO) d 6.43 (1H, s), 6.34 (1H, s), 4.29 (1H, m), 4.11 (1H, m), 3.57 (12H, s), 3.29-2.99 (15H, m), 2.90 and 2.78 (3H, 2 s's), 2.81 (1H, dd), 2.55 (1H, d), 2.35-2.12 (16H, m), and 1.65-1.10 (48H, m) ppm; Thin Layer Chromatography (Visualization with p-aminocinnimaldehyde spray); RP-18 Silica Gel, R$_f$=0.48 ($^{85}$/$_{15}$ methanol/water).

Preparation of N-Methyl-N-(((N"N"-Bis(5-Hydroxycarbonylpentyl)-N',N'-Bis-(5-Carbamylpentyl))-5-Carbamylpentyl)Biotinamide(23)

To a 250 mL round bottom flask, charged with 1.75 g (1.58 mmol) of N-methyl-N-(((N",N"-bis-(5-methoxycarbonylpentyl)-N',N'-bis-(5-carbamylpentyl))-5-carbamylpentyl)-biotinamide (22) in 30 mL of methanol, was added 20 mL of 1N aqueous sodium hydroxide. The mixture was stirred at room temperature for 14 h and then concentrated via rotary evaporation. The residue was diluted with 30 mL of de-ionized water and then the vigorously stirred solution was acidified to pH 1.5–2 with the slow addition of approximately 20 mL of 1N aqueous HCl, the product (23) oiling out of solution in the process. The mixture was concentrated via rotary evaporation and the residue was chromatographed on 4.5×18 cm of RP-18 silica gel, eluting with 200 mL each of 55:45 methanol/water, 60:40 methanol/water, 65:35 methanol/water, 70:30 methanol/water and 75:25 methanol/water. The fractions containing product were combined and concentrated, first via rotary evaporation and then under full vacuum pump pressure (<0.5 mm Hg), to give 1.57 g of the product (23) as a glassy solid (95%): $^1$H-NMR (d$_6$-DMSO) d 6.43 (1H, s), 6.35 (1H, s), 4.29 (1H, m), 4.11 (1H, m), 3.29-2.99 (15H, m), 2.90 and 2.78 (3H, 2 3's), 2.81 (1H, dd), 2.55 (1H, d), 2.30-2.12 (16H, m), and 1.65-1.10 (48H, m) ppm; Thin Layer Chromatography (Visualization with p-aminocinnimaldehyde spray); RP-18 Silica Gel, R$_f$=0.56 ($^{80}$/$_{20}$ methanol/water.)

Preparation of Hexadecyl-N-Acetyl-Galactosamine-Biotin Cluster (25)

To a 100 mL round bottom flask, charged with 790 mg (0.313 mmol) of the N-BOC-Tet-Gal-NAc-1-a-S-C5 Branch (20), was added 10 mL of methylene chloride followed by 10 mL of trifluoroacetic acid. The mixture was stirred at room temperature for 15 minutes and then concentrated via rotary evaporation. The residue was diluted with 150 mL of methylene chloride and washed with 2×100 mL aliquots of saturated aqueous sodium bicarbonate. The organic phase was dried over magnesium sulfate, vacuum filtered and then concentrated, first via rotary evaporation and then under full pump pressure (<0.5 mm Hg), to afford 690 mg of the product (24) as a foamy off-white solid (91%).

It should be noted that the product (24) is a universal reagent which may be used to derivatize a moiety to be cleared following administration thereof. Note that this compound may be used to derivatize any moiety that bears a functional group reactive with an amine group. Alternatively, product (24) may be modified by reaction with a heterobifunctional group or otherwise to afford an alternative functional group with which to bind this universal reagent to a moiety to be cleared. Use of heterobifunctional agent or other means to alter reactive groups is within the ordinary skill in the art. Functional groups which may be employed in this aspect of this invention include active esters, maleimides, alkyl halides, hydrazides, thiols, imidates, aldehydes or the like.

In practice of this aspect of the present invention, a moiety to be cleared after administration (such as a relatively rapidly accreting imaging agent) may be derivatized to incorporate the sugar cluster of product (24). In this manner, the background of the resulting image will be improved in that the imaging agent will accrete to target sites or be cleared via Ashwell receptor recognition of the component contributed by product (24). Thus, circulating imaging agent will be cleared, thus eliminating the background and improving the image.

In a separate 100 mL round bottom flask, charged with 60 mg (0.057 mmol) N-methyl-N-(((N"N"-bis-(5-hydroxycarbonylpentyl)-N',N'-bis-(5-carbamylpentyl))-5-carbamylpentyl)-biotinamide (23), was added 10 mL of anhydrous dimethylformamide. The mixture was concentrated via rotary evaporation, to drive off any residual moisture. To the residue was added 3 mL of anhydrous dimethylformamide and 300 mL of dry diisopropylethylamine followed by 113 mg (0.255 mmol) of BOP. The mixture was stirred at room temperature for 10 minutes and then the amine 24, in a total of 5 mL of anhydrous dimethylformamide was added. The mixture was stirred at room temperature for 3 h and then an additional 20 mg (0.045 mmol) of BOP was added and the mixture was stirred at room temperature for 14 h more. The mixture was concentrated via rotary evaporation and then diluted with 50 mL of methanol and 50 mL of de-ionized water. The resultant mixture was treated with 10 g of AG-1 X8 anion exchange resin (BioRad; Hydroxide form, 2.6 mequiv./g) and stirred at room temperature for 18 h. The mixture was then vacuum filtered. The residue was rinsed with 50 mL of de-ionized water and then with 50 mL of methanol. The filtrates were combined and concentrated via rotary evaporation. The residue was chromatographed on 3.5×16 cm of RP-18 silica gel, eluting with 100 mL each of 50:50 methanol/water, 55:45 methanol/water, 60:40 methanol/water, 65:35 methanol/water, and 70:30 methanol/water. The fractions containing product were combined and concentrated, first via rotary evaporation and then under full vacuum pump pressure (<0.5 mm Hg) to give 470 mg of partially purified product. This material was further purified on a preparative polyhydroxyethyl aspartamide HPLC column (2.5×30 cm; PolyLC Inc., Columbia Md.), eluting with 70/30 acetonitrile/water at 13 ml/min. The fractions containing product were combined and concentrated, first via rotary evaporation and then under full vacuum pump pressure (<0.5 mm Hg). The residue was diluted with 5–10 mL of de-ionized water, frozen to −70° C., and lyophilized to afford 177 mg of the product (25) as a white solid (36%): $^1$H-NMR (CD$_3$OD) d 5.54 (16H, d), 4.55–4.25 (18H, m), 3.90 (16H, m), 3.80–3.65 (48H, m), 3.45–2.80 (99H, m), 2.65–2.45 (33H, m), 2.45–2.27 (32H, m), 2.27–2.05(32H, m), 1.97 (48H, s), and 1.80–1.20 (288H, m) ppm; Thin Layer Chromatography (Visualization with p-aminocinnimaldehyde spray or p-anisaldehyde spray and heat); RP-18 Silica Gel, R$_f$=0.43 (75/25 methanol/water); Mass Spectrometry—Expected M+H=8652.5 amu, Actual M+H=8657 amu.

B. Preparation of 4-N-AcetylGalactosamine-Biotin-CCA (alpha-oxygen) Corresponding to Compound 28 in FIG. 4.

Preparation of 3,4,6-Tri-O-Acetyl-N-Acetyl-Galactosamine-1-a-O-[N'-Methyl-4'-N'-Butyl-Trifluoroacetamide] (26)

To a 25 mL round bottom flask, charged with 1.00 g (2.57 mmol) of 1-b, 3, 4, 6-tetra-O-acetyl-N-acetyl-galactosamine (7) and 767 (3.85 mmol, 1.50 equiv) N-methyl-N-(4-hydroxybutyl)-trifluoroacetamide (4-(N-Methyl-trifluoroacetamido)-1-butanol discussed in Example IV) in 10 mL of dry nitromethane, was added 325 mL (2.64 mmol, 1.03 equiv) of boron trifluoride etherate. The mixture was stirred at 101° C. for 2 h and then concentrated via rotary evaporation. The residue was diluted with 75 mL of methylene chloride and washed with 50 mL of 0.1 N aqueous HCl. The organic phase was dried over magnesium sulfate, vacuum filtered, and the filtrate concentrated via rotary evaporation. The residue was chromatographed on 3.5×18 cm of silica gel, eluting first with 10% acetone/methylene chloride and then with 15% acetone/methylene chloride. The fractions containing product were combined and concentrated, first via rotary evaporation and then under full vacuum pump pressure (<0.5 mm Hg), to afford 453 mg of the product (26) as a foamy white solid (36%): $^1$H-NMR (d$_6$-DMSO) d 7.98 (1H, d), 5.31 (1H, d), 5.01 (1H, dd), 4.82 (1H, d), 4.27–4.10 (2H, m), 4.10–3.93 (2H, m), 3.60 (1H, m), 3.49–3.35 (3H, m), 3.09 and 2.96 (3H, q and s), 2.10 (3H, s), 1.99 (3H, s), 1.90 (3H, s), 1.79 (3H, s), 1.71–1.42 (4H, m) ppm.

Preparation of N-Acetyl-Galactosamine-1-a-O-[N'-Methyl-4'-Butylamine] (27)

To a 250 mL round bottom flask, charged with 12.5 g of AG-1 X8 anion exchange resin (BioRad; Hydroxide form, 2.6 mequiv/g) and 50 mL of de-ionized water was added 830 mg (1.51 mmol) of the starting material (26) in 50 mL of methanol. The mixture was stirred at room temperature for 22 h. The mixture was then vacuum filtered. The resin was rinsed with 50 mL of de-ionized water and 50 mL of methanol. The filtrates were combined and concentrated, first via rotary evaporation and then under full vacuum pump pressure (<0.5 mm Hg), to afford 463 mg of the product (27) as a pale yellow oil (96%): $^1$H-NMR (D$_2$O) d 4.83 (1H, d), 4.07 (1H, dd), 3.93–3.80 (3H, m), 3.75–3.57 (3H, m), 3.49–3.36 (1H, m), 2.55 (1H, t), 2.30 (3H, s), 1.97 (3H, s), and 1.65–1.42 (4H, m) ppm.

Preparation of 1-a-O-Tetra-N-Acetyl Galactosamine Biotin Cluster Agent (28)

To a 25 mL round bottom flask, charged with 100 mg (0.0949 mmol) of N-methyl-N-(((N"N"-bis-(5-hydroxycarbonylpentyl)-N',N'-bis-(5-carbamylpentyl))-5-carbamylpentyl)-biotinamide (23), was added 140 mg (0.457 mmol, 4.8 equiv) of amine 27 in 5 ml of anhydrous dimethylformamide followed by 0.5 mL of dry triethylamine and finally 190 mg (0.430 mmol, 4.5 equiv) of BOP. The mixture was stirred at room temperature for 19 h and then concentrated via rotary evaporation. The residue was chromatographed on 2.5×15 cm of RP-18 silica gel, eluting with 50:50 methanol/water, 55:45 methanol/water, and 60:40 methanol/water. The fractions containing product were combined and concentrated, first rotary evaporation and then under full vacuum pump pressure (<0.5 mm Hg). The residue was chromatographed on 2.5×18 cm of silica gel, eluting with methanol, 5:95 water/methanol, and 10:90 water/methanol. The fractions containing product were combined and concentrated, first via rotary evaporation and then under full vacuum pump pressure (<0.5 mm Hg). The residue was diluted with 7 mL of de-ionized water, frozen to −70° C., and lyophilized to afford 158 mg of the product (28) as a fluffy white solid (75%): $^1$H-NMR (D$_2$O) d 4.82 (4H, m), 4.54 (4H, dd), 4.35 (4H, dd), 4.07 (4H, dd), 3.95–3.78 (12H, m), 3.72–3.57 (12H, m), 3.48–3.18 (23H, m), 2.99–2.80 (16H, 2 s's and dd), 2.70 (1H, d), 2.43–2.25 (16H, m), 1.98 (12H, s), and 1.75–1.12 (64H, m) ppm.

C. Preparation of 4-N-AcetylGalactosamine-Biotin-CCA (beta-oxygen) Corresponding to Compound 31 in FIG. 5.

Preparation of 3,4,6-Tri-O-Acetyl-N-Acetyl-Galactosamine-1-b-O-[N'-Methyl-4'-N'-Butyl-Trifluoroacetamide] (29)

To a 100 mL round bottom flask, charged with 1.79 g (6.42 mmol) of trityl chloride and 880 mg (6.46 mmol) of zinc chloride, was added a solution of 2.10 g (5.47 mmol) of 1-a-chloro, 3, 4, 6-tetra-O-acetyl-N-acetyl-galactosamine (8) and 1.28 g (6.43 mmol) of N-methyl-N-(4-hydroxybutyl)-trifluoracetamide in 30 mL of dry methylene chloride. The mixture was stirred at room temperature for 3 h and then concentrated via rotary evaporation. The residue was diluted with 100 mL of ethyl acetate and washed with 50 mL of saturated aqueous sodium bicarbonate. The organic phase was dried over magnesium sulfate, vacuum filtered and concentrated via rotary evaporation. The residue was chromatographed on 4.5×19 cm of silica gel, eluting first with 10% acetone/methylene chloride, then with 15% acetone/methylene chloride, and finally with 20% acetone/methylene chloride. The fractions containing product were combined and concentrated, first via rotary evaporation and then under full vacuum pump pressure (<0.5 mm Hg), to afford 1.00 g of the product (29) as a white foamy solid (34%): $^1$H-NMR (d$_6$-DMSO) d 7.80 (1H, d), 5.20 (1H, d), 4.95 (1H, dd), 4.48 (1H, d), 4.02 (3H, s), 3.90 (1H, m), 3.73 (1H, m), 3.50–3.35 (3H, m), 3.08 and 2.93 (3H, q and s), 2.10 (3H, s), 1.99 (3H, s), 1.89 (3H, s), 1.75 (3H, s), and 1.68–1.35 (4H, m) ppm.

Preparation of N-Acetyl-Galactosamine-1-b-O-[N-Methyl-4'-Butylamine] (30)

To a 250 mL Erlenmeyer flask, charged with 20 g of AG-1 X8 resin (BioRad; Hydroxide form; 2.6 mequiv/g) and 50 mL of de-ionized water, was added 1.55 g (2.93 mmol) of 3,4,6-tri-O-acetyl-N-acetyl-galactosamine-1-b-O-[N'-methyl-4'-N'-butyl-trifluoroacetamide] (29) in 30 mL of methanol. The mixture was stirred at room temperature for 15 h and then vacuum filtered. The resin was rinsed with 50 mL of de-ionized water and then with 50 mL of methanol. The filtrates were combined and concentrated, first via rotary evaporation and then under full vacuum pump pressure (<0.5 mm Hg), to afford 880 mg of the product (30) as an off-white foamy solid (98%): $^1$H-NMR (D$_2$O) d 4.41 (1H, d), 3.95–3.50 (8H, m), 2.63 (2H, t), 2.38 (3H, s), 2.00 and 1.63–1.45 (4H, m) ppm.

Preparation of 1-b-O-Tetra-N-Acetyl Galactosamine Biotin Cluster Agent (31)

To a 25 mL round bottom flask, charged with 100 mg (0.0949 mmol) of N-methyl-N-(((N"N"-bis(5-hydroxycarbonylpentyl)-N',N'-bis-(5-carbamylpentyl))-5-carbamylpentyl)biotinamide (23) and 140 mg (0.457 mmol) of N-acetyl-galactosamine-1-b-O-[N-methyl-4'-butylamine] (30) in 5 mL of anhydrous dimethylformamide, was added 0.5 mL of dry triethylamine and followed by 192 mg (0.434 mmol) of BOP. The mixture was stirred at room temperature for 2 h and then concentrated. The residue was chromatographed on 2.5×16 cm of RP-18 silica gel, eluting with 100 mL each of 50:50 methanol/water and 55:45 methanol/water, and with 150 mL of 60:40 methanol/water. The fractions containing product were combined and concentrated, first via rotary evaporation and then under full vacuum pump pressure (<0.5 mm Hg). The residue was chromatographed on 2.5×17 cm of silica gel, eluting with methanol, then with 95.5 methanol/water, and finally with 90:10 methanol/water. The fractions containing product were combined and concentrated, first via rotary evaporation and then under full vacuum pump pressure (<0.5 mm Hg). The residue was dissolved in 8 mL of de-ionized, water frozen to −70° C., and lyophilized to afford 156 mg of the product (31) as a fluffy white solid (75%): $^1$H-NMR (D$_2$O) d 4.54 (1H, dd), 4.42–4.31 (5H, d and m), 3.95–3.45 (32H, m), 3.43–3.15 (23H, m), 3.03–2.82 (16H, 2 s's and dd), 2.71 (1H, d), 2.43–2.26 (16H, m), 1.96 (12H, s), 1.70–1.15 (64H, m) ppm.

D. Preparation of 4-N-AcetylGalactosamine-Biotin-CCA (beta-sulfur) Corresponding to Compound 36 in FIG. 6.

Preparation of N-BOC-N-Methyl-4-Aminobutanol (32)

To a 250 mL round bottom flask, charged with 3.00 g (28.5 mmol) of N-methyl-4-aminobutanol in 75 mL of dioxane, was added 5 mL of triethylamine (35.4 mmol) followed by 7.85 g (31.9 mmol) of BOC-ON, 2-(tert-butoxycarbonyloxyimino)-2-phenylacetonitrile. The mixture was stirred at room temperature for 20 h and then concentrated via rotary evaporation. The residue was chromatographed on silica gel, eluting first with 20% ethyl acetate/hexane, then with 40% ethyl acetate/hexane, and finally with 75% ethyl/hexane. The fractions containing product were combined and concentrated via rotary evaporation to afford 4.85 g of the product (32) as a near colorless oil (84%): $^1$H-NMR (CDCl$_3$) d 3.65 (2H, t), 3.23 (2H, t), 2.81 (3H, s), 1.67–1.45 (4H, m), and 1.42 (9H, s) ppm.

Preparation of N-BOC-N-Methyl-4-Aminobutyl Toluenesulfonate (33)

To a 500 mL round bottom flask, charged with 4.75 g (23.4 mmol) of N-BOC-N-methyl-4-aminopentanol (32) in 150 mL of methylene chloride, was added 5.25 g (27.5 mmol) of toluenesulfonyl chloride and 7.0 mL (49.6 mmol) of triethylamine. The mixture was stirred at room temperature for 24 h and then washed with 3×75 mL aliquots of 1 N aqueous HCl. The organic phase was dried over anhydrous magnesium sulfate, vacuum filtered, and concentrated via rotary evaporation. The residue was chromatographed on silica gel, eluting first with 20% ethyl acetate/hexane and then with 30% ethyl acetate/hexane. The fractions containing product (33) were combined and concentrated via rotary evaporation to afford 6.95 g of the product as a very pale yellow oil (83%): $^1$H-NMR (CDCl$_3$) d 7.78 (2H, d), 7.31 (2H, d), 4.03 (2H, t), 3.15 (2H, t), 2.86 (3H, s), 2.42 (3H, s), 1.73–1.47 (4H, m), and 1.41 (9H, s) ppm.

Preparation of N-Acetyl-Galactosamine-1-b-S-[N'-BOC-N'-Methyl-4'-Butylamine] (34)

To a 250 mL round bottom flask, charged with 7.0 g (15.8 mmol) of 3,4,6-tri-O-acetyl-N-acetyl-galactosamine-1-b-pseudothiourea hydrochloride (9), 2.6 g of potassium carbonate (18.8 mmol), and 1.65 g (15.9 mmol) of sodium hydrosulfite in 90 mL of methanol, was added 6.00 g (16.7 mmol) of N-BOC-N-methyl-4-Aminobutyl-toluenesulfonate (33) in 20 mL of methanol. The mixture was stirred at room temperature for 20 h and then concentrated via rotary evaporation. The residue was chromatographed on RP-18 silica gel, eluting first with 40:60 methanol/water, then with 45:55 methanol/water, then with 50:50 methanol/water, then with 55:45 methanol/water, and finally with 60:40 methanol/water. The fractions containing product were combined and concentrated, first via rotary evaporation and then under full vacuum pump pressure (<0.5 mm Hg), to afford 2.18 g of the product (34) as an off-white solid (33%): $^1$H-NMR (D$_2$O) d 4.47 (1H, d), 3.95–3.82 (2H, m), 3.77–3.57 (4H, m), 3.20 (2H, t), 2.82–2.55 (5H, s and m), 1.97 (3H, s), 1.67–1.45 (4H, m), and 1.38 (9H, s) ppm.

Preparation of N-BOC-Tet-Gal-NAc-1-b-S-C4-N-Me Branch (35)

To a 25 mL round bottom flask, charged with 679 mg (1.61 mmol) of (34), was added 10 mL of trifluoroacetic acid. The mixture was stirred at room temperature for 15 minutes and then concentrated via rotary evaporation. The residue was twice diluted with 10 mL of methanol and then re-concentrated via rotary evaporation.: $^1$H-NMR D$_2$O) d 4.47 (1H, d), 3.95–3.82 (2H, m), 3.78–3.57 (4H, m), 2.97 (2H, t), 2.78–2.58 (5H, s and m), 1.95 (3H, s), and 1.80–1.52 (4H, m), ppm. To a 50 mL round bottom flask, charged with 270 mg (0.337 mmol) of N-BOC-N,N-bis-(N,N'-bis(5-hydroxycarbonylpentyl)-5-carbamyl pentyl)amine (18), was added 1 mL of triethylamine along with the residue in the 25 mL round bottom flask in 15 mL of anhydrous dimethylformamide followed by 670 mg (1.52 mmol) of BOP. The mixture was stirred at room temperature for 4 h and then concentrated via rotary evaporation. The residue was chromatographed on RP-18 silica gel, eluting first with 50:50 methanol/water, then with 55:45 methanol/water, then with 60:40 methanol/water, and finally with 65:35 methanol/water. The fractions containing product were combined and concentrated, first via rotary evaporation and then under full vacuum pump pressure (<0.5 mm Hg), to afford 300 mg of the product (35) as a white foamy solid (44%): H-NMR (D$_2$O) d 4.47 (4H, d), 3.98–3.83 (8H, m), 3.78–3.56 (16H, m), 3.43–3.08 (20H, m), 2.99 and 2.84 (12H, 2 s's), 2.80–2.55 (8H, m), 2.41–2.25 (12H, m), 1.97 (12H, s), and 1.75–1.13 and 1.38 (61H, m and s) ppm.

Preparation of 1-b-S-Tetra-N-Acetyl Galactosamine Biotin Cluster Agent (36)

To a 25 mL round bottom flask, charged with 100 mg of 35 was added 10 mL of trifluoroacetic acid. The mixture was stirred at room temperature for 10 minutes and then concentrated via rotary evaporation. The residue was twice diluted with 10 mL of methanol and re-concentrated, first via rotary evaporation and then under full vacuum pump pressure (<0.5 mm Hg). The residue was diluted with 5 mL of anhydrous dimethylformamide and then treated with 25 mg (0.067 mmol) of N-methyl-N-(5-hydroxycarbonylpentyl)biotinamide (14), 300 mL of dry triethylamine, and then with 30 mg (0.068 mmol) of BOP. The mixture was stirred at room temperature for 2 h and then concentrated via rotary evaporation. The residue was chromatographed on RP-18 silica gel, eluting first with 50:50 methanol/water, then with 55:45 methanol/water, then with 60:40 methanol/water, and finally with 65:35 methanol/water. The fractions containing product were combined and concentrated, first via rotary evaporation and then under full vacuum pump pressure (<0.5 mm Hg). The residue was diluted with 5 mL of de-ionized water, frozen to −70° C. and lyophilized to afford 77 mg of the product (36) as a white puffy solid (77%): H-NMR (D$_2$O) d 4.53 (1H, dd), 4.47 (4H, d), 4.34 (1H, dd), 3.98–3.80 (8H, m), 3.77–3.54 (16H, m), 3.40–3.08 (23H, m), 2.98 and 2.82 (15H, 2 s's), 2.91 (1H, dd), 2.78–2.55 (9H, m), 2.40–2.23 (16H, m), 1.93 (12H, s), and 1.72–1.11 (64H, m) ppm.

E. Preparation of 4-N-AcetylGalactosamine-Biotin-CCA (alpha-sulfur) Corresponding to Compound 41 in FIG. 7.

Preparation of 3,4,6-Tri-O-Acetyl-N-Acetyl-Galactosamine-1-b-S-[N'-Methyl-4'-N'-Butyl-Trifluoroacetamide] (38)

To a 100 mL round bottom flask, charged with 2.00 g (4.46 mmol) of 3,4,6-tri-O-acetyl-N-acetyl-galactosamine-1-b-pseudothiourea hydrochloride (9), 690 mg of potassium carbonate (4.99 mmol) of 940 mg (9.04 mmol) of sodium hydrosulfite was added 25 mL of de-ionized water followed by 25 mL of methylene chloride. The mixture was stirred at room temperature for 1 h and the layers then separated. The aqueous phase was extracted with 3×75 mL aliquots of methylene chloride. The organic extracts were combined, dried over sodium sulfate, filtered and then concentrated via rotary evaporation: $^1$H-NMR (d$_6$-DMSO) d 7.95 (1H, d), 5.28 (1H, d), 4.96 (1H, dd), 4.73 (1H, dd), 4.13–3.89 (4H, m), 3.33 (1H, d), 2.10 (3H, s), 1.99 (3H, s), 1.89 (3H, s), and 1.79 (3H, s) ppm. The residue, 1.03 g of thiol (37), was diluted with 20 mL, of methanol and treated with 412 mg (2.98 mmol) of potassium carbonate, 619 mg (5.95 mmol) of sodium hydrosulfite and 2.00 g (5.66 mmol) of N-methyl-4-trifluoroacetamido-butyltoluenesulfonate (1-(p-Toluenesulfonyloxy)-4-(N-methyl-trifluoroacetamido) butane discussed in Example IV). The mixture was stirred at room temperature for 2 h and then concentrated via rotary evaporation. The residue was diluted with 75 mL of methylene chloride and washed with 50 mL, of 0.1 N aqueous HCl. The organic phase was dried over magnesium sulfate, vacuum filtered and concentrated via rotary evaporation. The residue was chromatographed on silica gel, eluting first with 10% acetone/methylene chloride and then with 15% acetone/methylene chloride. The fractions containing product were combined and concentrated, first via rotary evaporation and then under full vacuum pump pressure (<0.5 mm Hg), to afford 683 mg of the product (38) as a foamy white solid (26%): $^1$H-NMR (d$_6$DMSO) d 7.88 (1H, d), 5.26 (1H, 2 d), 4.96 (1H, dd), 4.60 (1H, d), 4.09–3.92 (4H, m), 3.39 (2H, t), 3.08 and 2.93 (3H, q and s), 2.77–2.50 (2H, m), 2.10 (3H, s), 1.99 (3H, s), 1.89 (3H, s), 1.77 (3H, s), 1.71–1.42 (4H, m) ppm.

Preparation of 3,4,6-Tri-O-Acetyl-N-Acetyl-Galactosamine-1-a-S-[N'-Methyl-4'-N'-Butyl-Trifluoroacetamide] (39)

To a 50 mL round bottom flask, charged with 620 mg (1.17 mmol) of the 3,4,6-tri-O-acetyl-N-acetyl-galactosamine-1-b-S-[N'-methyl-4'-N'-butyl-trifluoroacetamide] (38) in 10 mL of dry nitromethane was added 145 mL of borontrifluoride etherate (1.17 mmol). The mixture was stirred at 100° C. for 3 h and then allowed to sit at room temperature for 3 weeks. The mixture was concentrated via rotary evaporation. The residue was diluted with 75 mL of methylene chloride and washed with 1 N aqueous HCl. The residue was chromatographed on silica gel, eluting first with 10% acetone/methylene chloride and then with 15% acetone/methylene. The fractions containing product were combined and concentrated, first via rotary evaporation and then under full vacuum pump pressure (<0.5 mm Hg), to afford 254 mg of the product (39) as a very pale yellow oil (41%): $^1$H-NMR (d$_6$-DMSO) d 8.17 (1H, d), 5.56 (1H, 2 d's), 5.33 (1H, d), 4.88 (1H, dd), 4.49–4.29 (2H, m), 4.03 (2H, d), 3.38 (2H, t), 3.08 and 2.93 (3H, q and s), 2.55 (2H, m), 2.09 (3H, s), 1.97 (3H, s), 1.90 (3H, s), 1.79 (3H, s), 1.72–1.41 (4H, m) ppm.

Preparation of N-Acetyl-Galactosamine-1-a-S-[N-Methyl-4'-Butylamine] (40)

To a 250 mL Erlenmeyer flask, charged with 15 g of AG-1 X8 anion exchange resin (BioRad; Hydroxide form, 2.6 mequiv/g) and 60 mL of de-ionized water, was added 245 mg (0.450 mmol) of tri-O-acetyl-N-acetyl-galactosamine-1-a-S-[N'-methyl-4'-N'-butyl-trifluoroacetamide] (39) in 40 mL of methanol. The mixture was stirred at room temperature for 22 h and then vacuum filtered. The resin was rinsed with 50 mL of de-ionized water and then with 50 mL of methanol. The filtrates were combined and concentrated, first via rotary evaporation and then under full vacuum pump pressure (<0.5 mm Hg), to afford 143 mg of the product (40) as a pale yellow solid (99%): $^1$H-NMR (D$_2$O) d 5.43 (1H, d 4.32–4.17 (2H, m), 3.91 (1H, d), 3.77 (1H, dd), 3.70 (2H, d), 2.70–2.45 (4H, m), 2.29 (3H, s), 1.96 (3H, s), 1.66–1.42 (4H, m) ppm.

Preparation of 1-a-S-Tetra-N-Acetyl Galactosamine Biotin Cluster Agent (41)

To a 50 mL round bottom flask, charged with 80 mg (0.0759 mmol) of N-methyl-N-(((N"N"-bis(5-hydroxycarbonylpentyl)-N',N'-bis-(5-carbamylpentyl))-5-carbamylpentyl)biotinamide (23) in 10 mL of anhydrous dimethylformamide, was added 123 mg (0.379 mmol) of N-acetyl-galactosamine-1-a-S-[N-methyl-4'-butylamine] (40) and 0.5 mL of dry triethylamine. The mixture was stirred at room temperature for 10 minutes and then 152 mg (0.344 mmol) of BOP was added. The mixture was stirred at room temperature for 2 h and then concentrated. The residue was chromatographed on 2.5×20 cm of RP-18 silica gel, eluting with 100 mL of 50:50 methanol/water, 100 mL of 55:45 methanol/water, and then with 200 mL of 60:40 methanol/water. The fractions containing product were combined and concentrated, first via rotary evaporation and then under full vacuum pump pressure (<0.5 mm Hg). The residue was diluted with 6 mL of de-ionized water, water frozen to −70° C., and lyophilized to afford 107 mg of the product (41) as a fluffy white solid (62%): $^1$H-NMR (D$_2$O) d 5.42 (4H, t), 4.53 (1H, dd), 4.38–4.14 (9H, m), 3.90 (4H, d), 3.80–3.63 (12H, d and dd), 3.45–3.15 (23H, m), 3.00–2.79 (16H, 2 s's and dd), 2.73–2.45 (9H, d and m), 2.40–2.25 (16H, m), 1.95 (12H, s), 1.75–1.12 (64H, m) ppm.

EXAMPLE VII

Second Generation CCA Evaluation

A. Four Sugar Construct Evaluation.

To determine the optimal properties of second generation CCAs, a series of four sugar-containing CCAs were prepared substantially as described above and tested in three sets (designated a, b and c) as follows: BALB/c female mice (20–25 g) were injected i.v. with 120 micrograms of NR-LU-10-streptavidin conjugate radiolabeled with I-125, and blood was serially collected from n=3 mice. The clearance of the conjugate from the blood was measured in these control mice. Separate groups of mice were injected with either 120 or 12 micrograms of radiolabeled monoclonal antibody-streptavidin conjugate which had been precomplexed with the 4-galactose-biotin or 4-N-acetylgalactosamine-biotin CCAs by mixing the biotin analog at a 20-fold molar excess with the antibody conjugate. Generally, both doses of precomplexed conjugate showed extremely rapid clearance from the blood, relative to the antibody conjugate control.

The test results for clearance study sets a), b) and c) (120 microgram doses only) may be summarized as follows:

| Number | Sugar Unit | 4 hour Conjugate Level (% ID/g) |
|---|---|---|
| 1 | Gal-β-S-(CH$_2$)$_4$-N(Me) | a) 31.5 ± 1.0% |
| 2 | Gal-NAc-β-S-(CH$_2$)$_4$-N(Me) | a) 22.6 ± 0.6% |
| 3 | Gal-NAc-β-O-(CH$_2$)$_4$-N(Me) | a) 19.8 ± 0.9% |
| 4 | Gal-NAc-α-O-(CH$_2$)$_4$-N(Me) | a) 14.9 ± 1.9% |
| 5 | Gal-NAc-α-S-(CH$_2$)$_4$-N(Me) | b) 4.5 ± 1.2% |
| 6 | Gal-NAc-α-O-(CH$_2$)$_4$-NH | a) 11.3 ± 1.4% |
| 7 | Gal-NAc-α-O(CH$_2$)$_2$ONH(CH$_2$)$_2$NH | a) 16.0 ± 2.5% |
| 8 | Gal-NAc-α-O-(CH$_2$)$_6$-NH | a) 8.1 ± 0.2% and 6.7 ± 0.2% @ 24h b) 6.2 ± 0.4% and 6.5 ± 0.4% @ 24h |
| 9 | Gal-NAc-α-O-(CH$_2$)$_8$-NH | b) 4.4 ± 0.7% |
| 10 | Gal-NAc-α-O-(CH$_2$)$_6$-N(Me) | b) 8.1 ± 0.6% |
| 11 | Gal-NAc-α-S-(CH$_2$)$_6$-NH | c) ~3% |
| 12 | Gal-NAc-α-S-(CH$_2$)$_8$-NH | c) ~3%; poor aqueous solubility |

NOTE: All of these constructs were bound to aminocaproyl-N(Me)-biotin via a cluster backbone characterized by two sets of two branches, as follows: ((Sugar Unit)$_2$NCO—(CH$_2$)$_5$)$_2$—N—. "Gal-NAc" constitutes N-acetylgalactosamine.

The tested 4-sugar CCAs were prepared substantially as set forth above.

The structures of compounds 11 and 12 are included below for illustrative purposes.

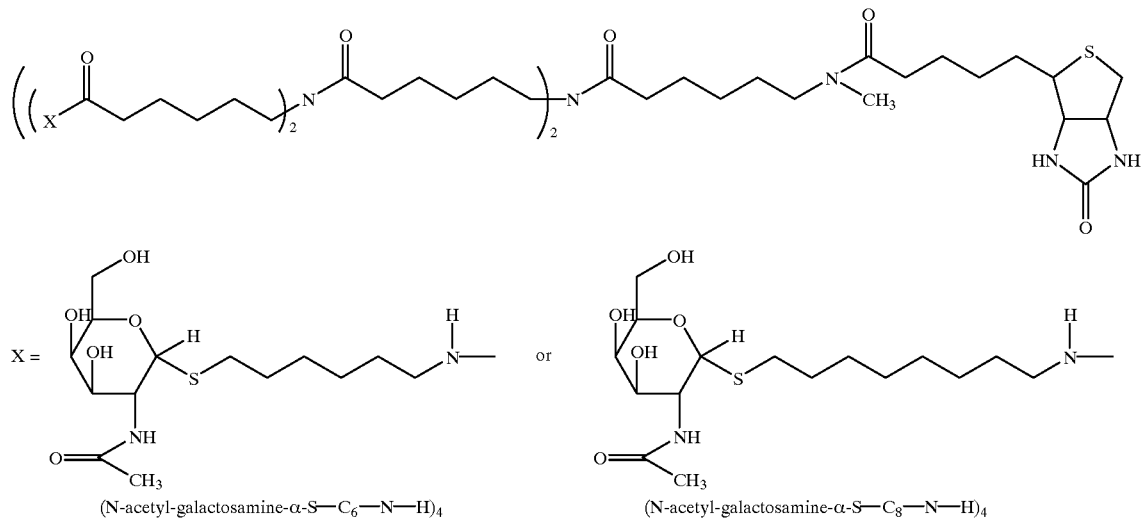

(N-acetyl-galactosamine-α-S—C$_6$—N—H)$_4$    (N-acetyl-galactosamine-α-S—C$_8$—N—H)$_4$ The clearing abilities of compounds 11 and 12 were roughly equivalent to or better than the first generation CCA construct, (Gal-1-β-S—(CH$_2$)$_4$—N(Me))$_{16}$-aminocaproyl-N(Me)-biotin, which is designated (Galactosyl)$_{16}$-LC-biotin in Example V.

B. 16 N-Acetylgalactosamine Construct Evaluation.

The purpose of this study was to investigate and compare the clearing ability and impact on subsequently administered active agent biodistribution of equimolar doses of 3 CCAs containing 16 N-acetylgalactosamines in comparison to a 32-galactose CCA with a (N-methylaminocaproyl)$_2$ linker to biotin:

| Sugar Unit | Linker to Biotin |
| --- | --- |
| galNAc-α-S-C$_6$-NH | N-methylaminocaproyl |
| galNAc-β-S-C$_4$-NMe | N-methylaminocaproyl |
| gal-β-S-C$_4$-NMe | N-methylaminocaproyl |

Nude mice bearing s.c. SW-1222 xenografts (n=4 per group per timepoint) were injected at t=0 with 400 μg (1.9 nmol) of NR-LU-10-streptavidin conjugate labeled with PIP-I-125 in accordance with known procedures therefore. After 24 hours, animals were injected with 22.5 nmol (180–360 μg) of each CCA. Four hours later, a tumor-saturating 15 μg (18.6 nmol) dose of In-111-DOTA-biotin was administered. Animals were bled and euthanized by cervical dislocation at 2 and 24 hours post In-111-DOTA-biotin injection. Blood, tail, lung, liver, spleen, stomach, kidney, intestines and tumor were counted in a dual-channel gamma counter to establish the tissue concentrations of In-111 and I-125.

Results of this experiment indicated that the 32-galactose CCA afforded the best clearance (lowest I-125 and In-111 levels in non-tumor tissues). The two N-acetylgalactosamine CCAs performed next best and approximately equivalently. The 16-galactose CCA was the poorest at clearing NR-LU-10-streptavidin, resulting in blood levels of DOTA-biotin that were double those of the N-acetylgalactosamine CCAs and 9 times those of the 32-galactose CCA. As expected with a saturating dose of In-111-DOTA-biotin, tumor targeting of In-111 was equivalent for all groups of animals. Negligible CCA compromise of pretargeted NR-LU-10-streptavidin was observed at the administered doses. Use of the 32-galactose construct resulted in tumor:blood ratios that were 2–4 fold better than for the other tested CCAs and the lowest nadir of NR-LU-10-streptavidin blood concentration. The performance of the 32-galactose CCA was hypothesized to result from either or both of the following: (1) increased sugar density; and (2) the extended linker arm between the cluster and biotin. The extender experimentation is discussed below in Experiment E.

C. Impact of Timing Between CCA and Active Agent Administrations.

This parameter was investigated using a 16-N-acetylgalactosamine construct characterized by a sugar unit of galNAc-α-S-C$_6$-NH and a N-methylaminocaproyl linker between the cluster and biotin. This construct was chosen, because of its stability with regard to release of biotin and clearing ability over a broad range of doses. In this experiment, dosing was altered slightly to model higher efficiency tumor delivery, as would likely be used in a therapeutic setting. This is done by reducing the dose of DOTA-biotin to 1.0 μg which increases the efficiency of tumor delivery (% ID/g), but places a larger burden on the clearing agent to clear circulating NR-LU-10-streptavidin.

Nude mice bearing s.c. SW-1222 xenografts (n=4 per group per timepoint) were injected at t=0 with 400 μg (1.9 nmol) of NR-LU-10-streptavidin conjugate labeled with PIP-I-125 in accordance with known procedures therefore. After 24 hours, animals were injected with 100 μg (11.25 nmol) of the CCA. At 2, 4, 8 or 24 hours later, 1.0 μg (1.24 nmol) dose of In-111-DOTA-biotin was administered. Animals were bled and euthanized by cervical dislocation at 2 and 24 hours post In-111-DOTA-biotin injection. Blood, tail, lung, liver, kidney and tumor were counted in a dual-channel gamma counter to establish the tissue concentrations of In-111 and I-125.

With each longer interval between CCA and DOTA-biotin injections, the level of In-111-DOTA-biotin in the blood was decreased. This appeared to correlate with circulating NR-LU-10-streptavidin levels in each group of animals. The intervals of 8 and 24 hours yielded both the best tumor targeting and lowest blood levels. The lack of CCA tumor compromise, even at the 24 hour timepoint, was encouraging, and the enhanced blood clearance of conjugate over this extended time period allowed the achievement of markedly improved tumor/blood ratios. Thus, CCAs offer a variety of novel dosing applications which can be exploited to improve blood (and presumably, whale body) clearance of In-111-DOTA-biotin without sacrificing tumor uptake.

D. Impact of Different Doses of Active Agent-Containing Construct.

The low circulating NR-LU-10-streptavidin levels attained in the previous experiment suggested the potential for use of higher specific activity DOTA-biotin to improve tumor efficiency. This experiment was therefore conducted to assess the effect of differing ligand doses on both absolute uptake (% ID/g) and tissue to blood ratios. The rationale for this experiment was that CCAs might allow greater efficiency of tumor targeting with a lower ligand dose due to the lower background of NR-LU-10-streptavidin level using a 24 hour interval between CCA and active agent administration. The CCA employed in this experiment was the same one as employed in Experiment C set forth above.

Nude mice bearing s.c. SW-1222 xenografts (n=4 per group per timepoint) were injected at t=0 with 400 g (1.9 nmol) of NR-LU-10-streptavidin conjugate labeled with PIP-I-125 in accordance with known procedures therefore. After 24 hours, animals were injected with 100 μg (11.25 nmol) of the CCA. Twenty-four hours later, 0.1, 0.5, 1.0, 2.0 or 5.0 μg (0.12–6.19 nmol) of In-111-DOTA-biotin were administered. Animals were bled and euthanized by cervical dislocation at 2 and 24 hours post In-111-DOTA-biotin injection. Blood, tail, lung, liver, spleen, stomach, kidney, intestines and tumor were counted in a dual-channel gamma counter to establish the tissue concentrations of In-111 and I-125.

At the lowest DOTA-biotin dose, 0.1 μg, a significant increase in blood retention of In-111-DOTA-biotin was observed, with a somewhat decreased tumor uptake compared to other doses. The blood values decreased significantly over the next 24 hours with a concomitant rise in tumor localization, probably due to tumor uptake of NR-LU-10-streptavidin that had been labeled with DOTA-biotin in the blood compartment. The overall biodistribution of In-111-DOTA-biotin in all groups was similar, showing decreasing blood levels between the 2 and 24 hour biodistributions without significant loss of tumor activity. Tumor uptake was good for all ligand doses tested, but decreased somewhat for the higher doses of 2.0 and 5.0 μg. On a % ID/g basis, these two doses showed the lowest levels of non-target retention of DOTA-biotin. Tumor to blood ratios for DOTA-biotin increased markedly with increasing ligand dose. Values at 2 hours increased with ligand dose from approximately 7 to greater than 88, while values at 24 hours ranged form 74 to 172. By utilizing CCAs with modified dose-timing parameters, consistently high efficiency tumor delivery of DOTA-biotin was achieved over a broad range of DOTA-biotin doses. Low levels of blood and non-target organ DOTA-biotin retention were also consistently observed.

E. Aqueous Solubility at Physiological Temperature (37° C.) and Extenders Between Cluster and Binding Moiety.

The 16-N-acetylgalactosamine CCA used in Experiments C and D above, characterized by a sugar unit of galNAc-$\alpha$-S-$C_6$-NH and a N-methylaminocaproyl linker between the cluster and biotin, had poor aqueous solubility at physiological temperature (less than 2 mg/mL). Also, it was hypothesized that residual NR-LU-10-streptavidin in the circulation represented a subfraction which either does not efficiently bind to the CCA, due for example to steric constraints, or binds to the CCA, but the sugars of the CCA-containing construct are not effectively presented to Ashwell receptors. To address these two issues, alternative constructs were prepared and evaluated. Those constructs may be described as follows:

| Sugar Unit | Linker between Cluster and Biotin |
| --- | --- |
| 1. (galNAc-$\alpha$-S-$C_5$-NH)$_{16}$ | N-methylaminocaproyl |
| 2. (galNAc-$\alpha$-S-$C_5$-NH)$_{16}$ | (N-methylaminocaproyl)$_3$ |
| 3. (galNAc-$\alpha$-S-$C_5$-NH)$_{32}$ | (N-methylaminocaproyl)$_3$ |
| 4. (galNAc-$\alpha$-S-$C_6$-NH)$_{16}$ | N-methylaminocaproyl |
| 5. (galNAc-$\alpha$-S-$C_4$-NH)$_{32}$ | (N-methylaminocaproyl)$_2$ |

In the first three constructs, the methylene group in the sugar unit was decreased from 6 carbons to 5 carbons in an effort to improve solubility. Also, the extended linker between the cluster and biotin in constructs 2, 3 and 5 was introduced in order to address the difficulty in clearing a subfraction of NR-LU-10-streptavidin conjugate. Construct number 5 also incorporates a four carbon sugar unit methylene group. Initial analysis of these constructs was carried out in a precomplexation experiment in Balb C mice, substantially similar to the precomplexation experiments described above. I-125-labeled NR-LU-10-streptavidin was treated with a 20-fold excess of the CCA and then introduced i.v. The clearance profiles of these precomplexed constructs revealed that the conjugate-CCA 3 complex cleared to the lowest serum levels followed by conjugate-CCA 2 complex; followed by conjugate-CCA 5 complex; followed by conjugate-CCA 4 complex; and lastly by conjugate-CCA1 complex. The CCA1 agent was determined to have been contaminated with a small amount of biotin, so that the reliability of this data with respect to that construct is questionable. However, the results with CCA2 and CCA3 indicate that the design changes were positive. Because the synthesis of the 32-sugar construct is more difficult, further CCA work focused on CCA2.

It should be noted that the solubility of CCA2 at physiological temperature was determined to be greater than 50 mg/mL.

F. Further Characterization of CCA2 of Experiment E.

CCA2 was further characterized by utilization thereof in tumored nude mice in the full pretargeting regimen with escalating CCA doses to assess tumor to blood ratios and CCA compromise (either direct by CCA binding thereto or indirect by biotin-containing CCA metabolite binding thereto) of pretargeted NR-LU-10-streptavidin.

Nude mice bearing s.c. SW-1222 xenografts (n=4 per group per timepoint) were injected at t=0 with 400 μg 1.9 nmol) of NR-LU-10-streptavidin conjugate labeled with PIP-I-125 in accordance with known procedures therefore.

After 24 hours, animals were injected with 50 μg (1×), 250 μg (5×) or 500 μg (10×) of CCA. Four hours later, a saturating dose 15 μg of In-111-DOTA-biotin was administered. Animals were bled and euthanized by cervical dislocation at 2 and 24 hours post In-111-DOTA-biotin injection. Tumor and normal tissues were counted in a dual-channel gamma counter to establish the tissue concentrations of In-111 and I125.

NR-LU-10-streptavidin conjugate concentrations at the tumor were roughly equivalent for all groups. DOTA-biotin concentrations at the tumor decreased with increasing CCA dose, falling to about 50% at the 10× dose in comparison to the concentration at the 1× dose. As illustrated in the following table, tumor to blood values of ligand were modest in association with the lowest does of clearing agent, but superb for the higher two doses at the 2 hour timepoint and even better at the 24 hour timepoint.

| Dose of cluster CA | $^{111}$In-DOTA-BT localization | |
| --- | --- | --- |
|  | tu/bl (avg tu/avg bl) @ 2h | tu/bl (avg tu/avg bl) @ 24h |
| 50 μg | 9.7 (7 68/0.79) | 18.6 (9.75/0.53) |
| 250 μg | 52.6 (5.56/0.11) | 125.2 (5.39/0.05) |
| 500 μg | 53.6 (4.11/0.08) | 94.0 (3.71/0.04) |

G. Further Characterization of Purified CCA1 of Experiment E.

Because administration of very high doses of CCA2 appeared to result in partial compromise of pretargeted conjugate, further evaluation of highly purified CCA1 was undertaken. Evaluation consisted of determining efficacy in clearance of pre-complexed conjugate and clearance of conjugate in the pretargeting schema. An evaluation of the extent of compromise of pretargeted conjugate was also undertaken. These evaluations were conducted using a control of CCA4 of Experiment E (also a construct used in Experiment B and the construct used in Experiments C and D set forth above).

Both precomplexation and pretargeted clearing experiments were carried out as earlier described. In precomplexation experiments, purified CCA1 and CCA4 of Experiment E appeared to function analogously. Both agents were also found to function nearly identically in clearing conjugate administered in the pretargeting schema. Use of high doses of the two CCAs in tumored mice in the pretargeting schema resulted in little CCA compromise of the binding capacity of the pretargeted streptavidin, wherein the ratio of conjugate to DOTA-biotin being about 5.5:1. This ratio is likely to be within 10% of the theoretical maximum ligand binding capacity of the conjugate, consisting of (on average) between 1–2 streptavidin molecules/antibody.

Kits containing one or more of the components described above are also contemplated. For instance, galactose cluster-biotin conjugate may be provided in a sterile container for use in pretargeting procedures. Alternatively, such a galactose cluster-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A clearing agent comprising:
   (a) a hepatic clearance directing moiety comprising an iterative, two branch chemical framework to which a plurality of 1-desoxy-1-thio-N-acetylgalactosamine residues are bound; and
   (b) one or two binding moieties directly or indirectly attached to the hepatic clearance directing moiety, wherein the binding moieties bind in vivo a compound to be cleared, wherein the clearing agent is characterized by a molecular mass between about 2,000 and about 20,000 daltons, and directs clearance of the compound by a hepatic pathway.

2. A clearing agent comprising:
   (a) a hepatic clearance directing moiety comprising an iterative, two branch chemical framework to which a plurality of N-acetyl-galactosamine hexose residues are bound; and
   (b) one or two binding moieties directly or indirectly attached to the hepatic clearance directing moiety, wherein the binding moieties bind in vivo a compound to be cleared, wherein the clearing agent is characterized by a molecular mass between about 2,000 and about 20,000 daltons, and directs clearance of the compound by a hepatic pathway, and

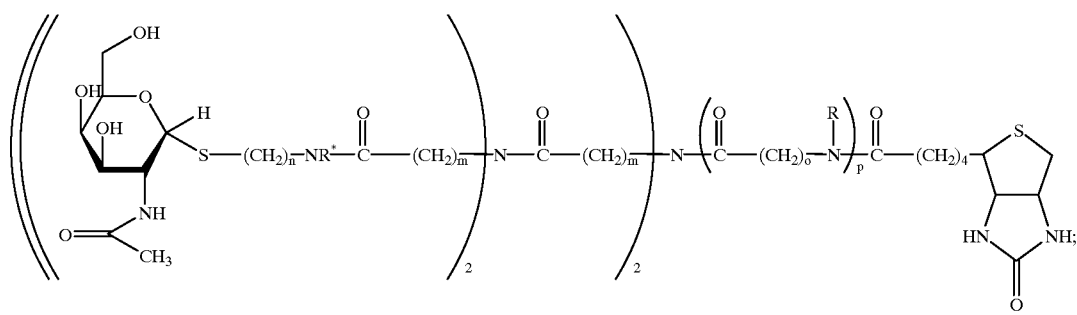

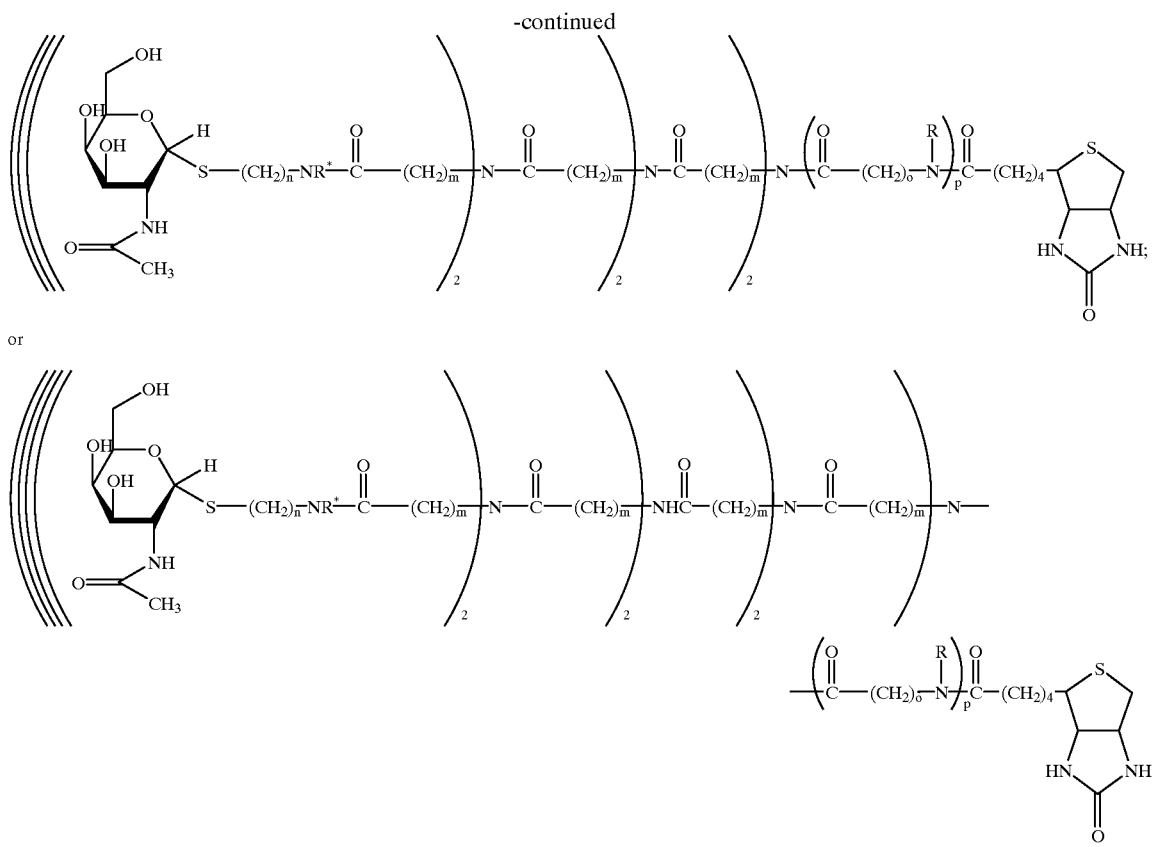

wherein n ranges from about 4 to about 8; m and o range from about 3 to about 6; p ranges from about 1 to about 10; R' is H or lower alkyl of from 1 to about 6 carbon atoms; and R is lower alkyl from about 1 to about 6 carbon atoms, phenyl, benzyl or $C_{2-6}$ lower alkyl substituted with phenyl.

3. A clearing agent of claim 2 wherein p is 2 or 3; and R are a straight chain lower alkyl of 2 carbon atoms.

4. A clearing agent of claim 3 wherein n is 5; m is 5; o is 5; and R' is H.

5. A clearing agent of claim 2 wherein p is 2 or 3; and R are a straight chain lower alkyl of 1 carbon atom.

6. A clearing agent of claim 2 wherein p is 2 or 3; and R are a straight chain lower alkyl of 1 carbon atom and a straight chain lower alkyl of 2 atoms.

7. A clearing agent of claim 6 wherein n is 5; m is 5; o is 5; and R' is H.

8. A clearing agent of claim 2 selected from the third chemical formula of claim 2, wherein n is 5, m is 5, o is 5, p is 1, R' is H, and R is methyl.

* * * * *

UNITED STATES PATENT AND TRADEMARK OFFICE
CERTIFICATE OF CORRECTION

PATENT NO.   : 6,172,045 B1
DATED        : January 9, 2001
INVENTOR(S)  : Louis J. Theodore and Donald B. Axworthy It is certified that error appears in the above-identified patent and that said Letters Patent is hereby corrected as shown below:

Columns 67, 68, 69 and 70,
The structure should appear as:

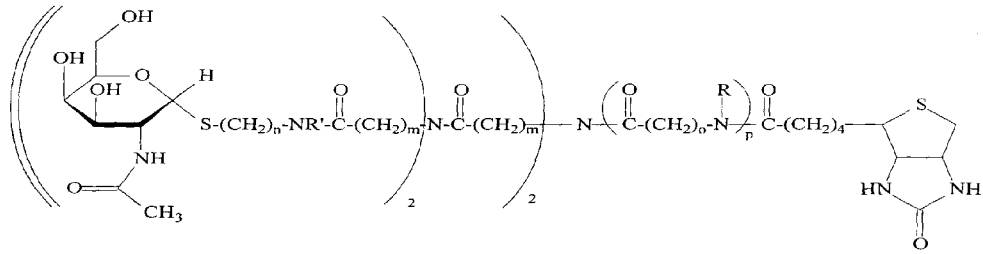

Column 68,
Line 50, should read -- wherein the clearing agent is selected from the following: --.

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,172,045 B1
DATED : January 9, 2001
INVENTOR(S) : Theodore et al.

It is certified that error appears in the above-identified patent and that said Letters Patent is hereby corrected as shown below:

Column 68,
Line 50, should read -- wherein the clearing agent is selected from the following: --.

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,172,045 B1  
DATED         : January 9, 2001  
INVENTOR(S)   : Theodore et al.

Page 1 of 1

It is certified that error appears in the above-identified patent and that said Letters Patent is hereby corrected as shown below:

Columns 67, 68, 69 and 70,
In all instances the asterisk should be corrected to appear as a prime and in the third structure, a fourth subscript 2 after the last large parenthesis from left to right is missing. The structures should appear as --

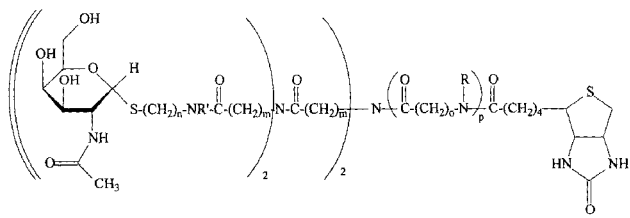

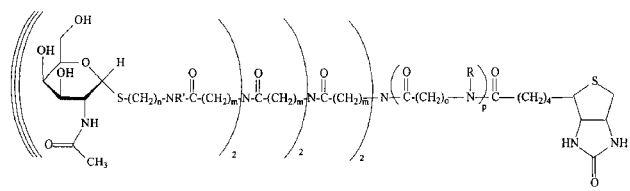

or

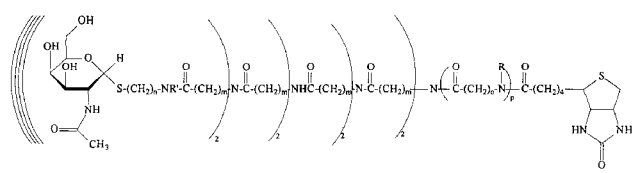

--

Column 68,
Line 50, should read -- wherein the clearing agent is selected from the following: --.

Signed and Sealed this

Seventh Day of September, 2004

JON W. DUDAS
*Director of the United States Patent and Trademark Office*